(12) United States Patent
Maguire et al.

(10) Patent No.: US 6,964,660 B2
(45) Date of Patent: Nov. 15, 2005

(54) TISSUE ABLATION DEVICE ASSEMBLY AND METHOD OF ELECTRICALLY ISOLATING A PULMONARY VEIN OSTIUM FROM AN ATRIAL WALL

(75) Inventors: Mark A. Maguire, San Jose, CA (US); Michael D. Lesh, Mill Valley, CA (US); James C. Peacock, III, San Carlos, CA (US); Edward L. Carcamo, Millbrae, CA (US)

(73) Assignee: Atrionix, Inc., Palo Alto, CA (US)

( * ) Notice: Subject to any disclaimer, the term of this patent is extended or adjusted under 35 U.S.C. 154(b) by 133 days.

(21) Appl. No.: 10/274,742

(22) Filed: Oct. 21, 2002

(65) Prior Publication Data

US 2003/0125726 A1 Jul. 3, 2003

Related U.S. Application Data

(60) Division of application No. 09/435,281, filed on Nov. 5, 1999, now Pat. No. 6,652,515, which is a continuation-in-part of application No. 08/889,798, filed on Jul. 8, 1997, now Pat. No. 6,024,740, and a continuation-in-part of application No. 09/199,736, filed on Nov. 25, 1998, now Pat. No. 6,117,101.
(60) Provisional application No. 60/133,677, filed on May 11, 1999.

(51) Int. Cl.$^7$ ................................................ A61B 18/18
(52) U.S. Cl. .......................................... 606/41; 607/122
(58) Field of Search ................................ 606/41; 607/99, 607/101, 102, 113, 122; 600/374, 393

(56) References Cited

U.S. PATENT DOCUMENTS

| | | |
|---|---|---|
| 3,938,502 A | 2/1976 | Bom |
| 4,117,836 A | 10/1978 | Erikson |
| 4,316,742 A | 2/1982 | Canning, Jr. |
| 4,411,266 A | 10/1983 | Cosman |
| 4,449,528 A | 5/1984 | Auth et al. |
| 4,522,205 A | 6/1985 | Taylor et al. |
| 4,569,801 A | 2/1986 | Molloy et al. |
| 4,641,649 A | 2/1987 | Walinsky et al. |
| 4,660,571 A | 4/1987 | Hess et al. |
| 4,662,368 A | 5/1987 | Hussein et al. |
| 4,669,469 A | 6/1987 | Gifford, III et al. |
| 4,672,962 A | 6/1987 | Hershenson |
| 4,673,563 A | 6/1987 | Berne et al. |
| 4,676,258 A | 6/1987 | Inokuchi et al. |
| 4,699,147 A | 10/1987 | Chilson et al. |
| 4,757,820 A | 7/1988 | Itoh |
| 4,762,129 A | 8/1988 | Bonzel |
| 4,790,311 A | 12/1988 | Ruiz |
| 4,807,620 A | 2/1989 | Strul et al. |

(Continued)

FOREIGN PATENT DOCUMENTS

| | | |
|---|---|---|
| EP | 472368 B1 | 6/1995 |
| EP | 711573 B1 | 6/2003 |

(Continued)

OTHER PUBLICATIONS

Avitall, et al., "Physics and Engineering of Transcatheter Cardiac Tissue Ablation," JACC. vol. 22 (3):921–932, Sep. 1993.

(Continued)

*Primary Examiner*—Roy D. Gibson

(57) ABSTRACT

This invention is related to a tissue ablation system and method that treats atrial arrhythmia by ablating a circumferential region of tissue at a location where a pulmonary vein extends from an atrium. The system includes a circumferential ablation member with an ablation element and also includes a delivery assembly for delivering the ablation member to the location. The circumferential ablation member is generally adjustable between different configurations to allow both the delivery through a delivery sheath into the atrium and the ablative coupling between the ablation element and the circumferential region of tissue.

19 Claims, 58 Drawing Sheets

U.S. PATENT DOCUMENTS

| | | |
|---|---|---|
| 4,841,977 A | 6/1989 | Griffith et al. |
| 4,882,777 A | 11/1989 | Narula |
| 4,898,591 A | 2/1990 | Jang et al. |
| 4,936,281 A * | 6/1990 | Stasz |
| 4,940,064 A * | 7/1990 | Desai |
| 4,942,863 A * | 7/1990 | Chou et al. |
| 4,945,912 A * | 8/1990 | Langberg |
| 4,951,677 A * | 8/1990 | Crowley et al. |
| 4,976,711 A * | 12/1990 | Parins et al. |
| 4,998,933 A * | 3/1991 | Eggers et al. |
| 5,000,185 A * | 3/1991 | Yock |
| 5,002,059 A * | 3/1991 | Crowley et al. |
| 5,035,694 A * | 7/1991 | Kasprzyk et al. |
| 5,078,717 A * | 1/1992 | Parins et al. |
| 5,090,958 A | 2/1992 | Sahota |
| 5,104,393 A | 4/1992 | Isner et al. |
| 5,131,397 A | 7/1992 | Crowley |
| 5,147,355 A | 9/1992 | Friedman et al. |
| 5,156,157 A | 10/1992 | Valenta, Jr. et al. |
| 5,178,618 A | 1/1993 | Kandarpa |
| 5,186,177 A | 2/1993 | O'Donnell et al. |
| 5,190,540 A | 3/1993 | Lee |
| 5,195,990 A | 3/1993 | Weldon |
| 5,209,229 A | 5/1993 | Gilli |
| 5,222,501 A | 6/1993 | Ideker et al. |
| 5,226,430 A | 7/1993 | Spears et al. |
| 5,228,442 A | 7/1993 | Imran |
| 5,231,995 A | 8/1993 | Desai |
| 5,255,679 A | 10/1993 | Imran |
| 5,263,493 A | 11/1993 | Avitall |
| 5,281,215 A | 1/1994 | Milder |
| 5,292,321 A | 3/1994 | Lee |
| 5,293,868 A | 3/1994 | Nardella |
| 5,293,869 A | 3/1994 | Edwards et al. |
| 5,295,484 A | 3/1994 | Marcus et al. |
| 5,313,943 A | 5/1994 | Houser et al. |
| 5,324,255 A | 6/1994 | Passafaro et al. |
| 5,325,860 A | 7/1994 | Seward et al. |
| 5,331,966 A | 7/1994 | Bennett et al. |
| 5,342,292 A | 8/1994 | Nita et al. |
| 5,344,435 A | 9/1994 | Turner et al. |
| 5,345,936 A | 9/1994 | Pomeranz et al. |
| 5,345,940 A | 9/1994 | Seward et al. |
| 5,348,554 A | 9/1994 | Imran et al. |
| 5,368,035 A | 11/1994 | Hamm et al. |
| 5,368,557 A | 11/1994 | Nita et al. |
| 5,368,558 A | 11/1994 | Nita |
| 5,370,678 A | 12/1994 | Edwards et al. |
| 5,372,138 A | 12/1994 | Crowley et al. |
| 5,385,148 A | 1/1995 | Lesh et al. |
| 5,385,544 A | 1/1995 | Edwards et al. |
| 5,391,197 A | 2/1995 | Burdette et al. |
| 5,409,000 A | 4/1995 | Imran |
| 5,411,524 A | 5/1995 | Rahul |
| 5,421,338 A | 6/1995 | Crowley et al. |
| 5,423,808 A | 6/1995 | Edwards et al. |
| 5,423,811 A | 6/1995 | Imran et al. |
| 5,427,119 A | 6/1995 | Swartz et al. |
| 5,433,708 A | 7/1995 | Nichols et al. |
| 5,437,664 A | 8/1995 | Cohen et al. |
| 5,447,509 A | 9/1995 | Mills et al. |
| 5,449,380 A | 9/1995 | Chin |
| 5,454,373 A | 10/1995 | Koger et al. |
| 5,456,682 A | 10/1995 | Edwards et al. |
| 5,474,530 A | 12/1995 | Passafaro et al. |
| 5,484,400 A | 1/1996 | Edwards et al. |
| 5,487,385 A | 1/1996 | Avitall |
| 5,496,312 A | 3/1996 | Klicek |
| 5,496,346 A | 3/1996 | Horzewski et al. |
| 5,497,119 A | 3/1996 | Tedrow et al. |
| 5,497,774 A | 3/1996 | Swartz et al. |
| 5,500,012 A * | 3/1996 | Brucker et al. ............ 607/122 |
| 5,501,227 A | 3/1996 | Yock |
| 5,505,730 A | 4/1996 | Edwards |
| 5,506,702 A | 4/1996 | Simpson |
| 5,509,900 A | 4/1996 | Kirkman |
| 5,522,873 A | 6/1996 | Jackman et al. |
| 5,545,161 A | 8/1996 | Imran |
| 5,545,193 A | 8/1996 | Fleischman et al. |
| 5,549,661 A | 8/1996 | Kordis et al. |
| 5,558,672 A | 9/1996 | Edwards et al. |
| 5,558,720 A | 9/1996 | Sarraf et al. |
| 5,562,720 A | 10/1996 | Stern et al. |
| 5,564,440 A | 10/1996 | Swartz et al. |
| 5,571,088 A | 11/1996 | Lennox et al. |
| 5,571,159 A | 11/1996 | Alt |
| 5,575,766 A | 11/1996 | Swartz et al. |
| 5,575,772 A | 11/1996 | Lennox |
| 5,575,788 A | 11/1996 | Baker et al. |
| 5,575,810 A | 11/1996 | Swanson et al. |
| 5,582,609 A | 12/1996 | Swanson et al. |
| 5,588,432 A | 12/1996 | Crowley |
| 5,642,736 A | 7/1997 | Avitall |
| 5,645,082 A | 7/1997 | Sung et al. |
| 5,658,278 A | 8/1997 | Imran et al. |
| 5,666,954 A | 9/1997 | Chapelon et al. |
| 5,673,695 A | 10/1997 | McGee et al. |
| 5,676,662 A | 10/1997 | Fleischhacker et al. |
| 5,683,445 A | 11/1997 | Swoyer |
| 5,685,322 A | 11/1997 | Sung et al. |
| 5,685,839 A | 11/1997 | Edwards et al. |
| 5,687,723 A | 11/1997 | Avitall |
| 5,687,729 A | 11/1997 | Schaetzle |
| 5,688,267 A | 11/1997 | Panescu et al. |
| 5,690,611 A | 11/1997 | Swartz et al. |
| 5,693,078 A | 12/1997 | Desai et al. |
| 5,697,925 A | 12/1997 | Taylor |
| 5,697,927 A | 12/1997 | Imran et al. |
| 5,702,438 A | 12/1997 | Avitall |
| 5,715,818 A | 2/1998 | Swartz et al. |
| 5,716,389 A | 2/1998 | Walinsky et al. |
| 5,718,231 A | 2/1998 | Dewhurst et al. |
| 5,718,241 A | 2/1998 | Ben-Haim et al. |
| 5,718,701 A | 2/1998 | Shai et al. |
| 5,720,775 A | 2/1998 | Larnard |
| 5,722,401 A | 3/1998 | Pietroski et al. |
| 5,722,403 A | 3/1998 | McGee et al. |
| 5,722,963 A | 3/1998 | Lurie et al. |
| 5,725,494 A | 3/1998 | Brisken |
| 5,725,512 A | 3/1998 | Swartz et al. |
| 5,728,062 A | 3/1998 | Brisken |
| 5,730,127 A | 3/1998 | Avitall |
| 5,730,704 A | 3/1998 | Avitall |
| 5,733,315 A | 3/1998 | Burdette et al. |
| 5,735,280 A | 4/1998 | Sherman et al. |
| 5,735,811 A | 4/1998 | Brisken |
| 5,735,846 A | 4/1998 | Panescu et al. |
| 5,741,249 A | 4/1998 | Moss et al. |
| 5,741,320 A | 4/1998 | Thornton et al. |
| 5,743,870 A | 4/1998 | Edwards |
| 5,743,903 A | 4/1998 | Stern et al. |
| 5,749,880 A | 5/1998 | Banas et al. |
| 5,755,663 A | 5/1998 | Larsen et al. |
| 5,755,664 A | 5/1998 | Rubenstein |
| 5,755,715 A | 5/1998 | Stern et al. |
| 5,755,760 A | 5/1998 | Maguire et al. |
| 5,769,846 A | 6/1998 | Edwards et al. |
| 5,782,239 A | 7/1998 | Webster, Jr. |
| RE35,880 E | 8/1998 | Waldman et al. |
| 5,797,877 A | 8/1998 | Hamilton et al. |
| 5,797,903 A | 8/1998 | Swanson et al. |

| | | | |
|---|---|---|---|
| 5,797,905 A | 8/1998 | Fleischman et al. | |
| 5,800,378 A | 9/1998 | Edwards et al. | |
| 5,800,379 A | 9/1998 | Edwards | |
| 5,800,413 A | 9/1998 | Swartz et al. | |
| 5,800,428 A | 9/1998 | Nelson et al. | |
| 5,800,429 A | 9/1998 | Edwards | |
| 5,807,249 A | 9/1998 | Qin et al. | |
| 5,807,308 A | 9/1998 | Edwards | |
| 5,807,391 A | 9/1998 | Wijkamp | |
| 5,807,395 A | 9/1998 | Mulier et al. | |
| 5,824,046 A | 10/1998 | Smith et al. | |
| 5,846,218 A | 12/1998 | Brisken et al. | |
| 5,851,232 A | 12/1998 | Lois | |
| 5,891,134 A | 4/1999 | Goble et al. | |
| 5,928,279 A | 7/1999 | Shannon et al. | |
| 5,938,660 A | 8/1999 | Swartz et al. | |
| 5,971,983 A | 10/1999 | Lesh | |
| 6,004,269 A | 12/1999 | Crowley et al. | |
| 6,006,755 A | 12/1999 | Edwards | |
| 6,012,457 A | 1/2000 | Lesh | |
| 6,024,740 A | 2/2000 | Lesh et al. | |
| 6,064,902 A | 5/2000 | Haissaguerre et al. | |
| 6,071,279 A | 6/2000 | Whayne et al. | |
| 6,071,281 A | 6/2000 | Burnside et al. | |
| 6,142,993 A * | 11/2000 | Whayne et al. | 606/41 |
| 6,179,835 B1 | 1/2001 | Panescu et al. | |
| 6,241,754 B1 | 6/2001 | Swanson et al. | |
| 6,251,109 B1 | 6/2001 | Hassett et al. | |

FOREIGN PATENT DOCUMENTS

| | | |
|---|---|---|
| WO | WO 93/00958 A1 | 1/1993 |
| WO | WO 93/08755 A1 | 5/1993 |
| WO | WO 93/16632 A1 | 9/1993 |
| WO | WO 93/20767 A1 | 10/1993 |
| WO | WO 93/20770 A2 | 10/1993 |
| WO | WO 93/20886 A1 | 10/1993 |
| WO | WO 94/00050 A1 | 1/1994 |
| WO | WO 94/21167 A1 | 9/1994 |
| WO | WO 94/21168 A1 | 9/1994 |
| WO | WO 94/21665 A1 | 9/1994 |
| WO | WO 95/10318 A1 | 4/1995 |
| WO | WO 95/10319 A1 | 4/1995 |
| WO | WO 95/10321 A1 | 4/1995 |
| WO | WO 95/19737 A1 * | 7/1995 |
| WO | WO 96/00036 A1 * | 1/1996 |
| WO | WO 96/10961 A1 * | 4/1996 |
| WO | WO 96/26875 A1 * | 9/1996 |
| WO | WO 96/32885 A1 * | 10/1996 |
| WO | WO 96/32897 A1 * | 10/1996 |
| WO | WO 97/32525 A1 * | 9/1997 |
| WO | WO 97/37607 A2 | 10/1997 |
| WO | WO 97/45156 A2 | 12/1997 |
| WO | WO 98/02201 A1 | 1/1998 |
| WO | WO 98/26724 A1 | 6/1998 |
| WO | WO 99/00064 A1 | 1/1999 |
| WO | WO 99/02096 A1 | 1/1999 |

OTHER PUBLICATIONS

Cox, et al., "The Surgical Treatment of Atrial Fibrillation: 1. Summary of the current concepts of the mechanisms of atrial flutter and atrial fibrillation," J. Thorac Cardiovasc Surg 1991 101:402–5.

Cox, et al., "The Surgical Treatment of Atrial Fibrillation: IV. Surgical technique," The Journal of Thoracic and Cardiovascular Surgery 1991, pp. 584–592.

Diederich, et al., "Induction of Hyperthermia Using An Intracavitary Multielement Ultrasonic Applicator," Transactions in Biomedical Engineering, vol. 36 (4):432–438.

Diederich, et al., "The development of Intracavitary ultrasonic applicators for hyperthermia: A design and experimental study," Medical Physics, Jul./Aug. 1990.

Fram, et al., "Feasibility of Radiofrequency Powered, Thermal Balloon Ablation of Atrioventricular Bypass Tracts Via the Coronary Sinus: In Vivo Canine Studies," vol. 18:1518–1530 Aug. 1995.

Haissaguerre et al., "Right and Left Atrial Radiofrequency Catheter Therapy of Paroxysmal Atrial Fibrillation," Journal of Cardiovascular Electrophysiology, vol. 7 (12):1132–1144 Dec. 1996.

Hindricks, et al., "Ix Nonphamacologic Management Catheter Ablation," Current Management of Arrythmias, pp. 373–378.

Jais, et al., "Biatrial Dimensions Relevant to Catheter Ablation," NASPE $17^{th}$ Annual Scientific Sessions Abstract, Dec. 1995.

Jais, et. al., "A Focal Source of Atrial Fibrillation Treated by Discreet Radiofrequency Ablation," Circllulation, vol. 95(3):572–576, Feb. 4, 1997.

McMath, et al., "Percutaneous laser balloon coagulation of accessory pathways," Diagnostic and Therapeutic Cardiovascular Interventions, 1991.

Schuger, et. al., "Long–term Effects of Percutaneous Laser Balloon Ablation From the Canine Coronary Sinus," Circulation, vol. 88(3):947–954, Sep. 1992.

Sueda, et al., "Simple left atrial procedure for chronic atrial fibrillation associated with mitral valve disease," Ann Thorac Surg. 62:1796–1800 1996.

Weber, Hetmut P., Cardiovascular Application of the ND:YAG Laser: in Medicine and Surgery, 2:pp.54–59, 21988. . . .

Weber, Helmut P., "Laser versus Radiofrequency Catheter Ablation of Ventricular Myocardium in Dogs: A Comparative Test, " Cardiology 88, pp.346–352, 1997.

Weber, Helmut P., "Laser Catheter Coagulation of Atrial Myocardium for Ablation of Atrioventricular Nodal Reentrant Tachycardia" Europeoan Heart Journal, vol. 18, pp. 487–495, 1997.

Borbola, J., "Transcatheter Laser Ablation of Atrioventricular Nodal Reenatrant Tachycardia –Do We Really Need a Newer Energy Source?", European Heart Journal, vol. 18, pp. 487–495, 1997.

Weber, Helmut P., et al., "Transcatheter Endornyocardial Laser Revascularization: A Feasibiity Test", the Thoracic and Cardiovascular Surgeon, vol. 46, pp. 74–76, Apr. 1998.

Weber, Helmut P., et al., "Percultaneous Nd: YAG Laser Coagulation of Ventricular Myocardium in Dogs Using a Special Electrode Laser Catheter", PASE, vol. 12, pp. 899–910, Jun. 1989.

* cited by examiner

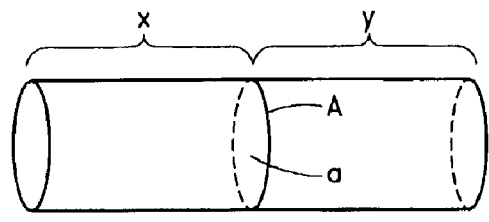
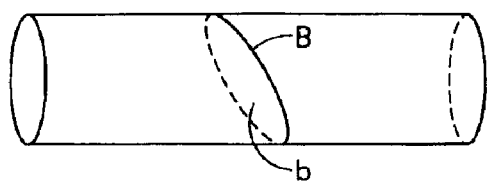
FIG. 2A   FIG. 2B
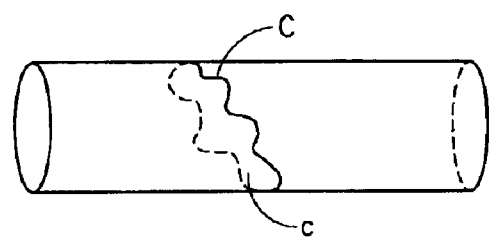
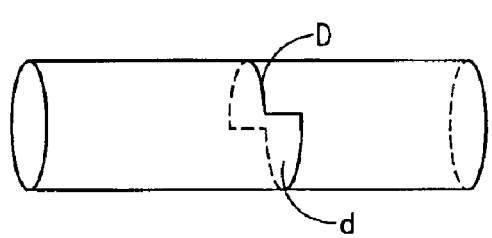
FIG. 2C   FIG. 2D
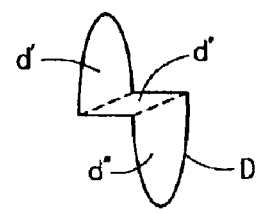
FIG. 2E

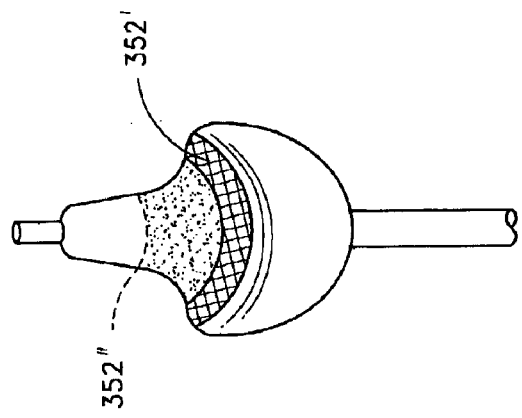
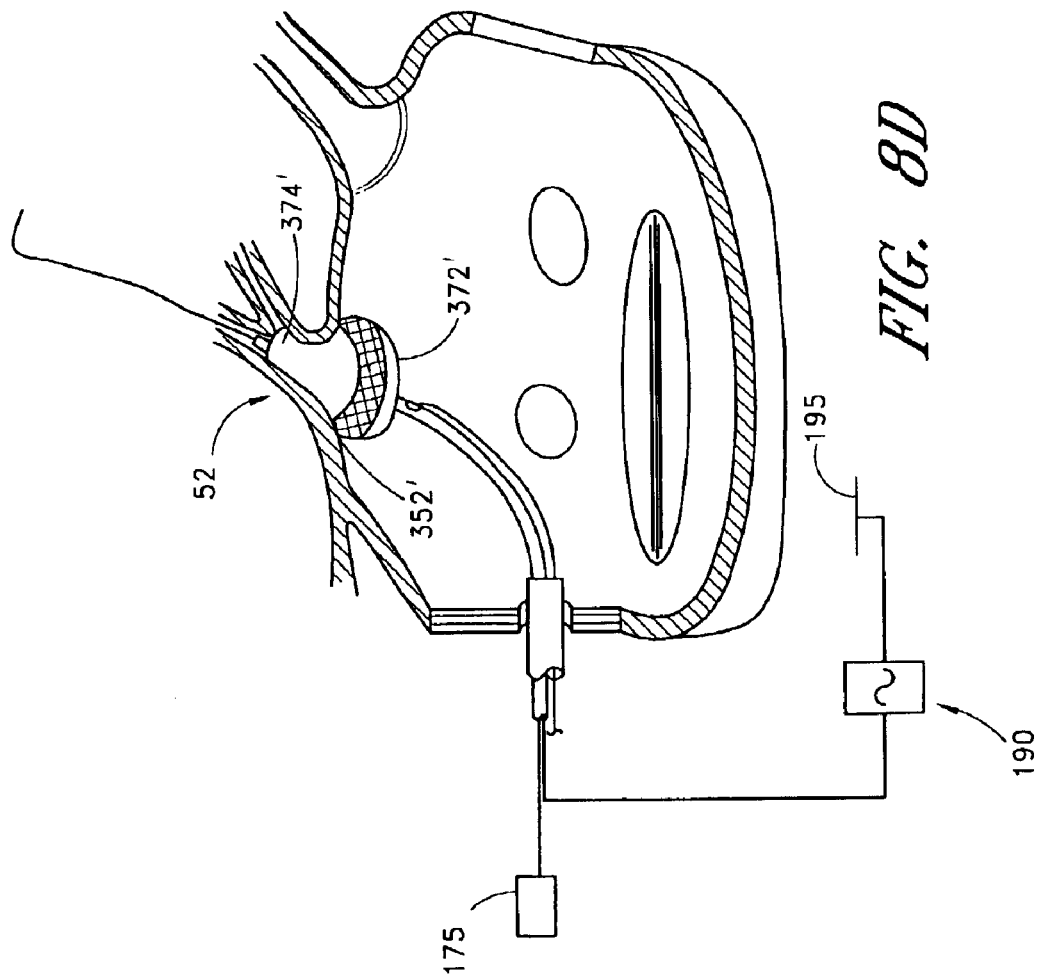
FIG. 8E
FIG. 8D

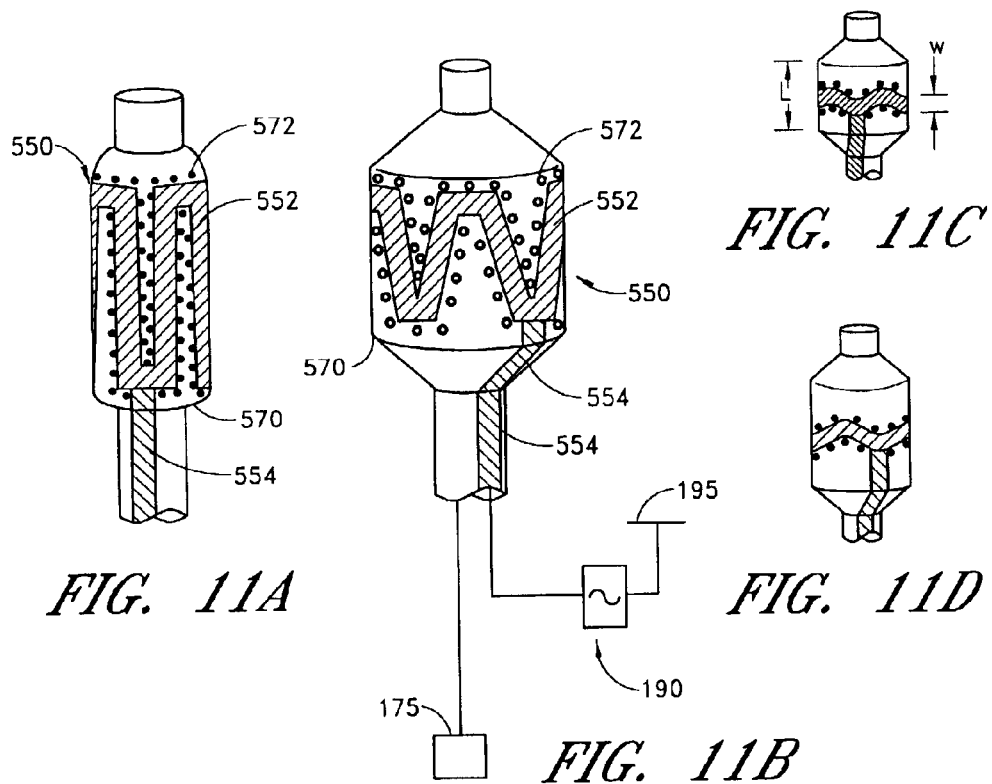
FIG. 11A
FIG. 11B
FIG. 11C
FIG. 11D
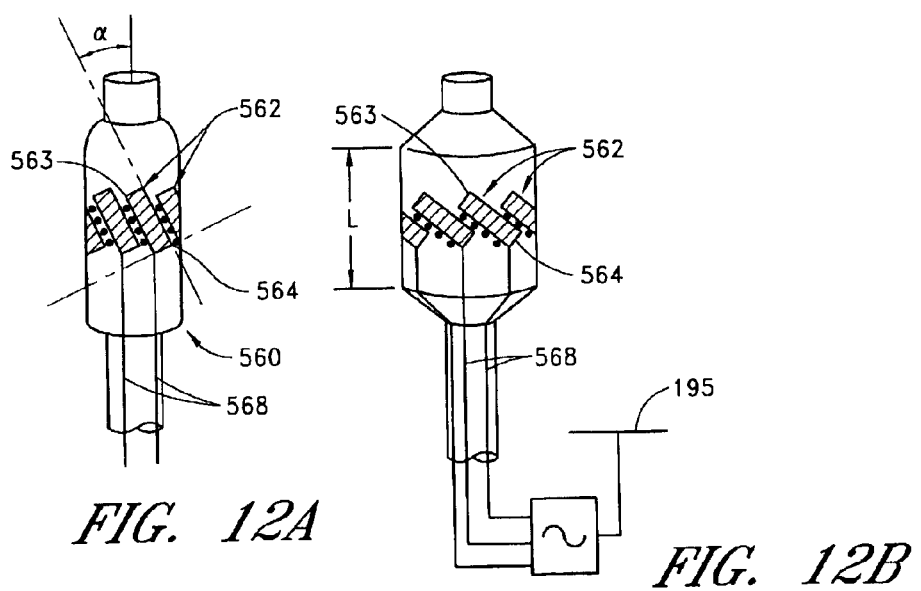
FIG. 12A
FIG. 12B

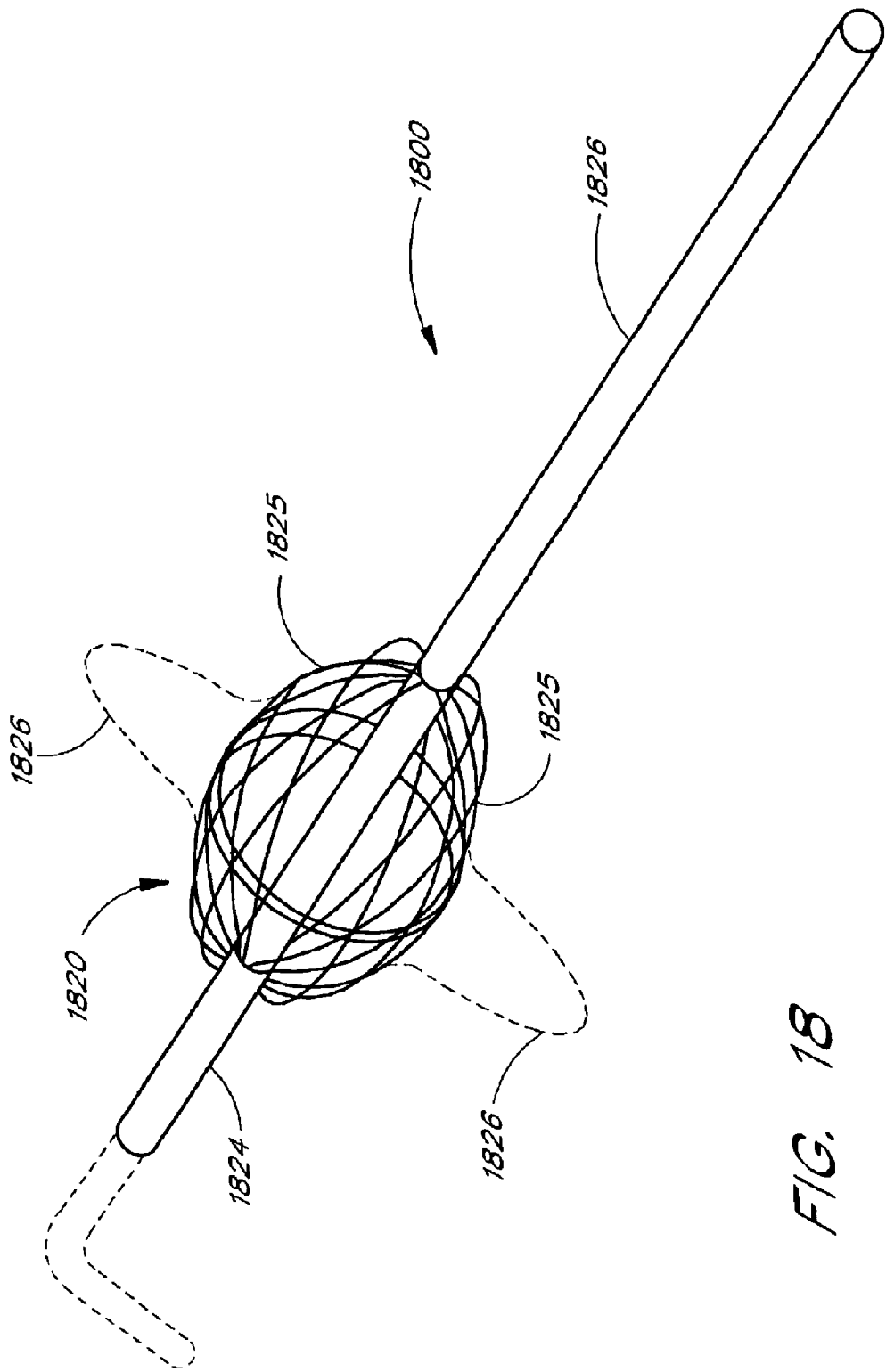

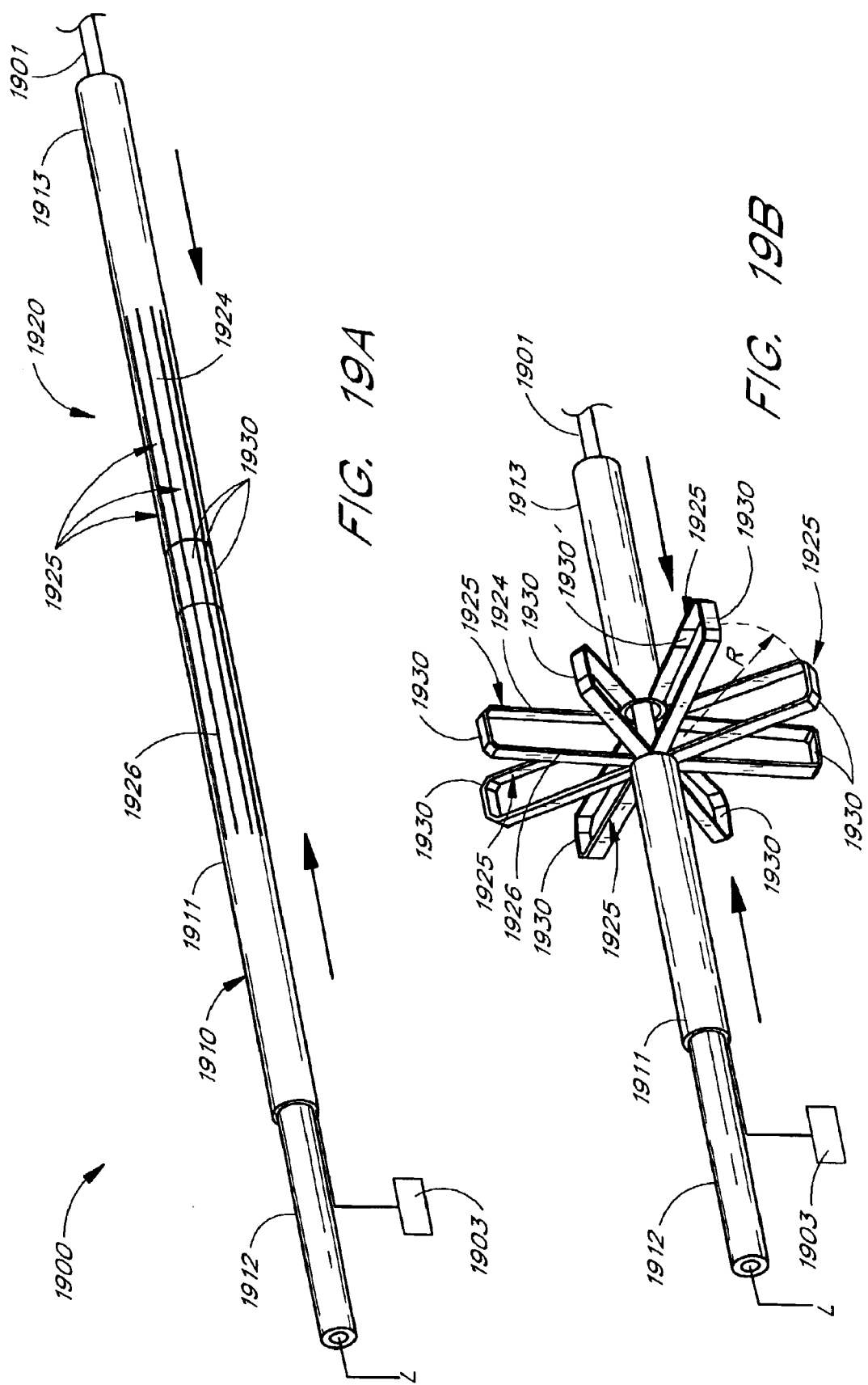

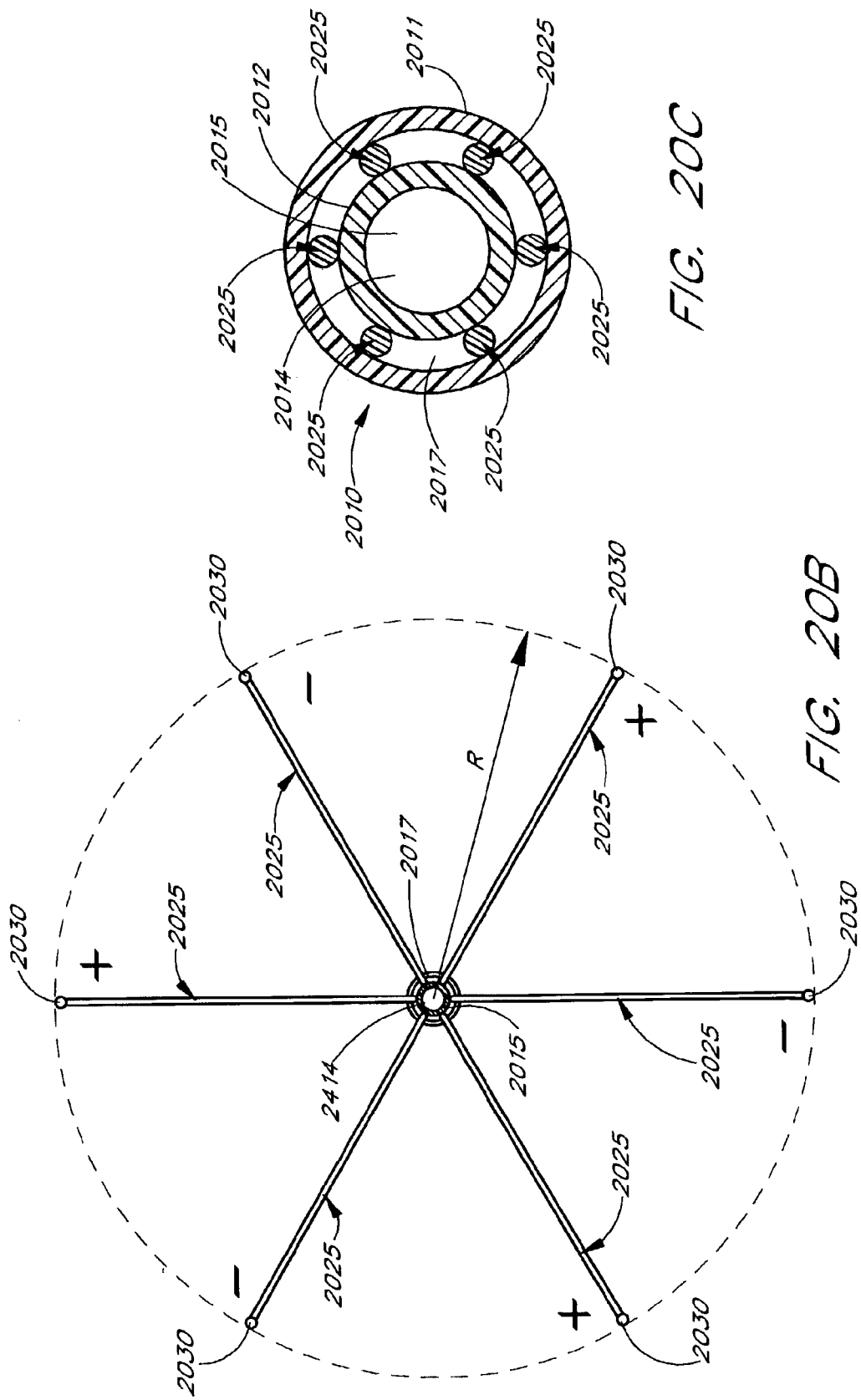

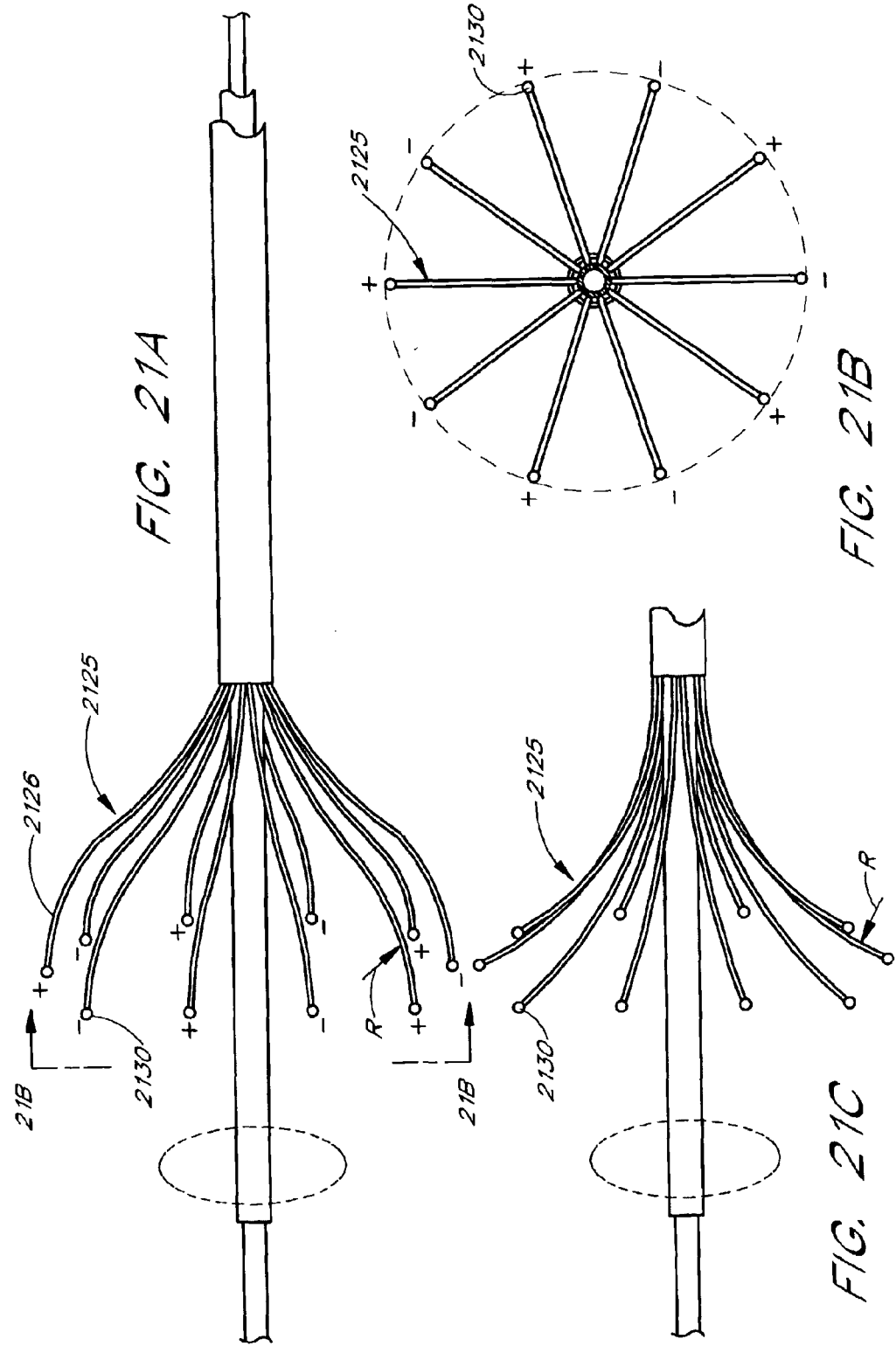

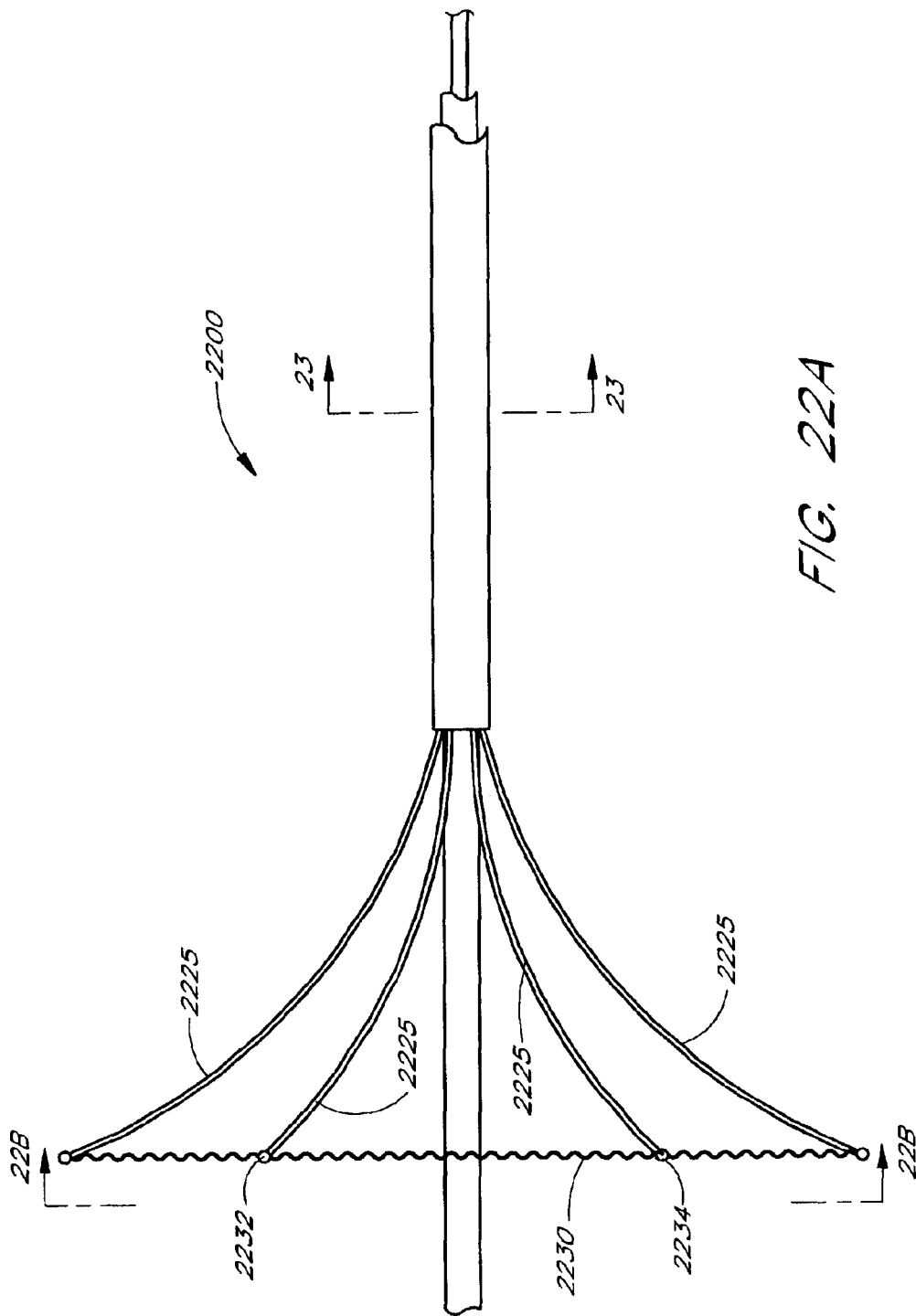

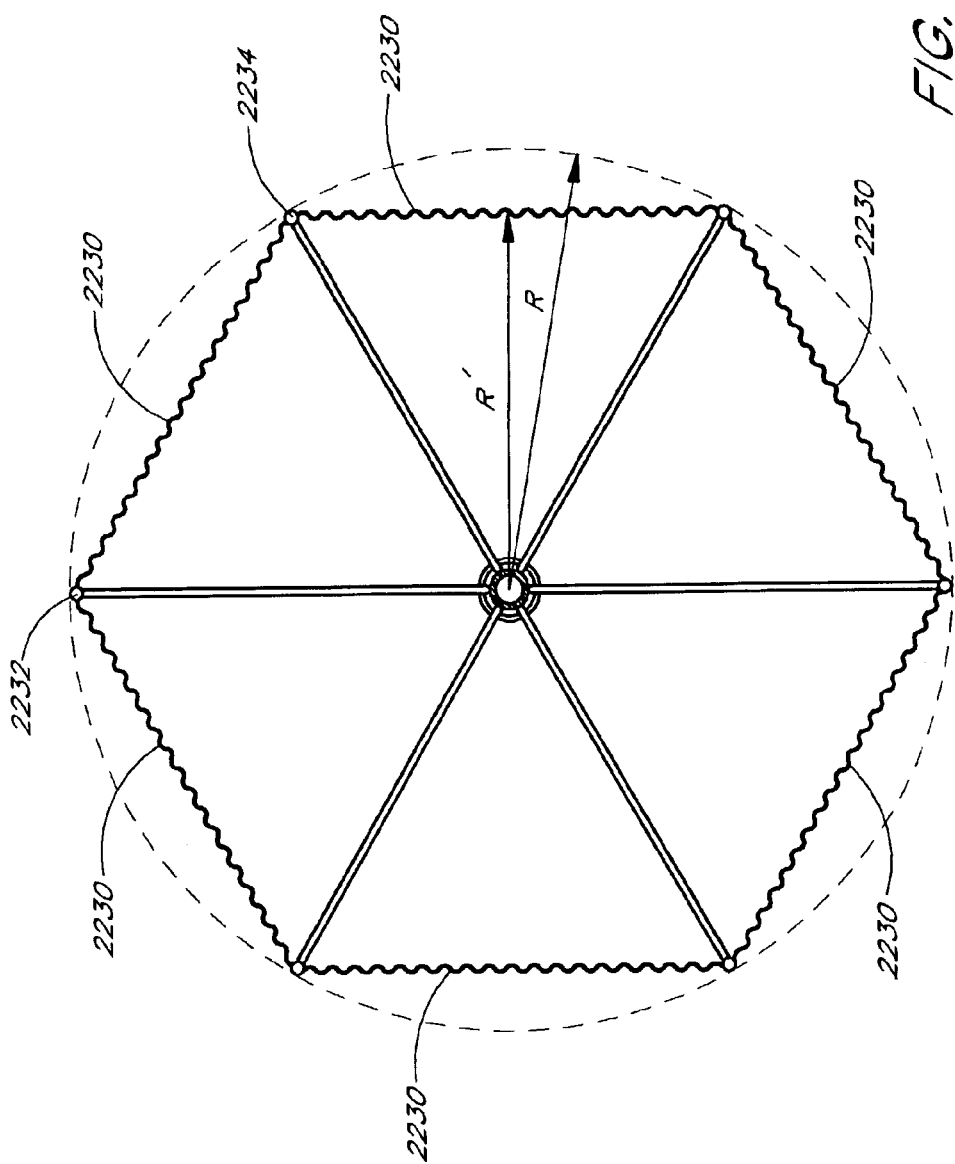

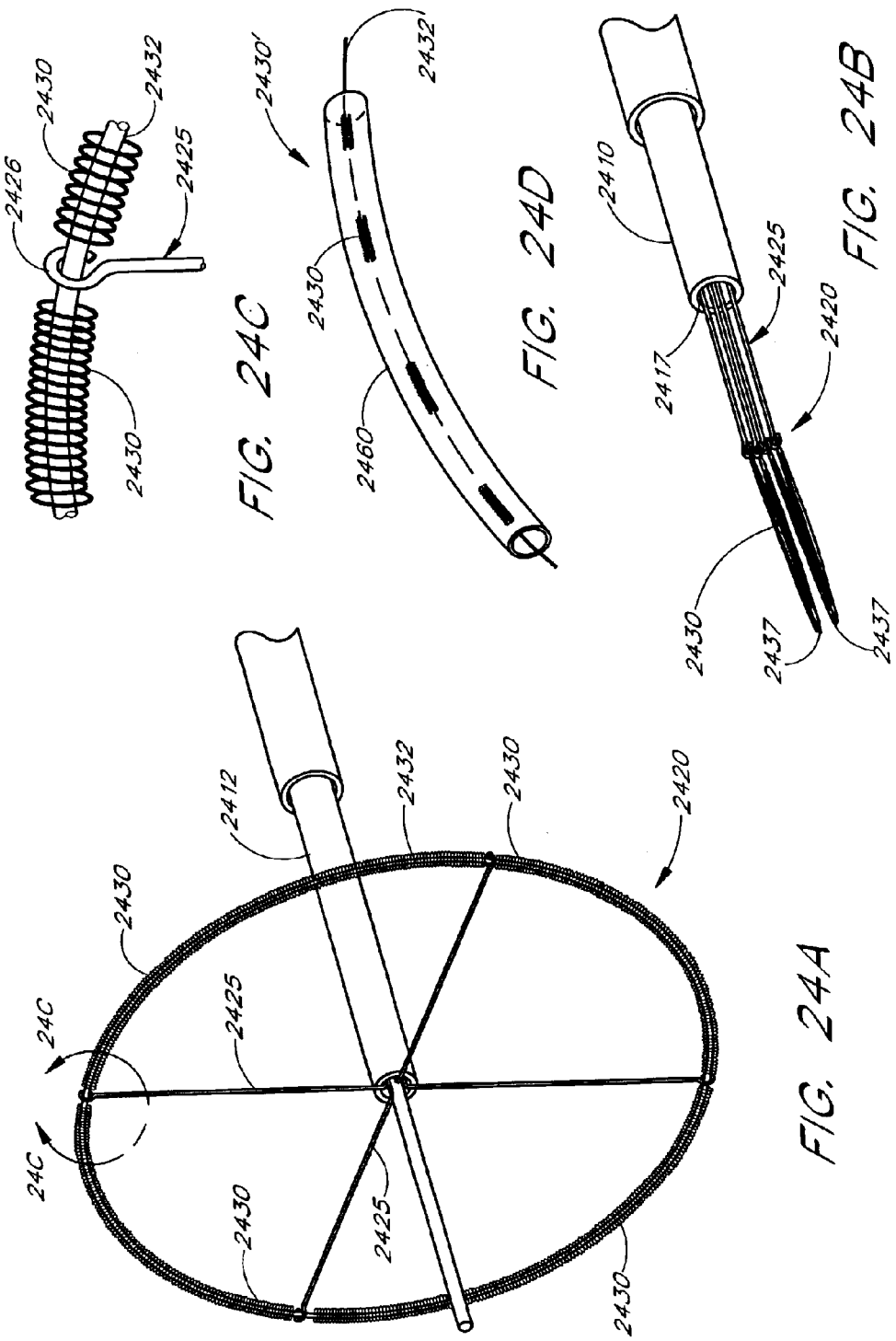

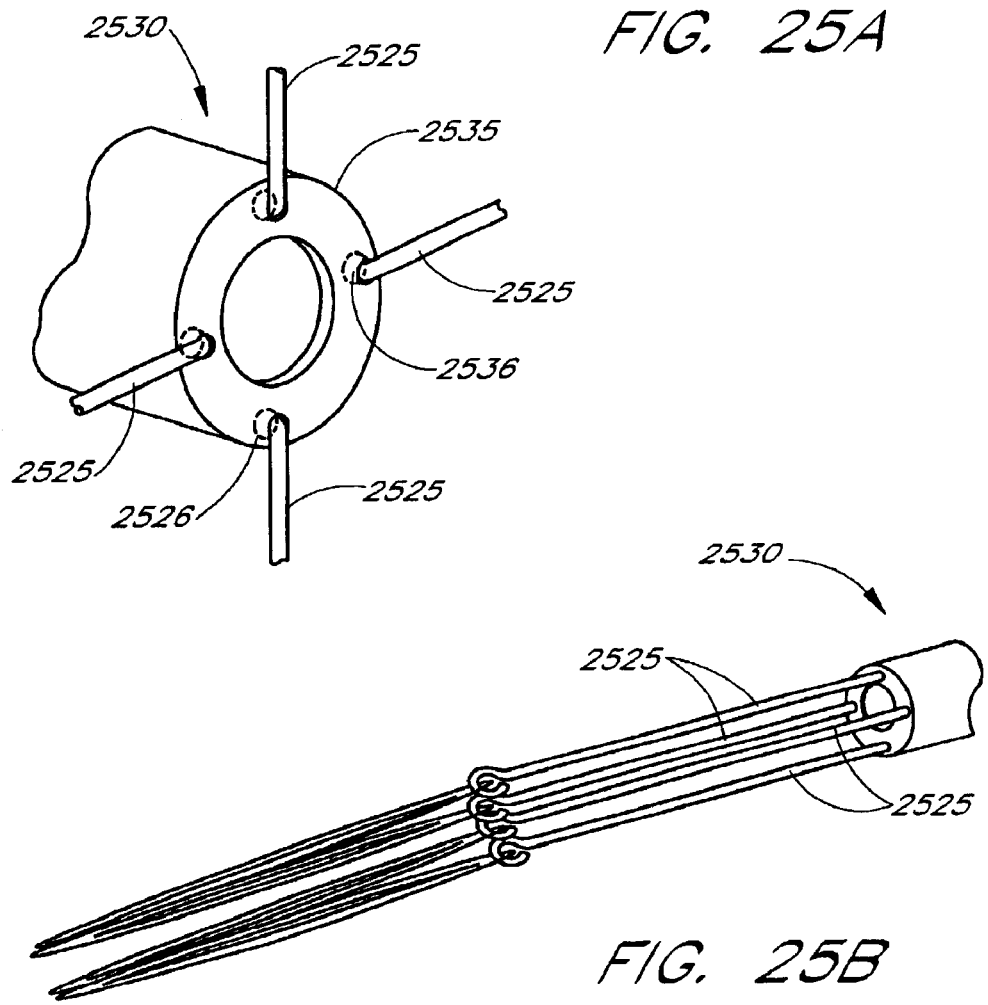
FIG. 25A
FIG. 25B
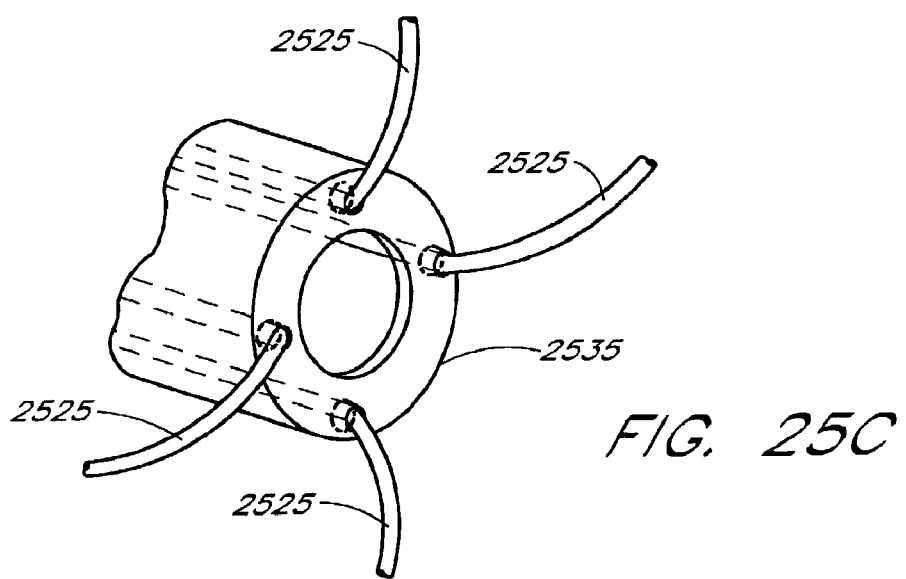
FIG. 25C

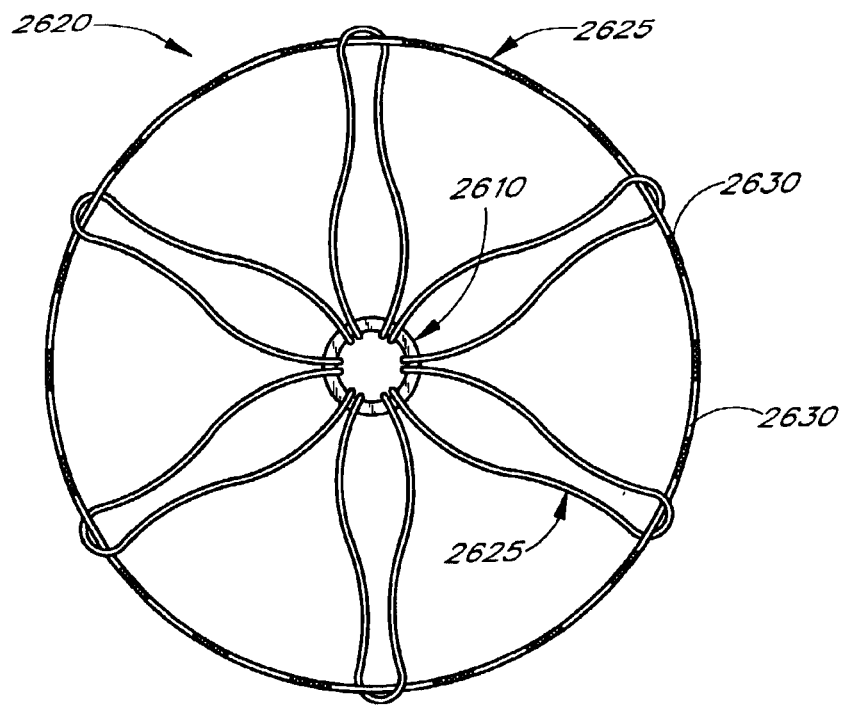
FIG. 26A
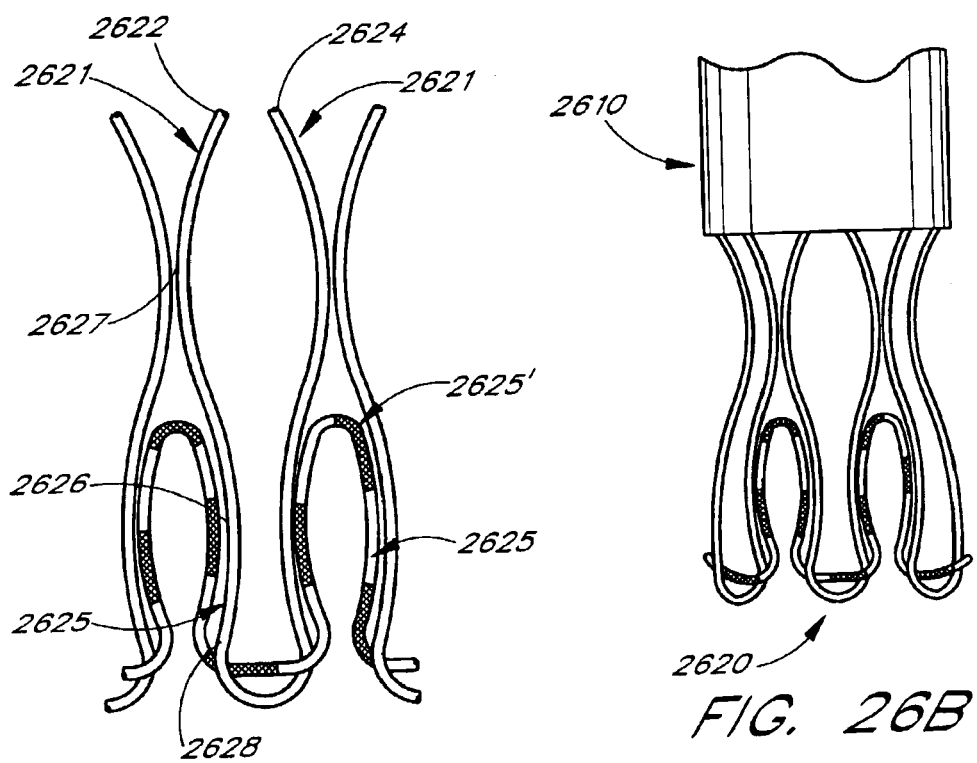
FIG. 26C
FIG. 26B

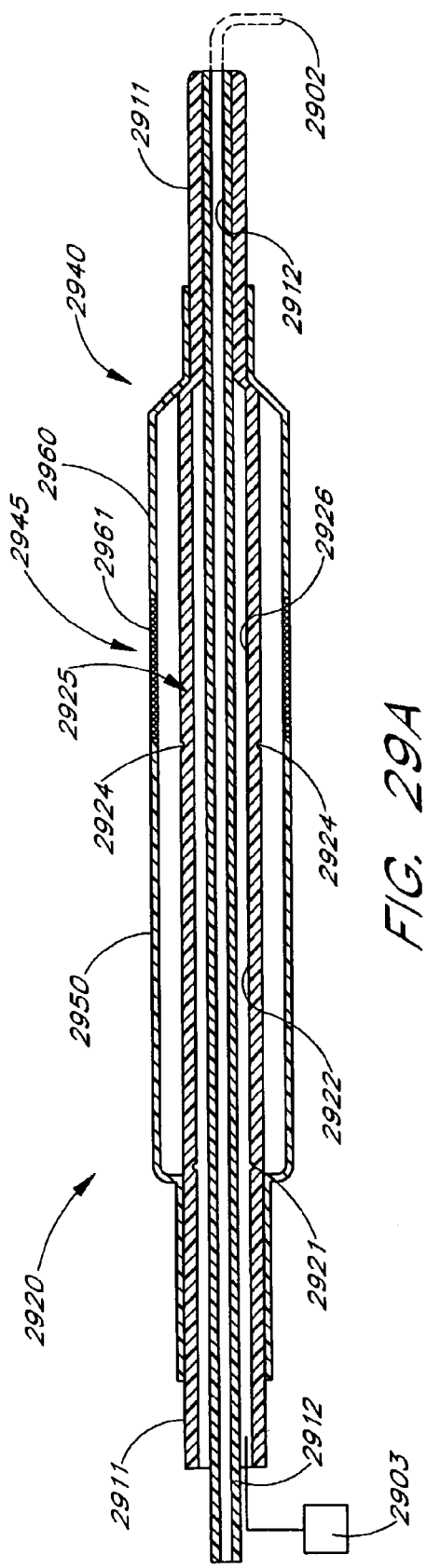
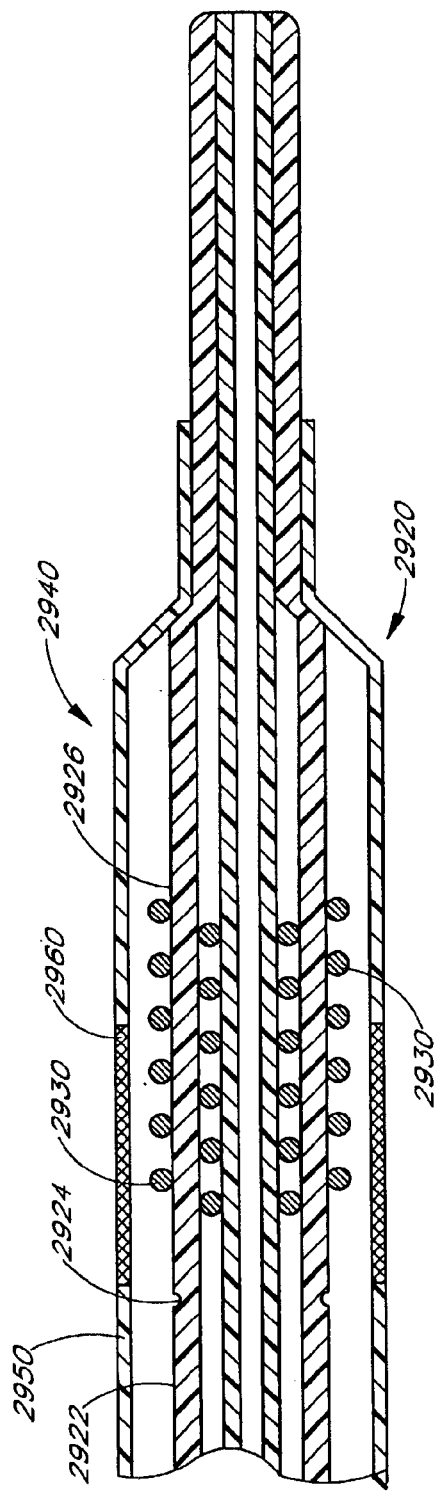
FIG. 29A
FIG. 29B

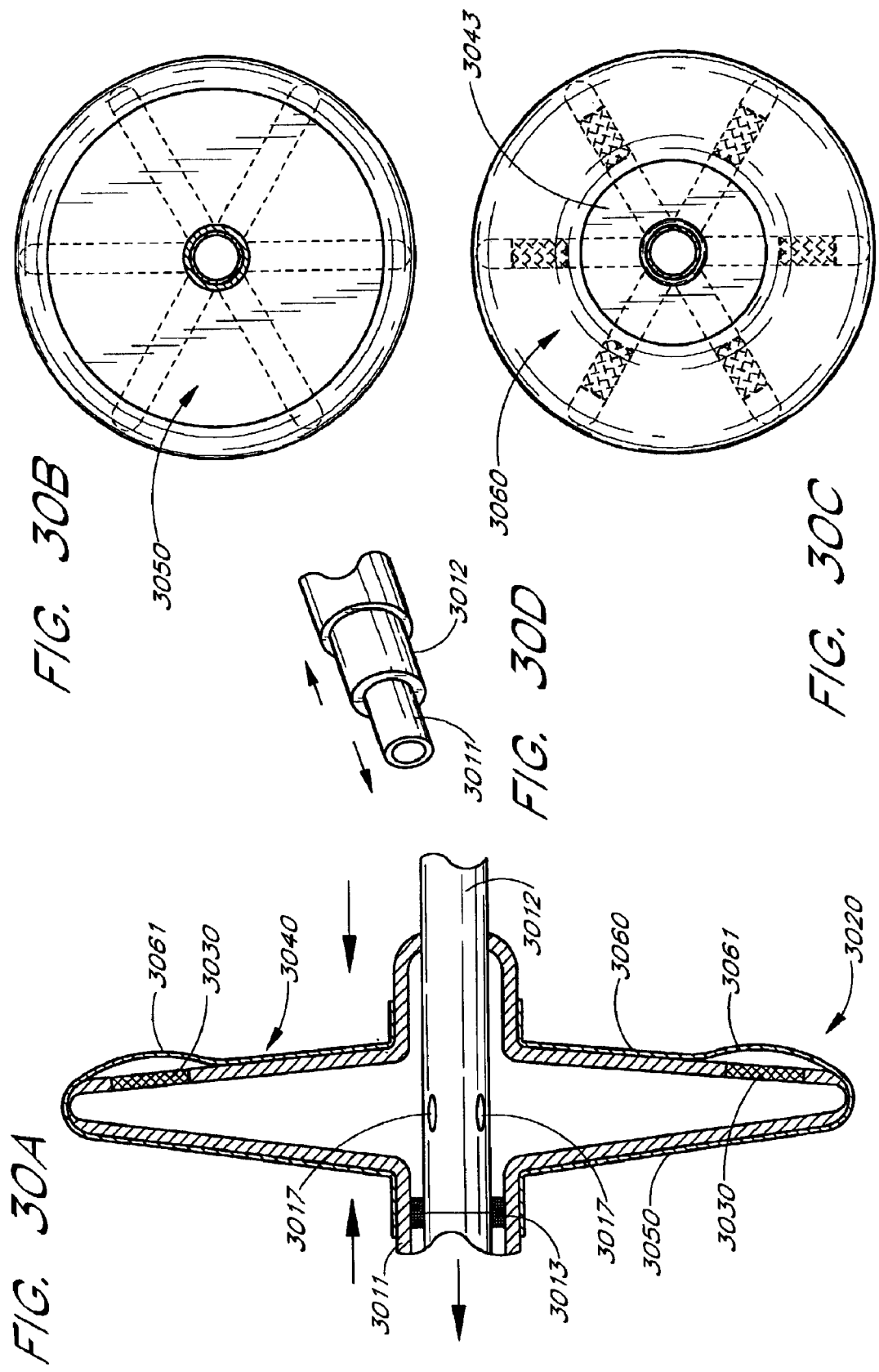

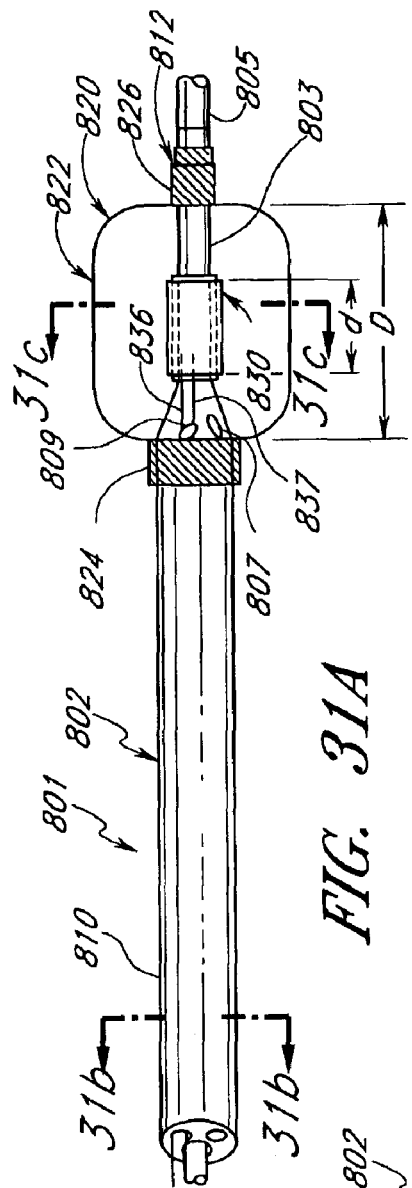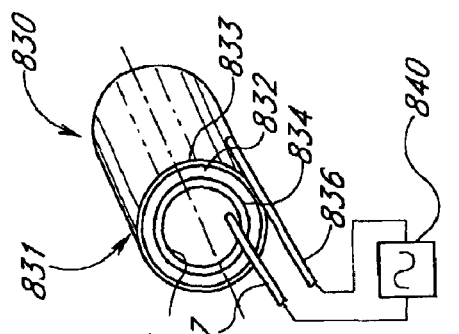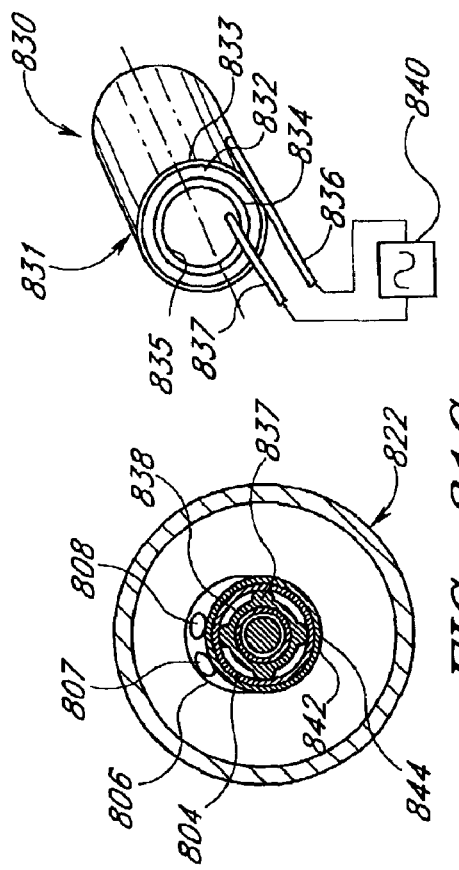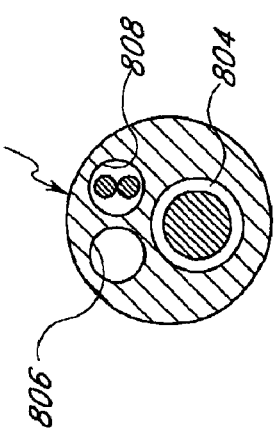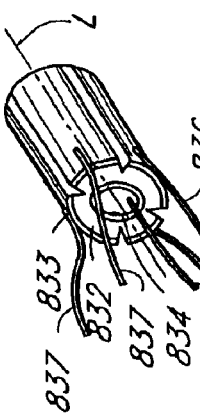

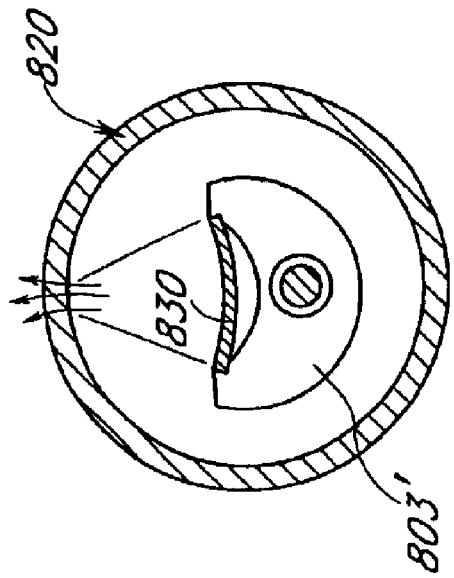
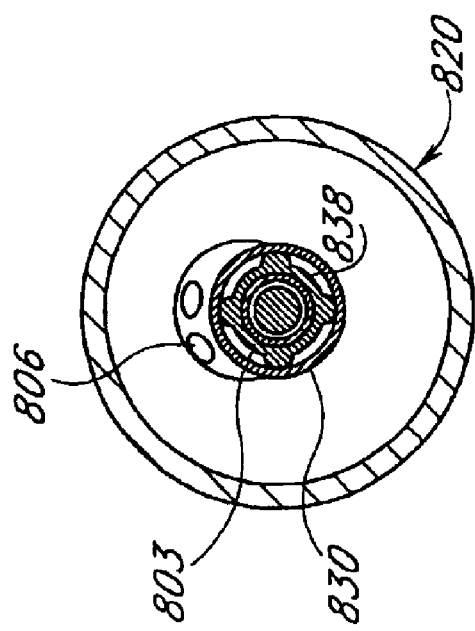
FIG. 34B
FIG. 34A

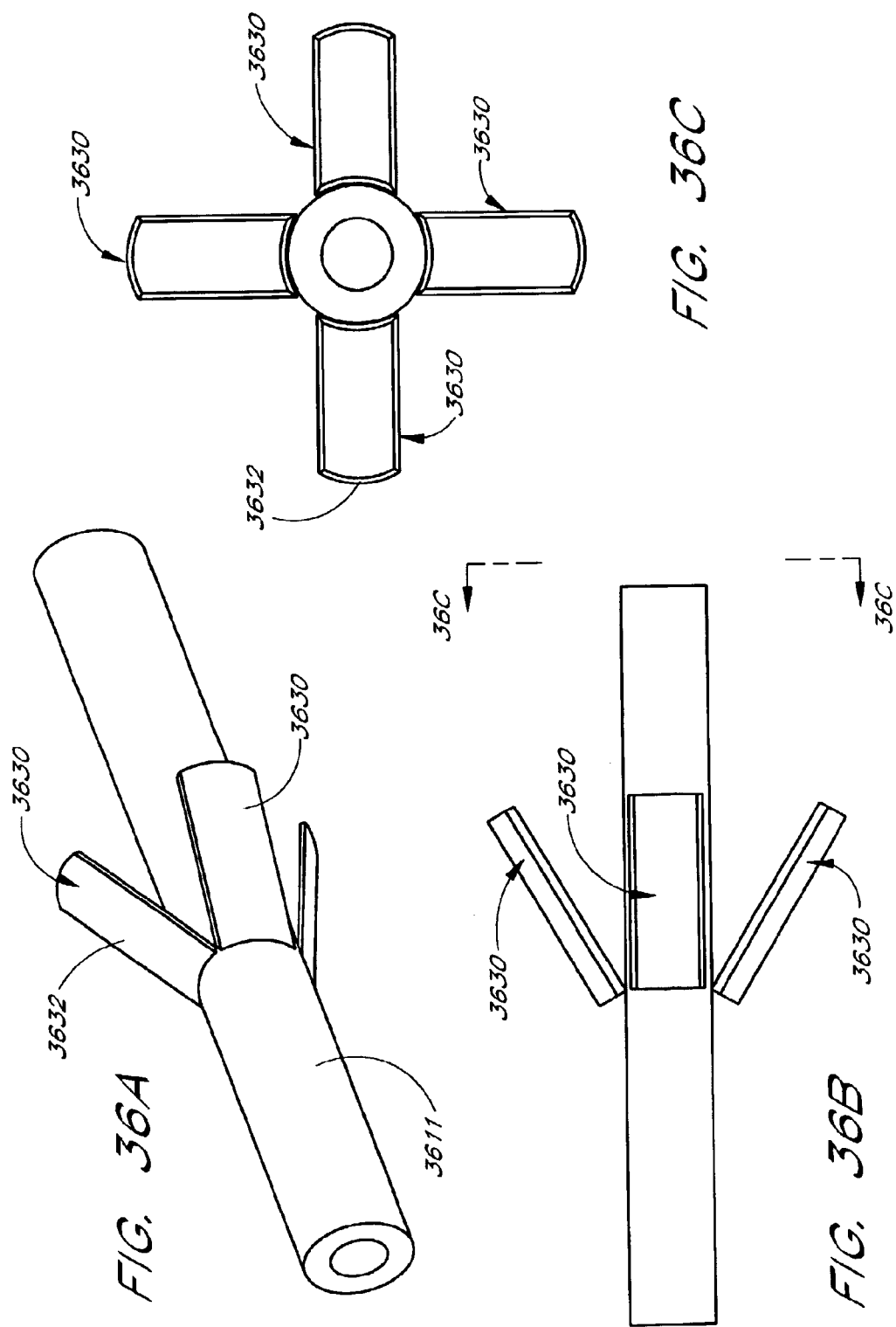

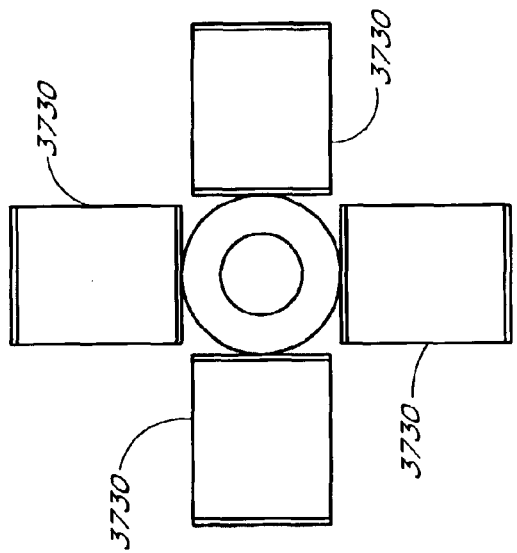
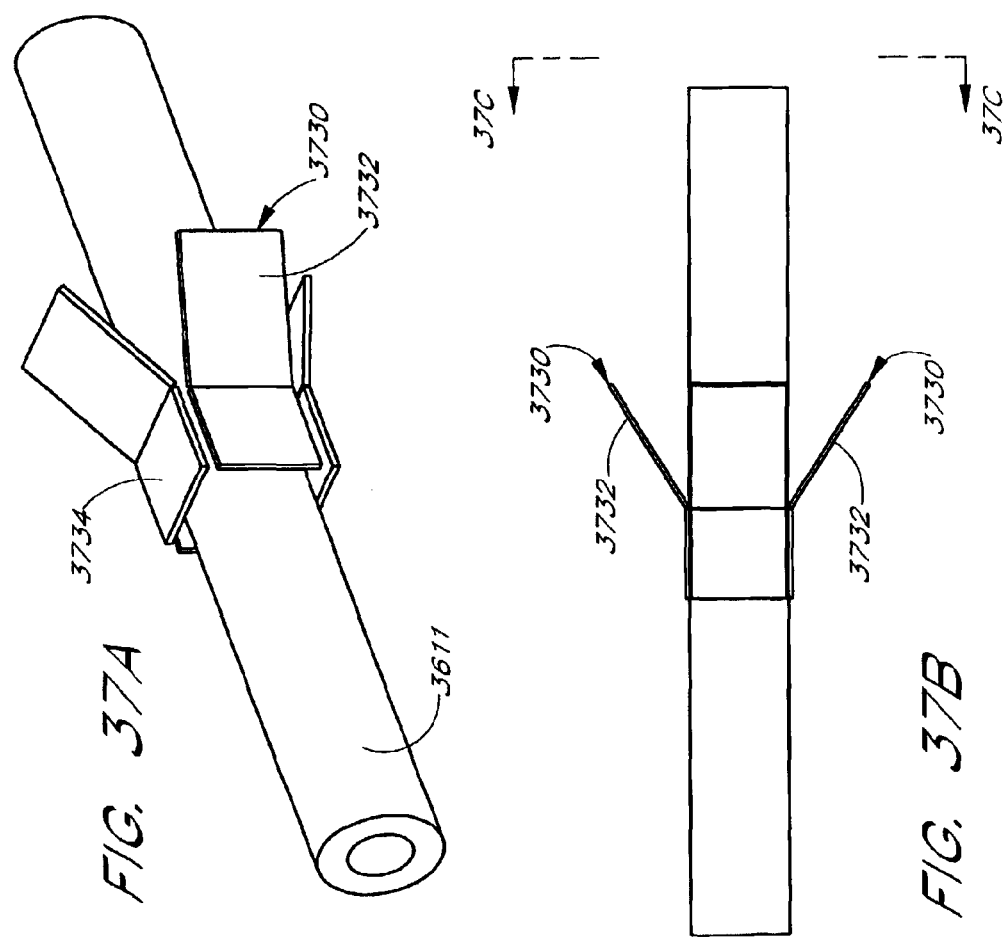

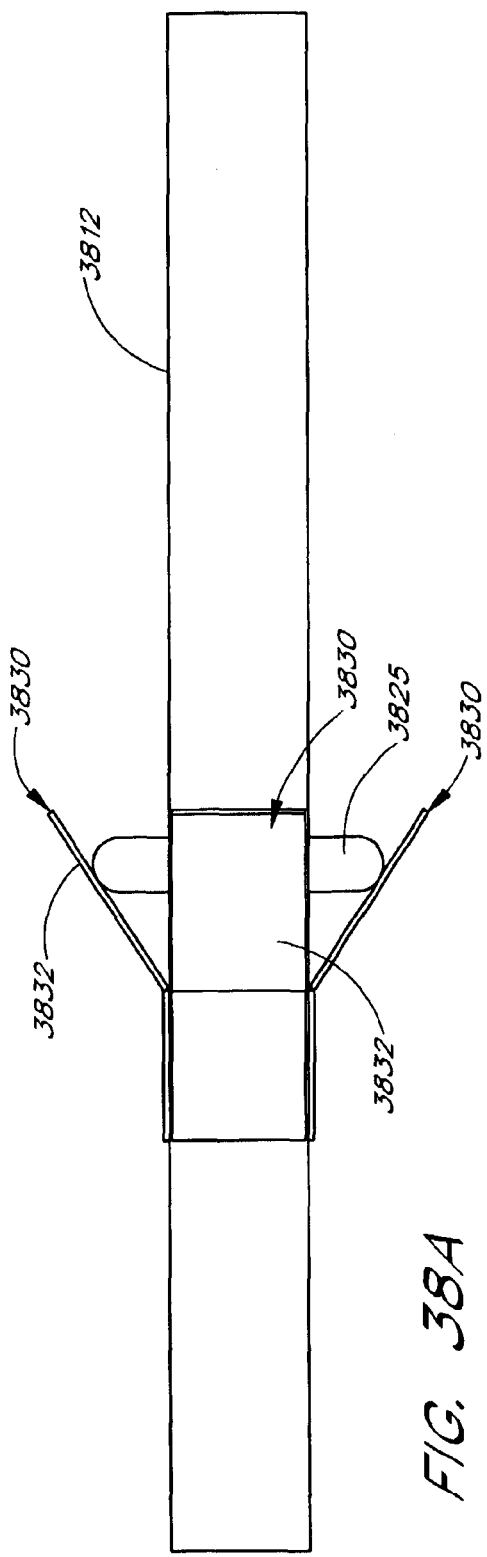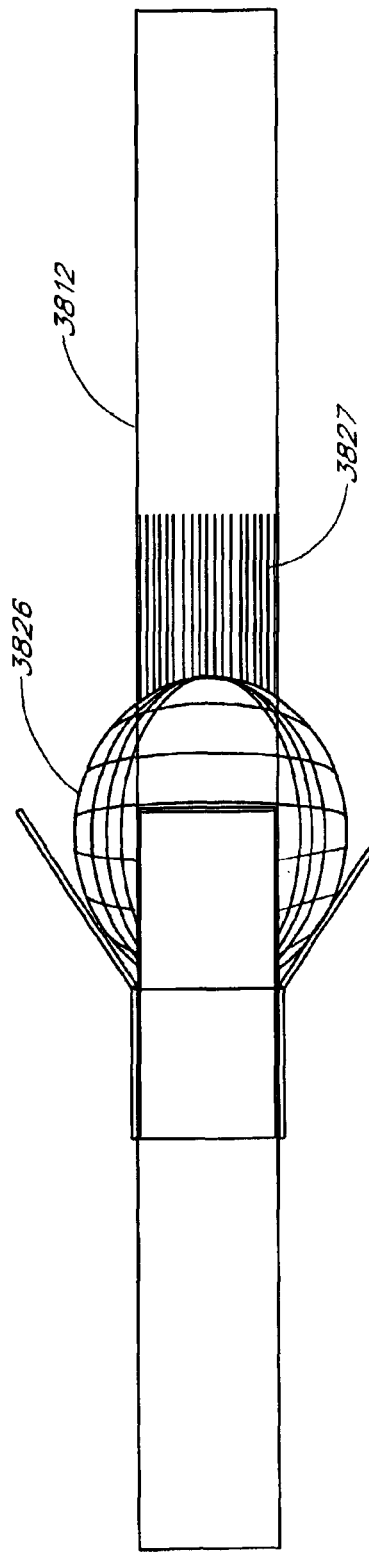

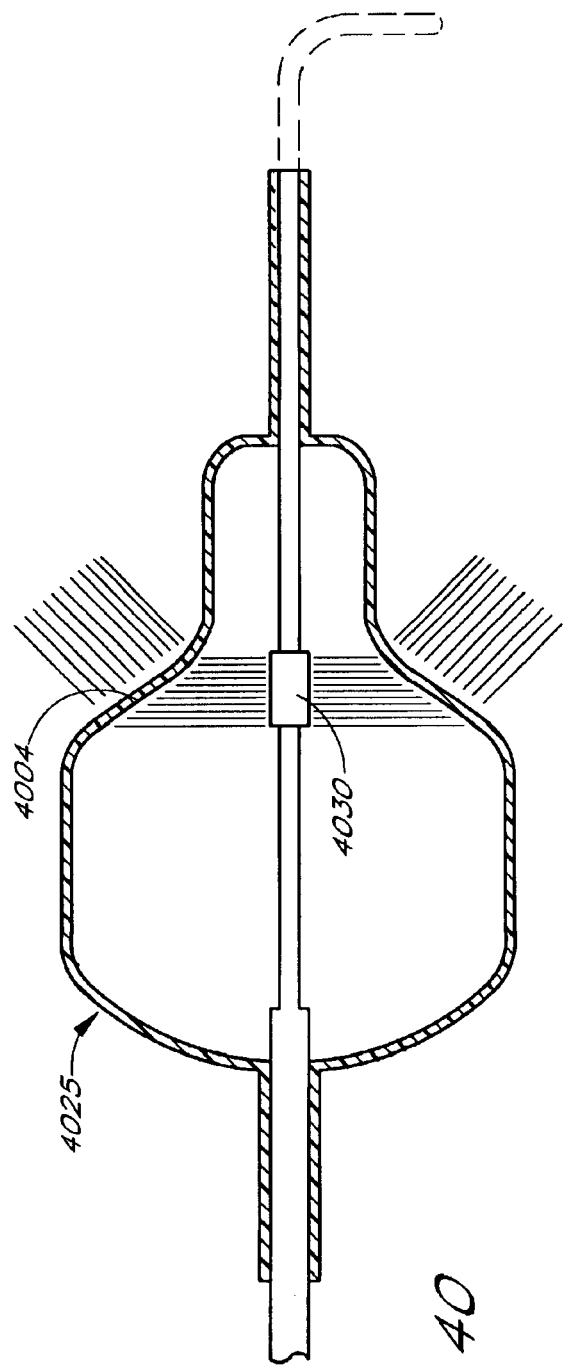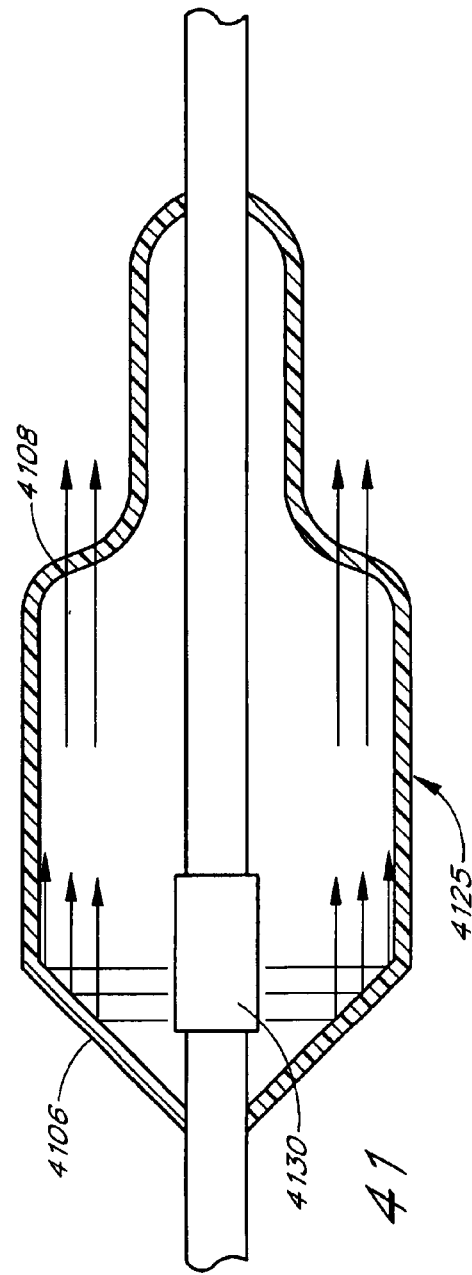

TISSUE ABLATION DEVICE ASSEMBLY AND METHOD OF ELECTRICALLY ISOLATING A PULMONARY VEIN OSTIUM FROM AN ATRIAL WALL

RELATED APPLICATIONS

This application is a divisional of U.S. patent application Ser. No. 09/435,281 filed on Nov. 5, 1999 now U.S. Pat. No. 6,652,515, to which this application claims priority under 35 U.S.C. § 121. U.S. patent application Ser. No. 09/435,281 is a continuation-in-part of U.S. patent application Ser. Nos. 08/889,798 filed on July 8, 1997, now U.S. Pat. No. 6,024,740; and Ser. No. 09/199,736 filed on Nov. 25, 1998, now U.S. Pat. No. 6,117,101, to which this application also claims priority under 35 U.S.C. § 120. This application also claims priority pursuant to 35 U.S.C. § 119(e) to provisional application No. 60/133,677 filed on May 11, 1999.

BACKGROUND OF THE INVENTION

1. Field of the Invention

The present invention relates to a surgical device and method. More specifically, it is a device assembly and method adapted to form a circumferential conduction block along a circumferential region of tissue along a posterior left atrial wall and surrounding a pulmonary vein.

2. Description of the Related Art

Many abnormal medical conditions in humans and other mammals have been associated with disease and other aberrations along the walls that define several different body spaces. In order to treat such abnormal wall conditions of the body spaces, medical device technologies adapted for delivering specific forms of ablative energy to specific regions of targeted wall tissue from within the associated body space have been developed and disclosed.

Cardiac arrhythmias, and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrhythmia, abnormal regions of cardiac tissue do not follow the synchronous beating cycle associated with normally conductive tissue in patients with sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmia, may be of a multiwavelet reentrant type, characterized by multiple asynchronous loops of electrical impulses that are scattered about the atrial chamber and are often self propagating. In the alternative or in addition to the multiwavelet reentrant type, cardiac arrhythmias may also have a focal origin, such as when an isolated region of tissue in an atrium fires autonomously in a rapid, repetitive fashion. These foci may act as either a trigger of paroxysmal atrial fibrillation or may sustain the fibrillation. Recent studies have suggested that focal arrhythmia often originates from a tissue region along the pulmonary veins of the left atrium, and even more particularly in the superior pulmonary veins.

Percutaneous catheter ablation techniques have been disclosed which use end-electrode catheter designs with the intention of ablating and thereby treating focal arrhythmias in the pulmonary veins. These ablation procedures are typically characterized by the incremental application of electrical energy to the tissue to form focal lesions designed to ablate the focus and thereby interrupt the inappropriate conduction pathways.

One example of a focal ablation method intended to destroy and thereby treat focal arrhythmia originating from a pulmonary vein is disclosed by Haissaguerre, et al. in "Right And Left Atrial Radiofrequency Catheter Therapy Of Paroxysmal Atrial Fibrillation" in *Journal of Cardiovascular Electrophysiology* 7(12), pp. 1132–1144 (1996). Haissaguerre, et al. disclose radiofrequency catheter ablation of drug-refractory paroxysmal atrial fibrillation using linear atrial lesions complemented by focal ablation targeted at arrhythmogenic foci in a screened patient population. The site of the arrhythmogenic foci were generally located just inside the superior pulmonary vein, and were ablated using a standard 4 mm tip single ablation electrode.

In another focal ablation example, Jais et al. in "A Focal Source Of Atrial Fibrillation Treated By Discrete Radiofrequency Ablation" *Circulation* 95:572–576 (1997), applies an ablative technique to patients with paroxysmal arrhythmias originating from a focal source. At the site of arrhythmogenic tissue, in both right and left atria, several pulses of a discrete source of radiofrequency energy were applied in order to eliminate the fibrillatory process.

There is a need, however, for a circumferential ablation device assembly and method adapted to electrically isolate a substantial portion of a posterior left atrial wall from an arrhythmogenic focus along a pulmonary vein. In particular there is still a need for such an assembly and method which provides a circumferential ablation member secured to the distal end of an elongate catheter body and which includes an ablation element adapted to form a circumferential conduction block along a circumferential region of tissue which either includes the arrhythmogenic focus or is between the arrhythmogenic focus and a substantial portion of the posterior left atrium wall.

SUMMARY OF THE INVENTION

This invention is a tissue ablation system and method that treats atrial arrhythmia by ablating a circumferential region of tissue at a location where a pulmonary vein extends from an atrium. In general, the system includes a circumferential ablation member with an ablation element that ablates the tissue at the location, and also includes a delivery assembly for delivering the ablation member to the location. The circumferential ablation member is generally adjustable between different configurations to allow for in one configuration the delivery through a delivery sheath into the atrium, and in another configuration the ablative coupling between the ablation element and the circumferential region of tissue at the location.

According to one mode of the tissue ablation system, the circumferential ablation member is adjustable to a position wherein a circumferential wall has a distal facing surface that surrounds the longitudinal axis of a cooperating delivery member. The ablation element ablatively couples to a circumferential area that is normal to the distal facing surface. The distal facing surface is configured such that the circumferential area coincides with the circumferential region of tissue when the wall is adjusted to the second position at the location, and therefore the ablatively coupled ablation element is adapted to ablate the circumferential region of tissue there.

According to another mode of the invention, a circumferential ablation member has a circumferential support member that is adjustable between a first position that is adapted to be delivered through a delivery sheath into the atrium and a second position having a substantially circumferentially looped shape. An ablation element is located substantially along the circumferential support member and is adapted to ablatively couple to a circumferential area adjacent to the support member in the second position. The looped shape of the circumferential support member is configured such that the circumferential area coincides with the circumferential region of tissue when the circumferential support member is adjusted to the second position at the location. A positioning assembly that is coupled to the circumferential support member such that the circumferential support member may be adjusted between the first and second positions when the circumferential support member is substantially radially unconfined within the atrium. In addition, a delivery assembly cooperates with the circumferential ablation member and is adapted to at least in-part deliver the circumferential ablation member to the location.

In one aspect of this mode, the circumferential support member has an elongate body that extends distally from a delivery member and is sufficiently straight in the first position to fit within a delivery sheath. The elongate body is reconfigured into the looped shape for ablation when the circumferential support member is adjusted to the second position.

In one variation of the system according to this aspect, the delivery member has a passageway extending between a distal port adjacent the proximal end of the elongate body and a proximal port located along the proximal end portion of the delivery member. The positioning assembly adjusts the position of the ablation member by use of a pull-wire that is moveably engaged within the passageway such that the proximal end portion of the pull-wire extends proximally through the proximal port, and the distal end portion of the pull-wire extends distally through the distal port where the pull-wire is secured to the distal end of the elongate body. In the first position the first and second ends of the elongate body are spaced along the pull-wire with the intermediate region of the elongate body extending along the longitudinal axis adjacent to the pull-wire. The circumferential support member is adjustable to the second position at least in part by adjusting the relative position of the pull-wire with respect to its moveable engagement within the passageway of the delivery member such that the proximal and distal ends of the elongate body are longitudinally collapsed toward each other. Such longitudinal repositioning of the ends of the elongate body cause the intermediate region to deflect radially into the desired looped shape.

According to a further feature of this variation, at least one indicator which indicates when the circumferential ablation member is in the second position, such as in one further variation by use of first and second radiopaque markers on the opposite ends of the elongate body, or by use of visible indicators on the proximal aspects that indicate the relative positioning of the pull-wire versus the delivery member.

In another aspect of this mode, the circumferential support member comprises an elongate body with a distal end secured to the distal end portion of the first delivery member and a proximal end secured to the distal end portion of the second delivery member. The positioning assembly comprises an outer member with a proximal end portion and a distal end portion that surrounds the distal end portions of the first and second delivery members and that has a longitudinal axis. The distal end portion of at least one of the delivery members is moveable along the outer member, such that in the first position the elongate body extends distally from the first delivery member substantially along the longitudinal axis, and in the second position the delivery members are longitudinally adjusted relative to each other and also relative to the outer member such that the elongate body is positioned externally of the distal end portion of the outer member with the elongate body adjusted into the substantially circumferentially looped shape.

According to various of the modes and more particular aspects herein summarized, one further variation provides an anchor along a distal end portion of a delivery member associated with the system and which is adapted to secure the delivery member within the pulmonary vein while the circumferential ablation member is being ablatively coupled to the circumferential region of tissue. In one more detailed example the anchor includes an expandable member that radially expands to engage the pulmonary vein in order to secure the delivery member in place during ablation.

In another aspect of this mode, the positioning assembly includes an array of circumferentially spaced splines that are positioned around the longitudinal axis. Each spline has a proximal end portion coupled to the distal end portion of the delivery member and a distal end portion coupled to the circumferential support member. Each spline is adjustable between a first configuration, wherein the distal end portion of the spline extends substantially along the longitudinal axis, and a second configuration, wherein the distal end portion of the spline extends radially away from the longitudinal axis. The first position for the circumferential support member according to this aspect is characterized at least in part by each of the splines being adjusted to the first configuration. The respective second position is characterized at least in part by each spline being adjusted to the second configuration.

According to one variation of the spline aspect of this mode, each spline provides a single elongate member that terminates distally where it is secured to the circumferential support member. In another variation, each spline provides a looped member having an apex along the distal end portion of the spline and two legs extending proximally from the apex along the proximal end portion of the spline. Further to this latter variation, the circumferential support member is threaded through the apexes of the circumferentially spaced splines. Moreover, according to a further feature at least one of the splines is used to help couple the ablation element to the ablation actuator, such as by allowing an ablation actuating member to extend along the spline to an energy source of the ablation element, and more specifically by providing fluid coupling along a passageway along the spline in the case of a fluid ablation element, or electrical coupling of electrical conductor leads along the spline passageway in the case of an electrical ablation element.

In another spline variations: the ablation element has a plurality of individual ablation elements, each extending along the circumferential support member between two adjacent splines; or, the splines comprises a material having a memory to the second configuration, such as by means of a shape memory material such as a nickel titanium alloy.

Further to other aspects of this mode, the ablation element may be one or more specific types of ablation elements, such as fluid, electrical, cryo, microwave, thermal, light-emitting, or ultrasound ablation elements.

In one specific variation incorporating the electrical ablation aspect of this mode, at least one electrode is provided along the circumferential support member that is adapted to be coupled to an electrical current source. A porous wall substantially surrounds the electrode within an enclosed fluid chamber that is adapted to be fluidly coupled to a source of electrically conductive fluid. The porous wall is further adapted to electrically couple an ablative electrical current between the circumferential region of tissue positioned coincident to the circumferential area and the electrode via the electrically conductive fluid.

According to another mode of the invention, a circumferential ablation member includes a housing, a mechanical positioning assembly that adjusts the housing between certain specific first and second conditions, and an ablation element also cooperating with the housing to ablate the circumferential region of tissue. Further to this mode, the housing is mechanically adjustable between a first condition and a second condition. In the first condition the distal wall is substantially radially collapsed such that the housing is adapted to be delivered through a delivery sheath into the atrium. In the second condition the distal wall is radially extended at least in part from the longitudinal axis with a distal orientation and a distal facing surface located along a circumferential region that surrounds the longitudinal axis. A mechanical positioning assembly is coupled to the housing to mechanically adjust the housing between the first and second conditions. An ablation element cooperates with the housing and is adapted to ablatively couple to a circumferential area normal to the distal facing surface along the circumferential region when the housing is in the second position. The distal facing surface is configured such that the circumferential area coincides with the circumferential region of tissue when the housing is adjusted to the second condition at the location, and therefore the ablation element is adapted to ablate the circumferential region of tissue in that position.

In one beneficial aspect of this mode, the distal wall in the second condition comprises a porous membrane that encloses at least in part a fluid chamber within the housing. The distal facing surface is located along the porous membrane, and the porous membrane is adapted to ablatively couple a volume of ablative fluid within the fluid chamber to the circumferential area. In one further regard, the porous membrane is adapted to allow the volume of ablative fluid to flow from within the fluid chamber and into the circumferential area. Still further, the ablation element may comprise a volume of ablative fluid medium within the fluid chamber and that ablatively couples with the circumferential area across the porous membrane. In a still further variation, the porous membrane is constructed at least in part from a porous tetrafluoropolymer. In another variation, the ablation element includes an ablative energy source located within the fluid chamber.

In another more detailed aspect of this mode, the housing has an outer jacket with a distal end portion and a proximal end portion, the distal wall is located along the distal end portion, and a proximal wall is located along the proximal end portion. The mechanical positioning assembly comprises an array of longitudinal splines that are circumferentially spaced around the longitudinal axis, wherein each of the longitudinal splines has a distal end portion and a proximal end portion and an intermediate region therebetween. The distal and proximal end portions of the outer jacket are positioned to surround at least a part of the proximal and distal end portions of the splines, respectively. According to this relationship, in the first condition the proximal and distal end portions of each spline are respectively spaced along the longitudinal axis with the intermediate region being substantially radially collapsed within the outer jacket. The housing is adjusted to the second condition by longitudinally collapsing the relative position of the proximal and distal end portions of each spline such that the intermediate region of each spline and outer jacket adjacent thereto deflects radially outwardly from the longitudinal axis such that distal and proximal orientations, respectively, are given to the distal and proximal walls. In one variation of this aspect, the outer jacket comprises an elastomeric material.

In another aspect of this mode the housing also has a proximal wall that in the second condition has a proximally facing surface. The proximal wall according to this aspect is connected to the distal wall, such as in a still further variation by being formed from an integral member. In a still more detailed variation however, the distal and proximal walls are connected along at least one of (a) an outer circumferential region that circumscribes the circumferential region that includes the distal facing surface, or (b) an inner circumferential region that is circumscribed by the circumferential region that includes the distal facing surface. In yet another variation, the mechanical positioning assembly provides at least one support member extending between the distal and proximal walls at least across an inner circumferential region, which is circumscribed by the circumferential region that includes the distal facing surface, and the circumferential region with that distal facing surface.

According to another aspect of the mechanically adjustable ablative housing mode, the mechanical positioning assembly is coupled to the delivery member.

In another more detailed aspect of this mode, the mechanical positioning assembly comprises an array of splines that are circumferentially spaced around the longitudinal axis of the delivery member. Each spline has a distal end portion coupled to the distally oriented wall and a proximal end portion coupled to the distal end portion of the delivery member. Also, each spline is adjustable between a first position, which is substantially radially collapsed and extending along the longitudinal axis, and a second position wherein the distal end portion of the spline extends radially outwardly from the longitudinal axis. Accordingly, the first and second positions for the splines characterize at least in part the first and second conditions for the housing.

Further to this aspect, in one variation the ablation element comprises an energy source that is located along a spline at a position corresponding to the circumferential region.

According to another mode of the invention, a circumferential ablation member coupled to the distal end portion of a delivery member includes an array of splines supporting an array of individual ablation elements with each ablation element being supported along a support region of one of the splines. The splines are circumferentially spaced around the longitudinal axis. Each spline is adjustable between a first condition and a second condition, wherein the respectively supported individual ablation element is adjustable between a first radial position and a second radial position. Further to this assembly, each spline is substantially radially collapsed and extends substantially along the longitudinal axis in the first condition such that the circumferential ablation member is adapted to be delivered through a delivery sheath into the atrium. In the second condition, the support region of each spline extends at least in part radially away from the longitudinal axis. Each of the individual ablation elements is thus held by the supporting spline in the second radial position with the array of individual ablation elements being spaced along a circumferential pattern that surrounds the longitudinal axis. This circumferential pattern is specifically configured such that the array of individual ablation elements is adapted to engage and ablate the circumferential region of tissue when the splines are adjusted to the second condition at the location.

In one aspect of this mode, each of the splines has a memory to the second condition, such as by being constructed from a shape-memory material that more specifically may be a nickel-titanium alloy.

In another aspect, an outer member surrounds the distal end portion of the delivery member. The splines are adapted to be moved in and out of the outer member in order to adjust their shape between the first and second positions.

According to additional aspects of this mode, the distal end portion of each of the splines in the second position may have a radius of curvature either away from the longitudinal axis, or in another aspect the radius of curvature may be toward the longitudinal axis.

According to still further aspects of this mode, the ablation element may be one of a number of different types, including one or more of the following: an electrical current ablation element; a thermal ablation element; an ultrasound ablation element; a microwave ablation element; a thermal ablation element; a cryoablation element; a fluid ablation element; or a light emitting ablation element.

In another mode, the invention provides a contact member in combination with a distally oriented ablation element, both being coupled to a delivery member. The contact member is adjustable between a first condition for delivery through a delivery sheath into the atrium and a second condition for circumferential ablation wherein the contact member comprises a circumferential wall that surrounds the longitudinal axis. The ablation element has an ablative energy source that is located along the distal end portion of the delivery member, and cooperates with the contact member such that the ablative energy source emits a circumferential pattern of energy having a distal orientation through the circumferential wall and into a circumferential area normal to the circumferential wall. Electrical current is not ablatively coupled between the ablative energy source and the circumferential area according to this mode. The ablation element and contact member are configured such that the circumferential area coincides with the circumferential region of tissue when the contact member is adjusted to the second condition at the location.

In one aspect of this mode, the contact member is an inflatable balloon and the ablation element cooperates with the circumferential area as described above through the balloon's outer skin.

According to still further aspects of this mode, the ablation element may be one of a number of different types, including one or more of the following: an electrical current ablation element; a thermal ablation element; an ultrasound ablation element; a microwave ablation element; a thermal ablation element; a cryoablation element; a fluid ablation element; or a light emitting ablation element.

In one variation of the ultrasound ablation element aspect, an ultrasound transducer assembly is mounted onto the distal end portion with a distally oriented face that is adapted to emit an ultrasonic energy signal distally at an angle relative to the longitudinal axis and through the circumferential wall of the contact member. In still a further more detailed variation, the transducer is conically shaped with an outer conical surface having a distal orientation. In another detailed variation the transducer has a curved distal face.

In still a further detailed variation, the ultrasound transducer assembly has at least one ultrasound transducer panel that is adjustable from a radially collapsed position to a radially extended position having a distally oriented face that is adapted to emit the circumferential pattern of energy with the distal orientation. Further to this transducer panel variation, the transducer panel may be adjustable as described by use of an expandable member located between the panel and the distal end portion of the delivery member, which expandable member may be a balloon structure or a cage structure.

Other modes, aspects, variations, and features of the invention shall become apparent to one of ordinary skill upon review of this application, and in particular by reference to the detailed disclosure of the invention which follows below.

BRIEF DESCRIPTION OF THE DRAWINGS

FIGS. 2A–E show schematic, perspective views of various exemplary circumferential conduction blocks formed at a location where a pulmonary vein extends from an atrium with a circumferential ablation device assembly.

FIGS. 8A–B show perspective views of another circumferential ablation catheter during use in a left atrium according to the method of FIG. 3, wherein FIG. 8A shows a radially compliant expandable member with a working length adjusted to a radially expanded position while in the left atrium, and FIG. 8B shows the expandable member after advancing it into and engaging a pulmonary vein ostium while in the radially expanded position.

FIG. 8D shows another circumferential ablation catheter during use in a left atrium, and shows an expandable member in a radially expanded position which is engaged within a pulmonary vein ostium such that a circumferential band of a circumferential ablation element circumscribing the expandable member is also engaged to a circumferential path of tissue along the left posterior atrial wall which surrounds the pulmonary vein ostium.

FIG. 8E shows one particular expandable member and circumferential ablation element that is adapted for use according to the mode of use shown in FIG. 8D.

FIGS. 11A–B show perspective views of one circumferential ablation member for use in a circumferential ablation device assembly, showing a circumferential ablation electrode circumscribing the working length of an expandable member with a secondary shape along the longitudinal axis of the working length which is a modified step shape, the expandable member being shown in a radially collapsed position and also in a radially expanded position, respectively.

FIGS. 11C–D show perspective views of two circumferential ablation electrodes which form equatorial or otherwise circumferentially placed bands that circumscribe the working length of an expandable member and that have serpentine and sawtooth secondary shapes, respectively, relative to the longitudinal axis of the expandable member when adjusted to a radially expanded position.

FIGS. 12A–B show perspective views of another circumferential ablation element which includes a plurality of individual ablation electrodes that are spaced circumferentially to form an equatorial band which circumscribes the working length of an expandable member either in an equatorial location or an otherwise circumferential location that is bounded both proximally and distally by the working length, and which are adapted to form a continuous circumferential lesion while the working length is adjusted to a radially expanded position.

FIG. 18 shows a perspective overview of another circumferential ablation device assembly having a circumferential ablation member with a plurality of individual ablation elements disposed along splines of a braided cage that is adjusted to a radially expanded condition.

FIG. 19A shows a perspective overview of another circumferential ablation device assembly having a circumferential ablation member with a plurality of individual ablation elements in a first position along a plurality of spline members that are in a radially collapsed condition with a longitudinal orientation relative to the shaft of an elongated catheter body of the assembly.

FIG. 19B shows a perspective overview of the circumferential ablation device assembly shown in 19A, and shows a mid portion of each of the plurality of spline members radially outwardly deflected with the individual ablation elements in a second position which is adapted to form the circumferential ablation element according to the invention.

FIG. 20B shows an end view of the circumferential ablation device assembly taken along lines 20B—20B shown in FIG. 20A, and shows an ablation member having a plurality of individual ablation elements that form an assembly of bipolar electrodes which are positioned by the spline members along a circumferential pattern having a radius R.

FIG. 20C shows a transverse cross-sectional view taken along line 20C—20C of FIG. 20A.

FIGS. 21A–C show side perspective, end, and exploded side perspective views, respectively, of a similar assembly as shown in FIG. 19A, although showing a higher number of ablation elements and associated spline members that are further shown having a different arcuate shape than is shown in the FIG. 19A embodiment.

FIG. 22A shows a circumferential ablation device assembly with a delivery sheath and spline combination which is similar to that shown in FIG. 20A, although showing a plurality of elongate ablation elements extending between the distal ends of the shaped spline members in order to form a circumferential pattern adapted to ablate a circumferential region of tissue according to the invention.

FIG. 22B shows an end view of the assembly taken along line 22B—22B shown in FIG. 22A.

FIG. 24A shows a perspective overview of another circumferential ablation device assembly similar to that shown in FIG. 22A, although showing the circumferential ablation element engaged by and extending between the splines that are radially extended to position the circumferential ablation element in order to form a circumferential lesion according to the invention.

FIG. 24B shows a perspective overview of the assembly shown in FIG. 24A, although showing the shaped splines partially coaxially confined within a delivery sheath such that the circumferential ablation element is adjusted to a shape which is adapted for delivery to and from the left atrium through the delivery sheath.

FIG. 24C shows an exploded perspective view of one embodiment for coupling a spline member to the circumferentially shaped member supporting individual ablation elements to form the circumferential ablation member according to a similar assembly such as that shown in FIG. 24A.

FIG. 24D shows an exploded perspective view of another embodiment for the circumferential ablation element to that shown in FIG. 24C and shows a porous membrane over an arcuate shaped support member that is adapted to extend between splines

FIGS. 25A–B show a perspective schematic views of another circumferential ablation device assembly having a plurality of spline members that are rotatably engaged in first and second positions, respectively, relative to a circumferential ablation element according to the invention.

FIG. 25C shows a perspective overview of another circumferential ablation device assembly which is similar to that shown in FIGS. 25A–B, but showing spline members that are shaped with a curved geometry adjacent to where they are engaged to the circumferential ablation element.

FIG. 25D shows a partially shadowed exploded view of a flexible "T"-shaped coupler which couples the spline member and opposing ends of two curved ablation elements that form in part the circumferential ablation element, in addition to fluid tubing and porous members variously corresponding to those structures.

FIG. 25E shows a partially exploded view of further detail of the coupling of FIG. 25D, further showing how the fluid tubing and spline member of that assembly couple proximally with a catheter body for remote delivery and ablation according to the invention.

FIG. 26A shows an end perspective view of another circumferential ablation device assembly which is similar to that shown in FIGS. 22A and 24A, although showing spline members having shapes that include complex arcuate looped structures.

FIG. 26B shows a perspective overview of the same assembly shown in FIG. 26A and shows the complex, arcuate shaped spline members partially withdrawn into a delivery sheath and radially collapsed in a substantially longitudinal orientation relative to the delivery sheath such that the circumferential ablation element is shaped in a partially collapsed condition adapted for delivery to and from the left atrium through the delivery sheath.

FIG. 26C shows an exploded side view of the same assembly shown in FIG. 26B, and shows a portion of the circumferential ablation element threaded through a loop of a spline member in order to couple the circumferential ablation element to the spline member.

FIG. 29A shows a cross-sectioned longitudinal view of another circumferential ablation device assembly.

FIG. 29B shows an enlarged cross-sectioned view of the distal portion of the ablation device assembly of FIG. 29A.

FIG. 30A shows a partially sectioned longitudinal side view of another circumferential ablation member for use in a circumferential ablation device assembly according to the present invention.

FIG. 30B shows a proximal end perspective view of the circumferential ablation member shown in FIG. 30A, showing the splines in phantom.

FIG. 30C shows a distal end perspective view of the circumferential ablation member shown in FIG. 30A.

FIG. 30D shows a sectioned view of one catheter shaft assembly for use in a circumferential ablation device assembly incorporating the circumferential ablation member shown in FIGS. 30A–30C, and shows the cooperation of coaxially disposed tubing members in the shaft assembly which allow for the circumferential ablation element to be adjusted between a radially collapsed position and a radially expanded position.

FIG. 31A shows a longitudinal cross-sectional view of another circumferential ablation catheter with an ablation element having a single cylindrical ultrasound transducer which is positioned along an inner member within an expandable balloon which is further shown in a radially expanded condition.

FIG. 31B shows a transverse cross-sectional view of the circumferential ablation catheter shown in FIG. 31A taken along line 31B—31B shown in FIG. 31A.

FIG. 31C shows a transverse cross-sectional view of the circumferential ablation catheter shown in FIG. 31A taken along line 31C—31C shown in FIG. 31A.

FIG. 31D shows a perspective view of the ultrasonic transducer of FIG. 31A in isolation.

FIG. 31E shows a modified version of the ultrasonic transducer of FIG. 31D with individually driven sectors.

FIG. 34A shows a transverse cross-sectional view of an additional circumferential ablation catheter with an ablation element having a single transducer sector segment which is positioned along an inner member within an expandable balloon which is further shown in a radially expanded condition.

FIG. 34B shows a transverse cross-sectional view of a further circumferential ablation catheter with an ablation element having a single curvilinear section that is mounted so as to position its concave surface facing in a radially outward direction.

FIG. 36A shows a schematic perspective view of another ablation element which is adapted to be used in a circumferential ablation member such as shown in FIG. 35A, and shows a plurality of circumferentially spaced, radially adjustable ultrasound panels having an arcuate shape.

FIG. 36B shows a longitudinal side view of the ablation element shown in FIG. 36A.

FIG. 36C shows an end view taken from a rearward perspective of the ablation element along line 36C—36C shown in FIG. 36A.

FIG. 37A shows a schematic perspective view of a similar ablation element as that shown in FIG. 36A, except showing the ultrasound panels having generally flat planar shapes.

FIG. 37B shows a longitudinal side view of the ablation element shown in FIG. 37A.

FIG. 37C shows an end view taken along line 37C—37C of FIG. 37B.

FIGS. 38A–B respectively show various actuating members for adjusting the ultrasound transducer panels such as those shown in FIGS. 37A–C to a radially extended position relative to an interior support shaft which is adapted to ablate a circumferential region of tissue according to FIG. 35A.

FIG. 40 shows a schematic longitudinal side view of another circumferential ablation member for use in ablating a circumferential region of tissue such as according to FIG. 35A, wherein deflecting surfaces along the tapered distal surfaces of the balloon are employed to aim the ultrasound energy toward the circumferential region of tissue.

FIG. 41 shows a schematic longitudinal side view of another circumferential ablation member for use in ablating a circumferential region of tissue such as according to FIG. 35A, wherein deflecting surfaces along the proximal taper of the balloon are employed to aim the ultrasound energy toward the circumferential region of tissue.

DETAILED DESCRIPTION OF THE PREFERRED EMBODIMENT

Figure 1:
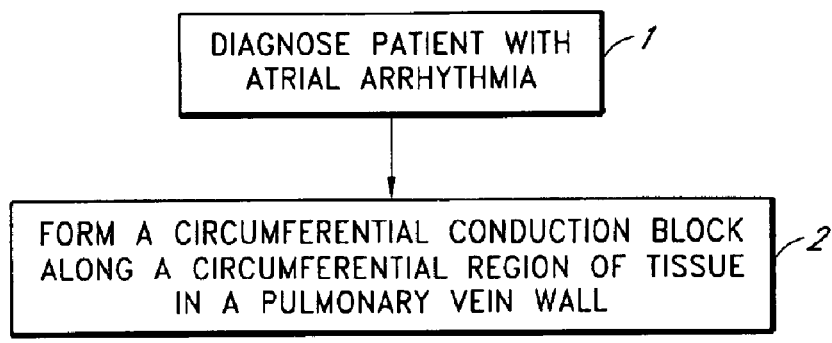
FIG. 1 diagrammatically shows sequential, general steps of a method for treating atrial arrhythmia.

The terms "body space," including derivatives thereof, is herein intended to mean any cavity or lumen within the body that is defined at least in part by a tissue wall. For example, the cardiac chambers, the uterus, the regions of the gastrointestinal tract, and the arterial or venous vessels are all considered illustrative examples of body spaces within the intended meaning.

The term "lumen," including derivatives thereof, is herein intended to mean any body space which is circumscribed along a length by a tubular tissue wall and which terminates at each of two ends in at least one opening that communicates externally of the body space. For example, the large and small intestines, the vas deferens, the trachea, and the fallopian tubes are all illustrative examples of lumens within the intended meaning. Blood vessels are also herein considered lumens, including regions of the vascular tree between their branch points. More particularly, the pulmonary veins are lumens within the intended meaning, including the region of the pulmonary veins between the branched portions of their ostia along a left ventricle wall, although the wall tissue defining the ostia typically presents uniquely tapered lumenal shapes.

The following disclosure referring to FIGS. 1–15 describe various circumferential ablation device assemblies which are adapted to treat patients with atrial arrhythmia by forming a circumferential conduction block at a location where a pulmonary vein extends from an atrium which blocks electrical conduction propagating from cardiac tissue along a pulmonary vein wall and into the left atrium. The related method of treatment is further illustrated in diagrammatically form in the flow diagram of FIG. 1.

The terms "circumference" or "circumferential", including derivatives thereof, are herein intended to mean a continuous path or line that forms an outer border or perimeter that surrounds and thereby defines an enclosed region of space. Such a continuous path starts at one location along the outer border or perimeter, and translates along the outer border or perimeter until it is completed at the original starting location to enclose the defined region of space. The related term "circumscribe," including derivatives thereof, is herein intended to mean to enclose, surround, or encompass a defined region of space. Therefore, according to these defined terms, a continuous line which is traced around a region of space and which starts and ends at the same location "circumscribes" the region of space and has a "circumference" which is defined by the distance the line travels as it translates along the path circumscribing the space.

Still further, a circumferential path or element may include one or more of several shapes, and may be, for example, circular, oblong, ovular, elliptical, or otherwise planar enclosures. A circumferential path may also be three dimensional, such as, for example, two opposite-facing semi-circular paths in two different parallel or off-axis planes that are connected at their ends by line segments bridging between the planes.

For purpose of further illustration, FIGS. 2A–D therefore show various circumferential paths A, B, C, and D, respectively, each translating along a portion of a pulmonary vein wall and circumscribing a defined region of space, shown at a, b, c, and d also respectively, each circumscribed region of space being a portion of a pulmonary vein lumen. For still further illustration of the three-dimensional circumferential case shown in FIG. 2D, FIG. 2E shows an exploded perspective view of circumferential path D as it circumscribes multiplanar portions of the pulmonary vein lumen shown at d', d", and d'", which together make up region d as shown in FIG. 2D.

The term "transect", including derivatives thereof, is also herein intended to mean to divide or separate a region of space into isolated regions. Thus, each of the regions circumscribed by the circumferential paths shown in FIGS. 2A–D transects the respective pulmonary vein, including its lumen and its wall, to the extent that the respective pulmonary vein is divided into a first longitudinal region located on one side of the transecting region, shown, for example, at region "X" in FIG. 2A, and a second longitudinal region on the other side of the transecting plane, shown, for example, at region "Y" also in FIG. 2A.

Therefore, a "circumferential conduction block" according to the present invention is formed along a region of tissue that follows a circumferential path along the pulmonary vein wall, circumscribing the pulmonary vein lumen and transecting the pulmonary vein relative to electrical conduction along its longitudinal axis. The transecting circumferential conduction block therefore isolates electrical conduction between opposite longitudinal portions of the pulmonary wall relative to the conduction block and along the longitudinal axis.

The terms "ablate" or "ablation," including derivatives thereof, are hereafter intended to mean the substantial altering of the mechanical, electrical, chemical, or other structural nature of tissue. In the context of intracardiac ablation applications shown and described with reference to the variations of the illustrative embodiment below, "ablation" is intended to mean sufficient altering of tissue properties to substantially block conduction of electrical signals from or through the ablated cardiac tissue.

The term "element" within the context of "ablation element" is herein intended to mean a discrete element, such as an electrode, or a plurality of discrete elements, such as a plurality of spaced electrodes, which are positioned so as to collectively ablate a region of tissue.

Therefore, an "ablation element" according to the defined terms may include a variety of specific structures adapted to ablate a defined region of tissue. For example, one suitable ablation element for use in the present invention may be formed, according to the teachings of the embodiments below, from an "energy emitting" type that is adapted to emit energy sufficient to ablate tissue when coupled to and energized by an energy source. Suitable "energy emitting" ablation elements for use in the present invention may therefore include, for example: an electrode element adapted to couple to a direct current ("DC") or alternating current ("AC") current source, such as a radiofrequency ("RF") current source; an antenna element which is energized by a microwave energy source; a heating element, such as a metallic element or other thermal conductor which is energized to emit heat such as by convective or conductive heat transfer, by resistive heating due to current flow, or by optical heating with light; a light emitting element, such as a fiber optic element which transmits light sufficient to ablate tissue when coupled to a light source; or an ultrasonic element such as an ultrasound crystal element which is adapted to emit ultrasonic sound waves sufficient to ablate tissue when coupled to a suitable excitation source.

In addition, other elements for altering the nature of tissue may be suitable as "ablation elements" under the present invention when adapted according to the detailed description of the invention below. For example, a cryoablation element adapted to sufficiently cool tissue to substantially alter the structure thereof may be suitable if adapted according to the teachings of the current invention. Furthermore, a fluid delivery element, such as a discrete port or a plurality of ports that are fluidly coupled to a fluid delivery source, may be adapted to infuse an ablating fluid, such as a fluid containing alcohol, into the tissue adjacent to the port or ports to substantially alter the nature of that tissue.

The term "anchor" is herein intended to broadly encompass any structure that functions to secure at least a portion of the disclosed ablation device assemblies to a pulmonary vein or pulmonary vein ostium, such that the circumferential and/or linear ablation elements are positioned sufficiently close to posterior wall of the left atrium to ablatively engage the targeted tissue. Examples of suitable anchors within the scope of the present disclosure include, conventional guidewires, guidewires with balloons, deflectable/steerable guidewires, shaped stylets, radially expandable members, inflatable members, etc.

The term "diagnose", including derivatives thereof, is intended to include patients suspected or predicted to have atrial arrhythmia, in addition to those having specific symptoms or mapped electrical conduction indicative of atrial arrhythmia.

Returning to the inventive method as shown in FIG. 1, a patient diagnosed with atrial arrhythmia according to diagnosing step (1) is treated with a circumferential conduction block according to treatment step (2). In one aspect, a patient diagnosed according to diagnosis step (1) with multiple wavelet arrhythmia originating from multiple regions along the atrial wall may also be treated in part by forming the circumferential conduction block according to treatment step (2), although as an adjunct to forming long linear regions of conduction block between adjacent pulmonary vein ostia in a less-invasive "maze"-type catheter ablation procedure. More detail regarding this particular aspect of the inventive method is provided below with reference to a combination circumferential-long linear lesion ablation device that is described below with reference to FIGS. 9A–F.

In another aspect of the method of FIG. 1, a patient diagnosed with focal arrhythmia originating from an arrhythmogenic origin or focus in a pulmonary vein is treated according to this method when the circumferential conduction block is formed along a circumferential path of wall tissue that either includes the arrhythmogenic origin or is between the origin and the left atrium. In the former case, the arrhythmogenic tissue at the origin is destroyed by the conduction block as it is formed through that focus. In the latter case, the arrhythmogenic focus may still conduct abnormally, although such aberrant conduction is prevented from entering and affecting the atrial wall tissue due to the intervening circumferential conduction block.

In still a further aspect of the method shown in FIG. 1, the circumferential conduction block may be formed in one of several ways according to treatment step (2). In one example not shown, the circumferential conduction block may be formed by a surgical incision or other method to mechanically transect the pulmonary vein, followed by suturing the transected vein back together. As the circumferential injury is naturally repaired, such as through a physiologic scarring response common to the "maze" procedure, electrical conduction will generally not be restored across the injury site. In another example not shown, a circumferential conduction block of one or more pulmonary veins may be performed in an epicardial ablation procedure, wherein an ablation element is either placed around the target pulmonary vein or is translated circumferentially around it while being energized to ablate the adjacent tissue in an "outside-in" approach. This alternative method may be performed during an open chest-type procedure, or may be done using other known epicardial access techniques.

Figure 3:
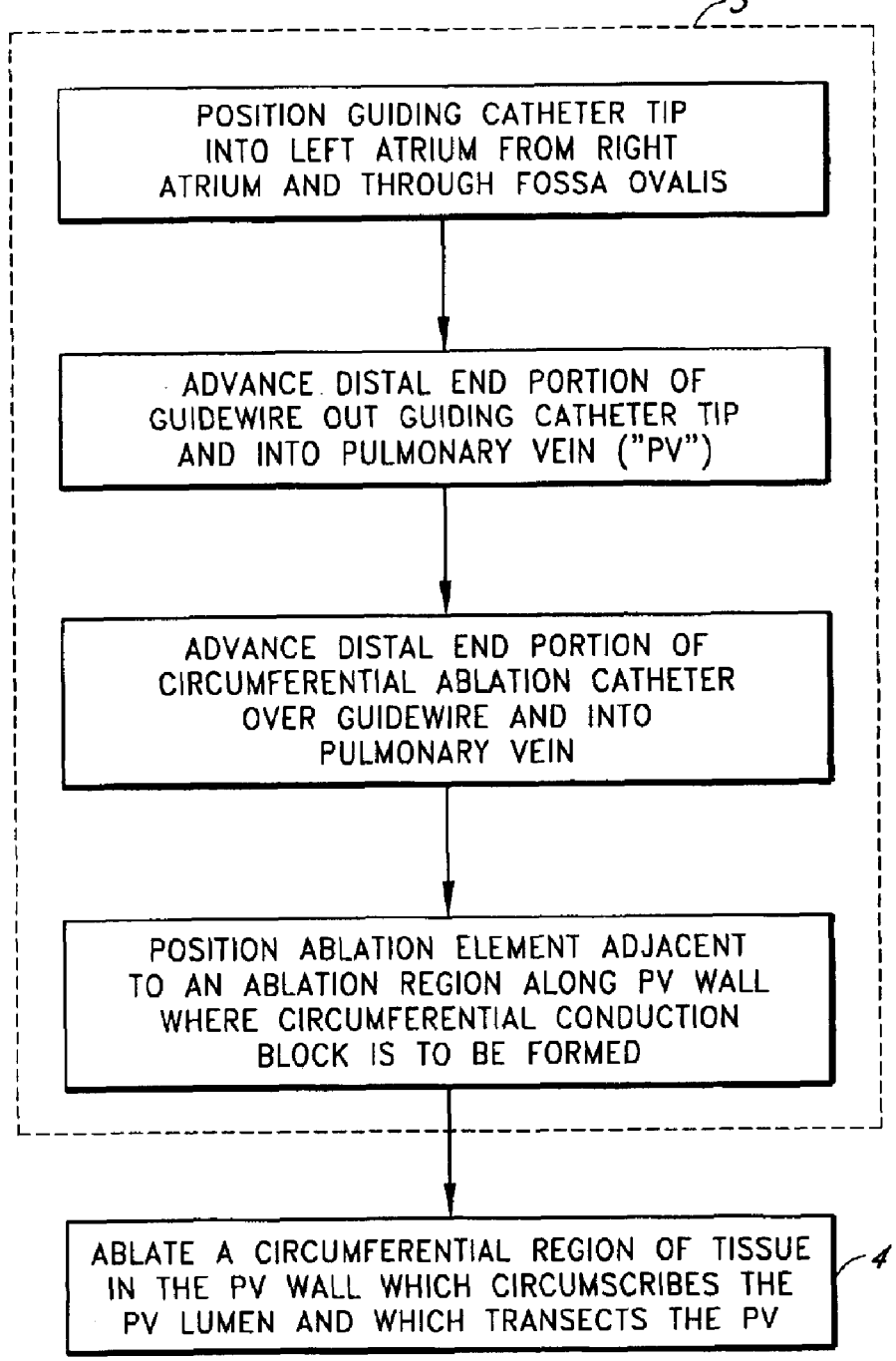
FIG. 3 shows a flow diagram of a method for using a circumferential ablation device assembly to form a circumferential conduction block at a location where a pulmonary vein extends from an atrium.

FIG. 3 diagrammatically shows the sequential steps of a method for using the circumferential ablation device assembly of the present invention in forming a circumferential conduction block at a location where a pulmonary vein extends from an atrium. The circumferential ablation method according to FIG. 3 includes: positioning a circumferential ablation element at an ablation region along the pulmonary vein according to a series of detailed steps shown collectively in FIG. 3 as positioning step (3); and thereafter ablating a continuous circumferential region of tissue in the PV wall at the ablation region according to ablation step (4).

Further to positioning step (3) according to the method of FIG. 3, a distal tip of a guiding catheter is first positioned within the left atrium according to a transeptal access method, which is further described in more detail as follows. The right venous system is first accessed using the "Seldinger" technique, wherein a peripheral vein (such as a femoral vein) is punctured with a needle, the puncture wound is dilated with a dilator to a size sufficient to accommodate an introducer sheath, and an introducer sheath with at least one hemostatic valve is seated within the dilated puncture wound while maintaining relative hemostasis. With the introducer sheath in place, the guiding catheter or sheath is introduced through the hemostatic valve of the introducer sheath and is advanced along the peripheral vein, into the region of the vena cavae, and into the right atrium.

Once in the right atrium, the distal tip of the guiding catheter is positioned against the fossa ovalis in the intraatrial septal wall. A "Brockenbrough" needle or trocar is then advanced distally through the guide catheter until it punctures the fossa ovalis. A separate dilator may also be advanced with the needle through the fossa ovalis to prepare an access port through the septum for seating the guiding catheter. The guiding catheter thereafter replaces the needle across the septum and is seated in the left atrium through the fossa ovalis, thereby providing access for object devices through its own inner lumen and into the left atrium.

It is however further contemplated that other left atrial access methods may be suitable substitutes for using the circumferential ablation device assembly of the present invention. In one alternative variation not shown, a "retrograde" approach may be used, wherein the guiding catheter is advanced into the left atrium from the arterial system. In this variation, the Seldinger technique is employed to gain vascular access into the arterial system, rather than the venous, for example, at a femoral artery. The guiding catheter is advanced retrogradedly through the aorta, around the aortic arch, into the ventricle, and then into the left atrium through the mitral valve.

Subsequent to gaining transeptal access to the left atrium as just described, positioning step (3) according to FIG. 3 next includes advancing a guidewire into a pulmonary vein, which is done generally through the guiding catheter seated in the fossa ovalis. In addition to the left atrial access guiding catheter, the guidewire according to this variation may also be advanced into the pulmonary vein by directing it into the vein with a second sub-selective delivery catheter (not shown) which is coaxial within the guiding catheter, such as, for example, by using one of the directional catheters disclosed in U.S. Pat. No. 5,575,766 to Swartz. Or, the guidewire may have sufficient stiffness and maneuverability in the left atrial cavity to unitarily subselect the desired pulmonary vein distally of the guiding catheter seated at the fossa ovalis.

Suitable guidewire designs for use in the overall circumferential ablation device assembly of the present invention may be selected from previously known designs, while generally any suitable choice should include a shaped, radiopaque distal end portion with a relatively stiff, torquable proximal portion adapted to steer the shaped tip under X-ray visualization. Guidewires having an outer diameter ranging from 0.010 inch to 0.035 inch may be suitable. In cases where the guidewire is used to bridge the atrium from the guiding catheter at the fossa ovalis, and where no other sub-selective guiding catheters are used, guidewires having an outer diameter ranging from 0.018 inch to 0.035 inch may be required. It is believed that guidewires within this size range may be required to provide sufficient stiffness and maneuverability in order to allow for guidewire control and to prevent undesirable guidewire prolapsing within'the relatively open atrial cavity.

Subsequent to gaining pulmonary vein access, positioning step (3) of FIG. 3 next includes tracking the distal end portion of a circumferential ablation device assembly over the guidewire and into the pulmonary vein, followed by positioning a circumferential ablation element at an ablation region of the pulmonary vein where the circumferential conduction block is to be desirably formed.

Figure 4:
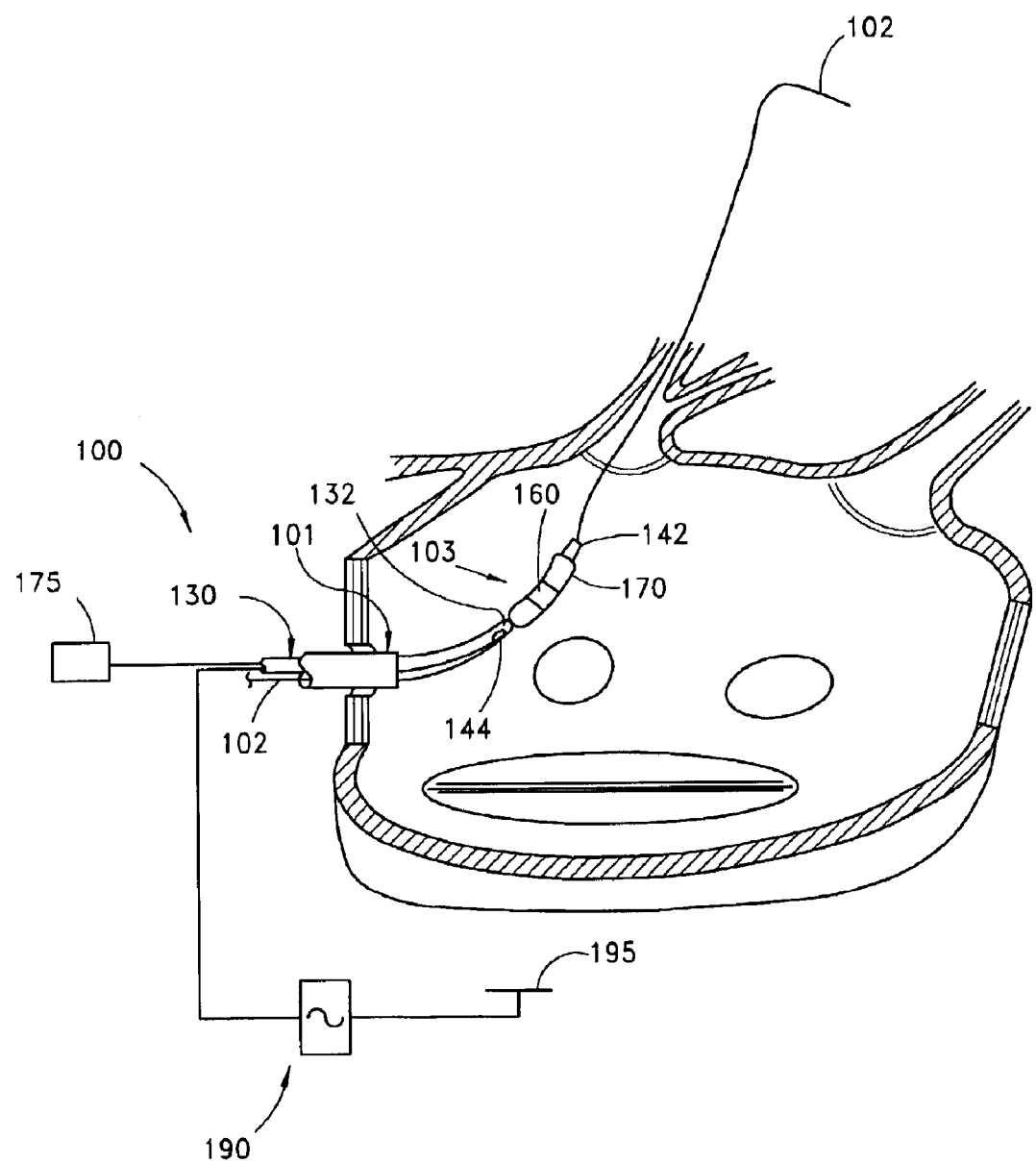
FIG. 4 shows a perspective view of a circumferential ablation device assembly during use in a left atrium subsequent to performing transeptal access and guidewire positioning steps according to the method of FIG. 3.

FIG. 4 further shows a circumferential ablation device assembly 100 according to the present invention during use in performing positioning step (3) and ablation step (4) just described with reference to FIG. 3. Included in the circumferential ablation device assembly 100 are guiding catheter 101, guidewire 102, and circumferential ablation catheter 103.

More specifically, FIG. 4 shows guiding catheter 101 subsequent to performing a transeptal access method according to FIG. 3, and also shows guidewire 102 subsequent to advancement and positioning within a pulmonary vein, also according to step (3) of FIG. 3. FIG. 4 shows circumferential ablation catheter 103 as it tracks coaxially over guidewire 102 with a distal guidewire tracking member, which is specifically shown only in part at first and second distal guidewire ports 142,144 located on the distal end portion 132 of an elongate catheter body 130. A guidewire lumen (not shown) extends between the first and second distal guidewire ports 142,144 and is adapted to slideably receive and track over the guidewire. In the particular variation of FIG. 4, the second distal guidewire port 142 is located on a distal end portion 132 of the elongate catheter body 130, although proximally of first distal guidewire port 142.

As would be apparent to one of ordinary skill, the distal guidewire tracking member shown in FIG. 4 and just described may be slideably coupled to the guidewire externally of the body in a "backloading" technique after the guidewire is first positioned in the pulmonary vein. Furthermore, there is no need in this guidewire tracking variation for a guidewire lumen in the proximal portions of the elongate catheter body 130, which allows for a reduction in the outer diameter of the catheter shaft in that region. Nevertheless, it is further contemplated that a design which places the second distal guidewire port on the proximal end portion of the elongate catheter body would also be acceptable, as is described below, for example, with reference to the perfusion embodiment of FIGS. 6A–B.

In addition, the inclusion of a guidewire lumen extending within the elongate catheter body between first and second ports, as provided in FIG. 4, should not limit the scope of acceptable guidewire tracking members according to the present invention. Other guidewire tracking members which form a bore adapted to slideably receive and track over a guidewire are also considered acceptable, such as, for example, the structure adapted to engage a guidewire as described in U.S. Pat. No. 5,505,702 to Arney, the entirety of which is hereby incorporated by reference herein.

While the assemblies and methods shown variously throughout the Fig.'s include a guidewire coupled to a guidewire tracking member on the circumferential ablation catheter, other detailed variations may also be suitable for positioning the circumferential ablation element at the ablation region in order to form a circumferential conduction block there. For example, an alternative circumferential ablation catheter not shown may include a "fixed-wire"-type of design wherein a guidewire is integrated into the ablation catheter as one unit. In another alternative assembly, the same type of sub-selective sheaths described above with reference to U.S. Pat. No. 5,575,766 to Swartz for advancing a guidewire into a pulmonary vein may also be used for advancing a circumferential ablation catheter device across the atrium and into a pulmonary vein.

Figure 5:
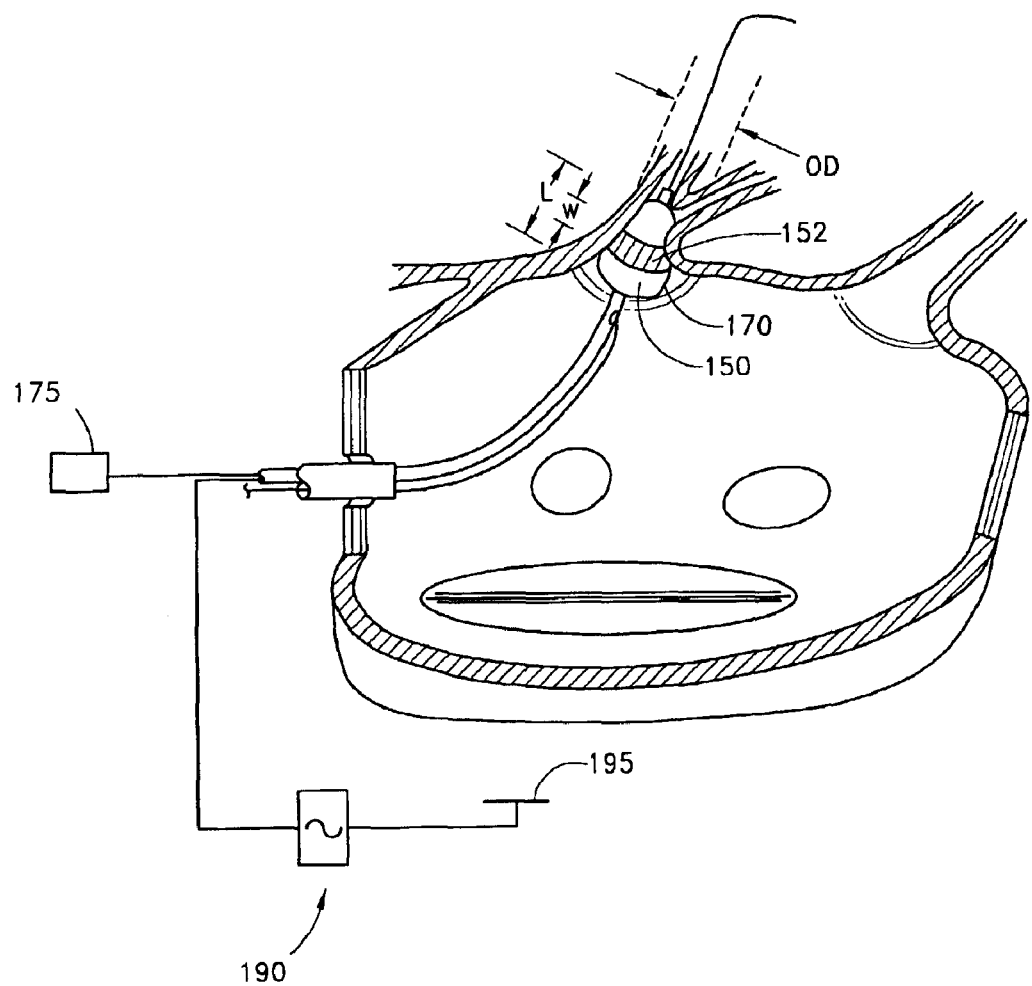
FIG. 5 shows a similar perspective view of the circumferential ablation device assembly shown in FIG. 4, and further shows a circumferential ablation catheter during use in ablating a circumferential region of tissue along a pulmonary vein wall to form a circumferential conduction block in the pulmonary vein according to the method of FIG. 3.

FIG. 4 also shows circumferential ablation catheter 103 with a circumferential ablation element 160 formed on an expandable member 170. The expandable member 170 is shown in FIG. 4 in a radially collapsed position adapted for percutaneous translumenal delivery into the pulmonary vein according to positioning step (3) of FIG. 3. However, expandable member 170 is also adjustable to a radially expanded position when actuated by an expansion actuator 175, as shown in FIG. 5. Expansion actuator 175 may include, but is not limited to, a pressurizable fluid source. According to the expanded state shown in FIG. 5, expandable member 170 includes a working length L relative to the longitudinal axis of the elongate catheter body which has a larger expanded outer diameter OD than when in the radially collapsed position. Furthermore, the expanded outer diameter OD is sufficient to circumferentially engage the ablation region of the pulmonary vein. Therefore, the terms "working length" are herein intended to mean the length of an expandable member which, when in a radially expanded position, has an expanded outer diameter that is: (a) greater than the outer diameter of the expandable member when in a radially collapsed position; and (b) sufficient to engage a body space wall or adjacent ablation region surrounding the expandable member, at least on two opposing internal sides of the body space wall or adjacent ablation region, with sufficient surface area to anchor the expandable member.

Circumferential ablation member 150 also includes a circumferential band (hatched) on the outer surface of working length L that is coupled to an ablation actuator 190 at a proximal end portion of the elongate catheter body (shown schematically). After expandable member 170 is adjusted to the radially expanded position and at least a portion of working length L circumferentially engages the pulmonary vein wall in the ablation region, the circumferential band of the circumferential ablation member 150 is actuated by ablation actuator 190 to ablate the surrounding circumferential path of tissue in the pulmonary vein wall, thereby forming a circumferential lesion that circumscribes the pulmonary vein lumen and transects the electrical conductivity of the pulmonary vein to block conduction in a direction along its longitudinal axis.

Figure 6B:
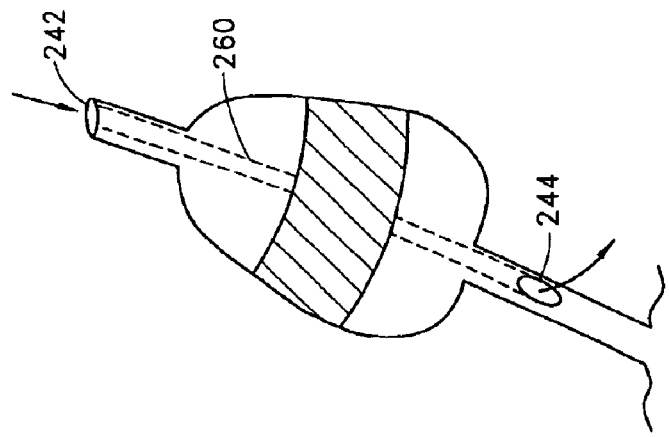
FIG. 6B is an enlarged partial view of the circumferential ablation catheter shown in FIG. 6A, with a perfusion lumen shown in phantom.
Figure 6A:
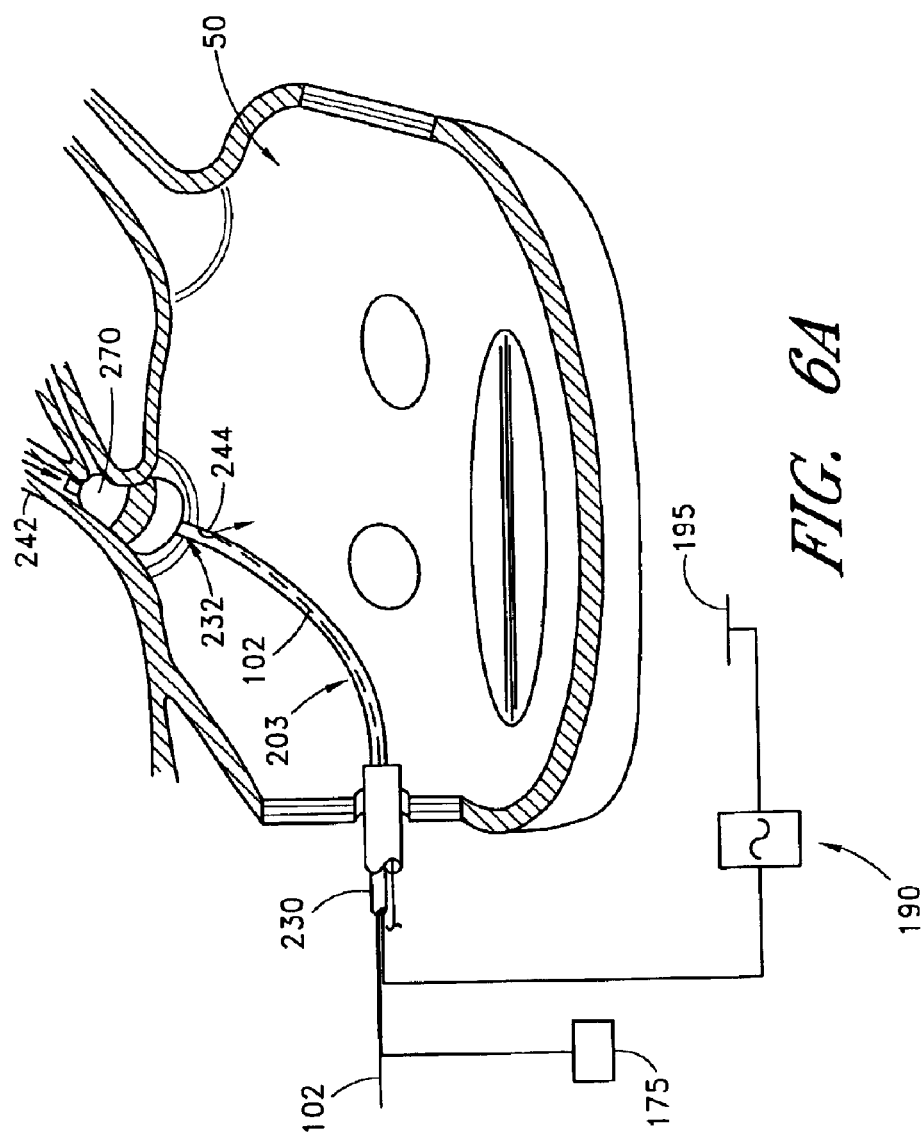
FIG. 6A shows a similar perspective view as shown in FIG. 5, although showing a circumferential ablation catheter which is adapted to allow for blood perfusion from the pulmonary vein and into the atrium while performing the circumferential ablation method shown diagrammatically in FIG. 3.

FIG. 6A shows another circumferential ablation catheter 203 during use also according to the method of FIG. 3, wherein a perfusion lumen 260 (shown in phantom in FIG. 6B) is formed within the distal end portion 132 of elongate catheter body 230. The perfusion lumen 260 in this example is formed between a distal perfusion port 242 (FIG. 6B), which in this example is the first distal guidewire port 242, and proximal perfusion port 244. Proximal perfusion port 244 is formed through the wall of the elongate catheter body 230 and communicates with the guidewire lumen (not shown), which also forms the perfusion lumen between the distal and proximal perfusion ports. In the particular design shown, after the guidewire has provided for the placement of the ablation element into the pulmonary vein, the guidewire is withdrawn proximally of the proximal perfusion port 244 so that the lumen (shown schematically in shadow) between the ports is clear for antegrade blood flow into the distal perfusion port 242, proximally along the perfusion lumen, out the proximal perfusion port 244 and into the atrium (perfusion flow shown schematically with arrows).

Further to the perfusion design shown in FIGS. 6A–B, guidewire 102 is positioned in a guidewire lumen which extends the entire length of the elongate catheter body 230 in an "over-the-wire"-type of design, which facilitates the proximal withdrawal of the guidewire to allow for perfusion while maintaining the ability to subsequently re-advance the guidewire distally through the first distal guidewire port 242 for catheter repositioning. In one alternative variation not shown, the guidewire is simply withdrawn and disengaged from the second distal guidewire port, in which case the circumferential ablation catheter must generally be withdrawn from the body in order to re-couple the distal guidewire tracking member with the guidewire.

In another alternative perfusion variation not shown which is a modification of the embodiment of FIG. 6A, a proximal perfusion port is provided as a separate and distinct port positioned between the second distal guidewire port and the expandable member, which allows for proximal withdrawal of the guidewire to clear the guidewire lumen and thereby form a perfusion lumen between the first distal guidewire port and the proximal perfusion port. The guidewire of this alternative variation, however, remains engaged within the guidewire lumen between the second distal guidewire port and the proximal perfusion port.

Passive perfusion during expansion of the expandable member is believed to minimize stasis and allow the target pulmonary vein to continue in its atrial filling function during the atrial arrhythmia treatment procedure. In addition, in cases where the ablation element is adapted to ablate tissue with heat conduction at the ablation region, as described by reference to more detailed embodiments below, the perfusion feature according to the variation of FIGS. 6A–B may also provide a cooling function in the surrounding region, including in the blood adjacent to the expandable member.

Moreover, in addition to the specific perfusion structure shown and described by reference to FIGS. 6A–B, it is to be further understood that other structural variants which allow for perfusion flow during expansion of the expandable element may provide suitable substitutes according to one of ordinary skill without departing from the scope of the present invention.

Figure 7:
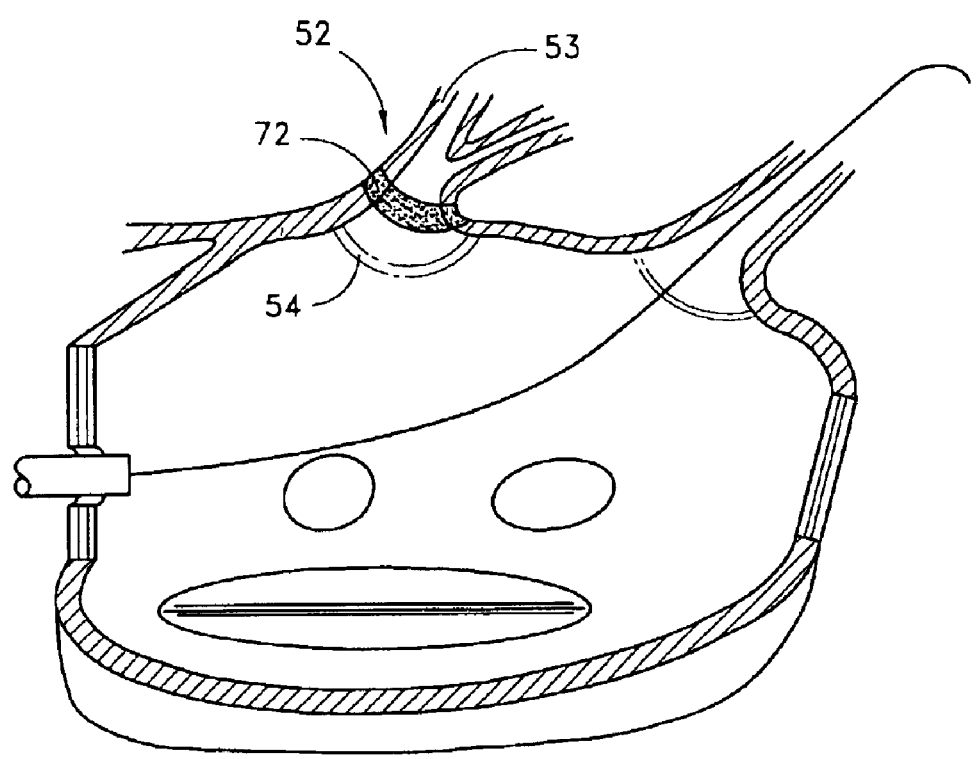
FIG. 7 shows a similar perspective view of the left atrium as that shown in FIGS. 3–5, although showing a cross-sectional view of a circumferential lesion after being formed by circumferential catheter ablation according to the method of FIG. 3.

FIG. 7 shows pulmonary vein 52 after removing the circumferential ablation device assembly subsequent to forming a circumferential lesion 70 around the ablation region of the pulmonary vein wall 53 according to the use of the circumferential ablation device assembly shown in step-wise fashion in FIGS. 3–6. Circumferential lesion 70 is shown located along the pulmonary vein adjacent to the pulmonary vein ostium 54, and is shown to also be "transmural," which is herein intended to mean extending completely through the wall, from one side to the other. Also, the circumferential lesion 70 is shown in FIG. 7 to form a "continuous" circumferential band, which is herein intended to mean without gaps around the pulmonary vein wall circumference, thereby circumscribing the pulmonary vein lumen.

It is believed, however, that circumferential catheter ablation with a circumferential ablation element according to the present invention may leave some tissue, either transmurally or along the circumference of the lesion, which is not actually ablated, but which is not substantial enough to allow for the passage of conductive signals. Therefore, the terms "transmural" and "continuous" as just defined are intended to have functional limitations, wherein some tissue in the ablation region may be unablated but there are no functional gaps which allow for symptomatically arrhythmogenic signals to conduct through the conduction block and into the atrium from the pulmonary vein.

Moreover, it is believed that the functionally transmural and continuous lesion qualities just described are characteristic of a completed circumferential conduction block in the pulmonary vein. Such a circumferential conduction block thereby transects the vein, isolating conduction between the portion of the vein on one longitudinal side of the lesion and the portion on the other side. Therefore, any foci of originating arrhythmogenic conduction which is opposite the conduction block from the atrium is prevented by the conduction block from conducting down into the atrium and atrial arrhythmic affects are therefore nullified.

Figure 8A:
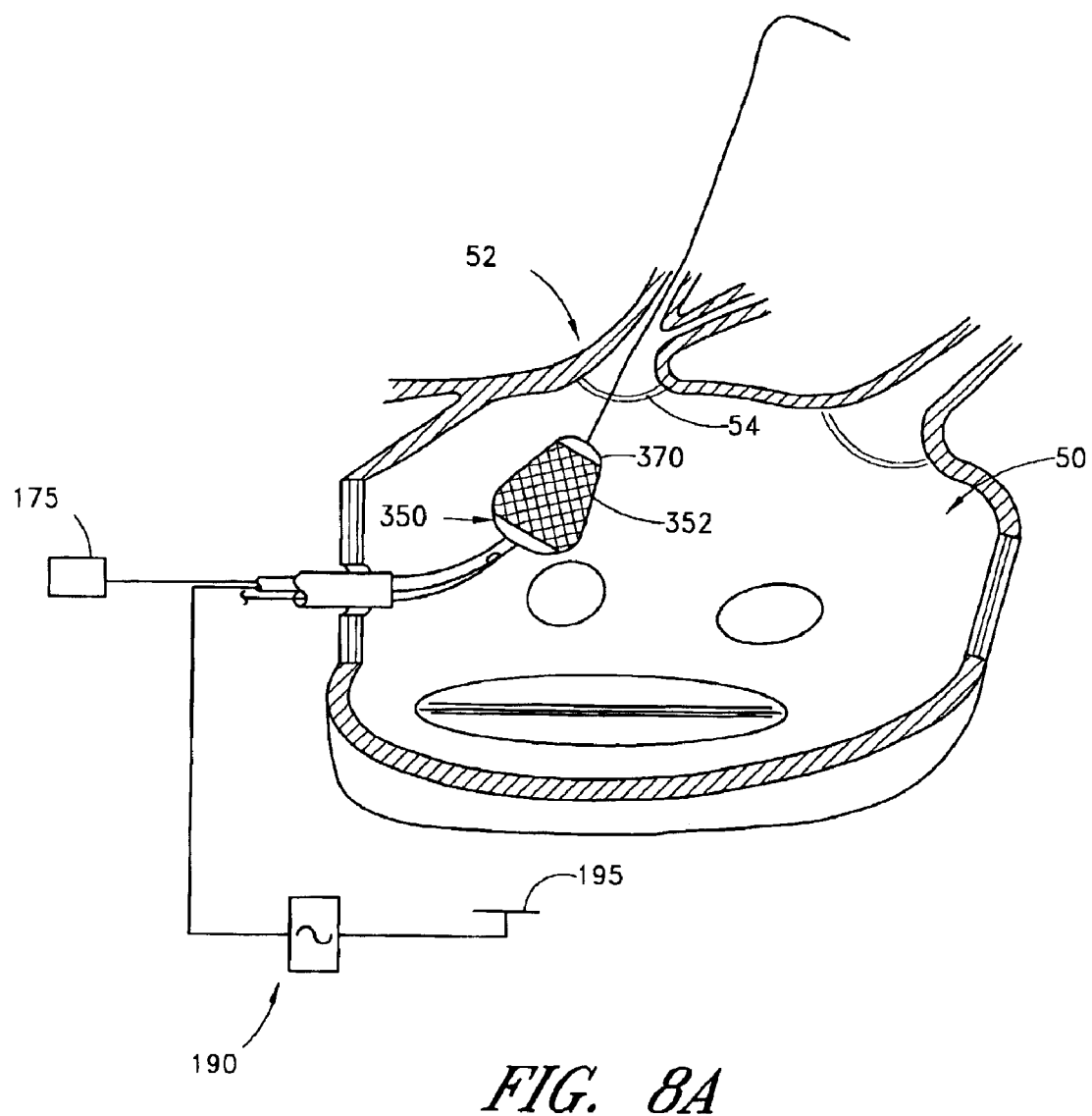
Figure 8B:
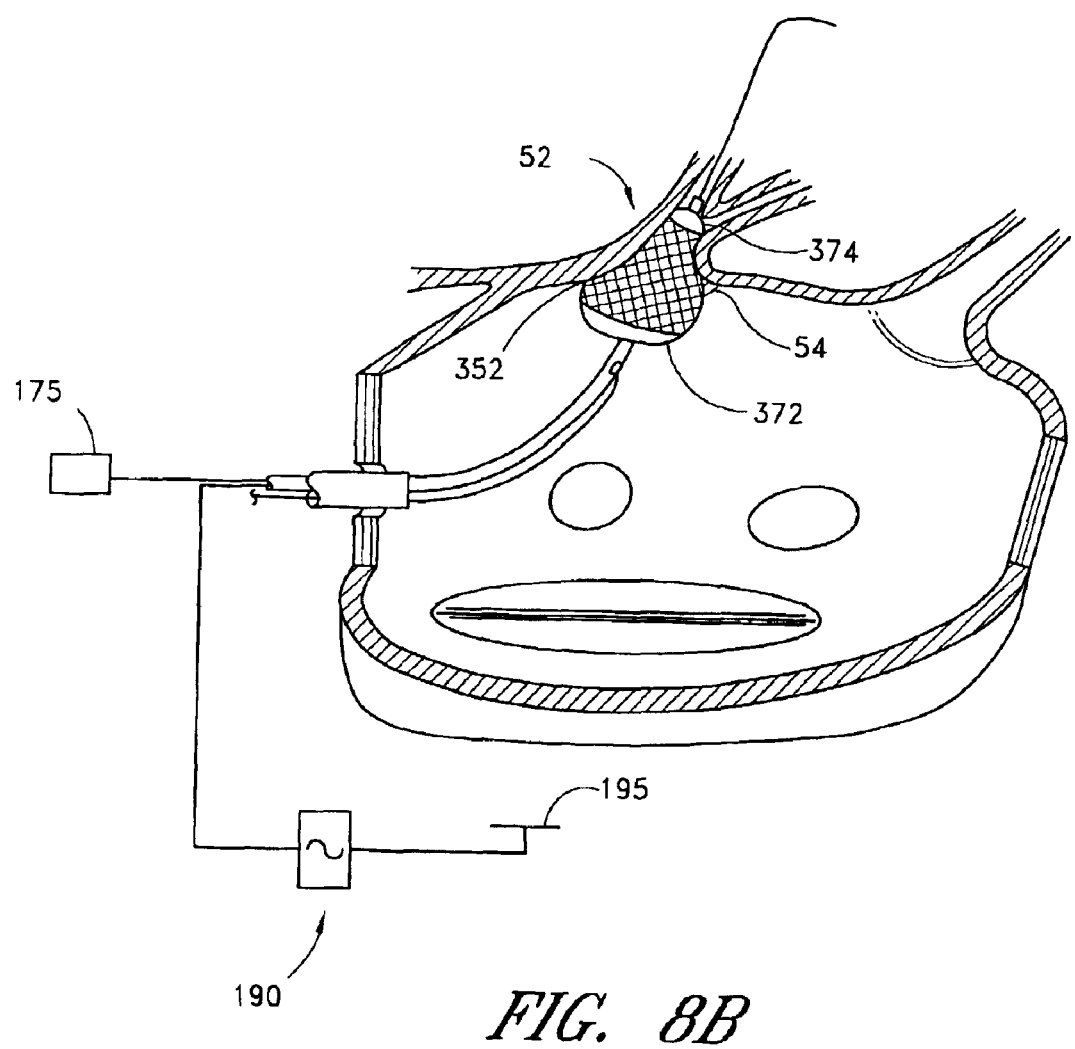
Figure 8C:
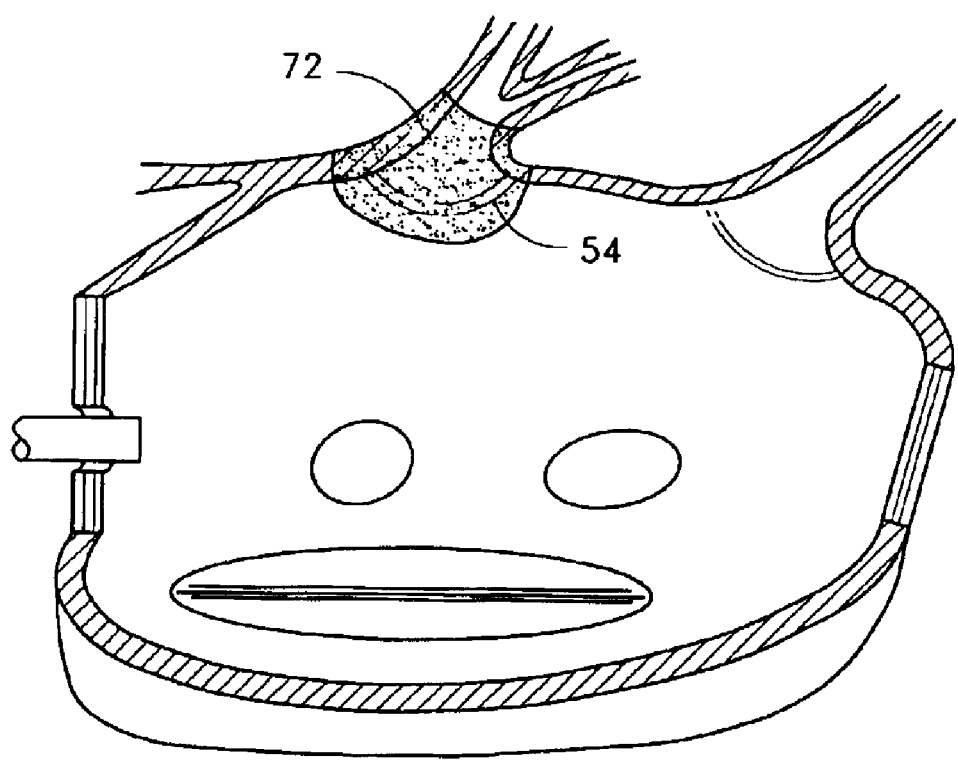
FIG. 8C shows the same perspective view of the left atrium shown in FIGS. 8A–B, although shown after forming a circumferential conduction block according to the circumferential ablation procedure of FIG. 3 and also after removing the circumferential ablation device assembly from the left atrium.

FIGS. 8A–B show a further variation of the present invention, wherein a circumferential ablation member 350 includes a radially compliant expandable member 370 which is adapted to conform to a pulmonary vein ostium 54 at least in part by adjusting it to a radially expanded position while in the left atrium and then advancing it into the ostium. A circumferential ablation element 352 forms a band around expandable member 370, and is coupled to ablation actuator 190. FIG. 8A shows expandable member 370 after being adjusted to a radially expanded position while located in the left atrium 50. FIG. 8B further shows the expandable member after being advanced into the pulmonary vein 52 until at least a portion of the expanded working length L of circumferential ablation member, which includes a circumferential ablation element 352, engages the pulmonary vein ostium 54. The tapered distal portion 374 of the expandable member is shown conforming to the vein 52, whereas the proximal portion 372 is radially expanded so that the circumferential ablation element 352 ablatively contacts the ostium 54, and in some cases, also a portion of the posterior wall of the atrium. FIG. 8C shows a portion of a circumferential lesion 72 that forms a circumferential conduction block that encompasses the region of the pulmonary vein ostium 54 subsequent to actuating the circumferential ablation element to form the circumferential lesion.

In addition to conforming to the pulmonary vein ostium, the proximal portion 372 of expandable member is also shown in FIG. 8B to engage a circumferential path of tissue along the left posterior atrial wall which surrounds ostium 54. Moreover, circumferential band 352 of the circumferential ablation member is also thereby adapted to engage that atrial wall tissue. Therefore, the circumferential conduction block formed according to the method shown and just described in sequential steps by reference to FIGS. 8A–B, as shown in-part in FIG. 8C, includes ablating the circumferential path of atrial wall tissue and pulmonary vein wall which surrounds ostium 54. Accordingly, the entire pulmonary vein, including the ostium, is thereby electrically isolated from at least a substantial portion of the left atrial wall which includes the other of the pulmonary vein ostia, as would be apparent to one of ordinary skill according to the sequential method steps shown in FIGS. 8A–B and by further reference to the resulting circumferential lesion 72 shown in FIG. 8C.

FIGS. 8D–E show another highly beneficial circumferential ablation device embodiment and use thereof for electrically isolating pulmonary vein and ostium from a substantial portion of the left posterior atrial wall. However, unlike the embodiment previously shown and described by reference to FIGS. 8A–C, the FIG. 8D–E embodiment isolates the pulmonary vein without also ablating tissue along the lumen or lining of the pulmonary vein or ostium, as is apparent by reference to the resulting circumferential conduction block 72' shown in FIG. 8F.

In more detail, FIG. 8D shows a similar device assembly as that shown in FIGS. 8A–B, except that circumferential band 352' has a geometry (primarily width) and position around the proximal portion 372' of the expandable member such that it is adapted to engage only a circumferential path of tissue along the left posterior atrial wall which surrounds the pulmonary vein ostium. The tapered distal portion 374' is shown engaging the pulmonary vein 52. In one aspect of this embodiment, the compliant nature of the expandable member may be self-conforming to the region of the ostium such that the circumferential band is placed against this atrial wall tissue merely by way of conformability.

In another variation, a "pear-shaped" expandable member or balloon that includes a contoured taper may be suitable for use according to the FIG. 8D embodiment, as is shown by way of example in FIG. 8E. Such a pear shape may be preformed into the expandable member or balloon, or the member may be adapted to form this shape by way of controlled compliance as it expands, such as for example by the use of composite structures within the balloon construction. In any case, according to the "pear-shaped" variation, the circumferential band 352' of the ablation member is preferably placed along the surface of the contoured taper which is adapted to face the left posterior atrial wall during use according to the method illustrated by FIG. 8D. It is further contemplated that the ablation element may be further extended or alternatively positioned along other portions of the taper, such as is shown by example in shadow at extended band 352" in FIG. 8E. Accordingly, the variation shown in FIG. 8E to include extended band 352" may also adapt this particular device embodiment for use in forming circumferential conduction blocks also along tissue within the pulmonary vein and ostium, such as according to the method shown in FIGS. 8A–C.

Figure 8F:
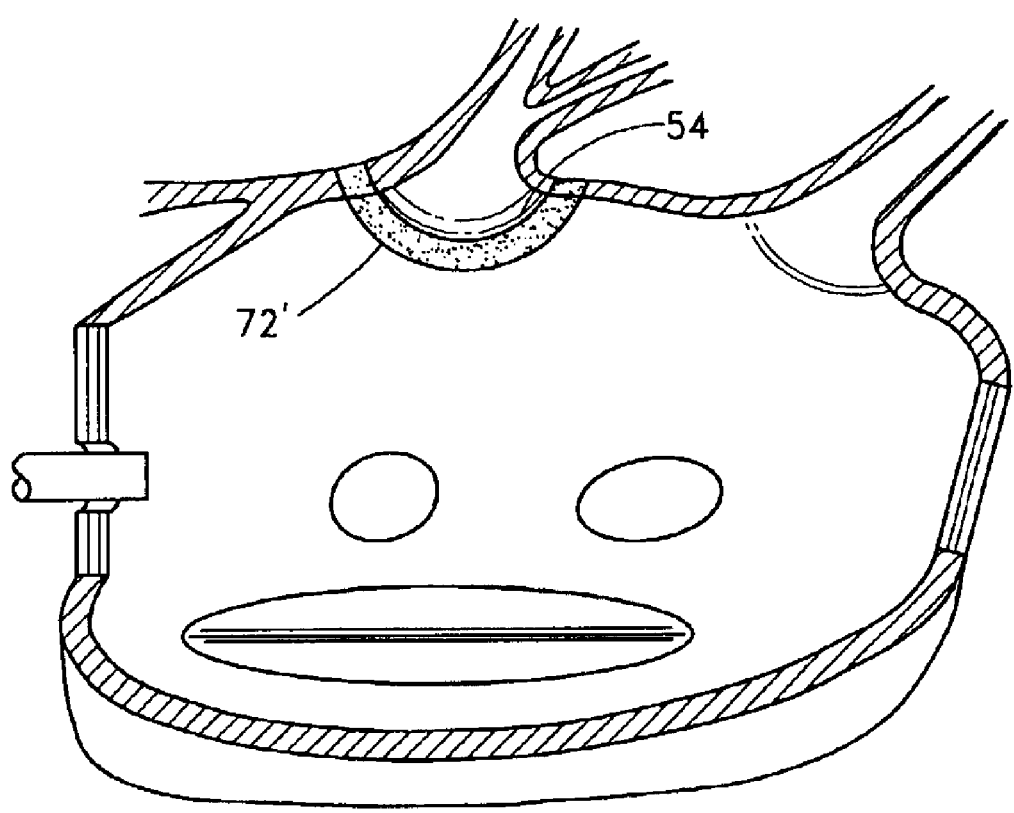
FIG. 8F shows a resulting circumferential conduction block or lesion which may be formed with the assemblies shown in FIGS. 8D–E and according to the method of use shown in FIG. 8D.

The method of forming a circumferential conduction block along a circumferential path of tissue along a left posterior atrial wall and which surrounds a pulmonary vein ostium without ablating the tissue of the vein or ostium should not be limited to the particular device embodiments just illustrated by reference to FIGS. 8D–F. Other device variations may be acceptable substitute for use according to this method. In one particular example which is believed to be suitable, a "looped" ablation member such as the embodiment illustrated below by reference to FIG. 15 may be adapted to form a "looped" ablation element within the left atrium and then be advanced against the left posterior atrial wall such that the loop engages the circumferential path of tissue along the atrial wall and which surrounds a vein ostium. Thereafter, the looped ablation element may be actuated to ablate the engaged tissue, such as for further illustration like a branding iron forming the predetermined pattern around the pulmonary vein ostium. In addition, other device or method variations may also be suitable substitutes according to one of ordinary skill.

FIGS. 9A–D collectively show a circumferential ablation device assembly according to the present invention as it is used to form a circumferential conduction block adjunctively to the formation of long linear lesions in a less-invasive "maze"-type procedure, as introduced above for the treatment of multiwavelet reentrant type fibrillation along the left atrial wall.

Figure 9A:
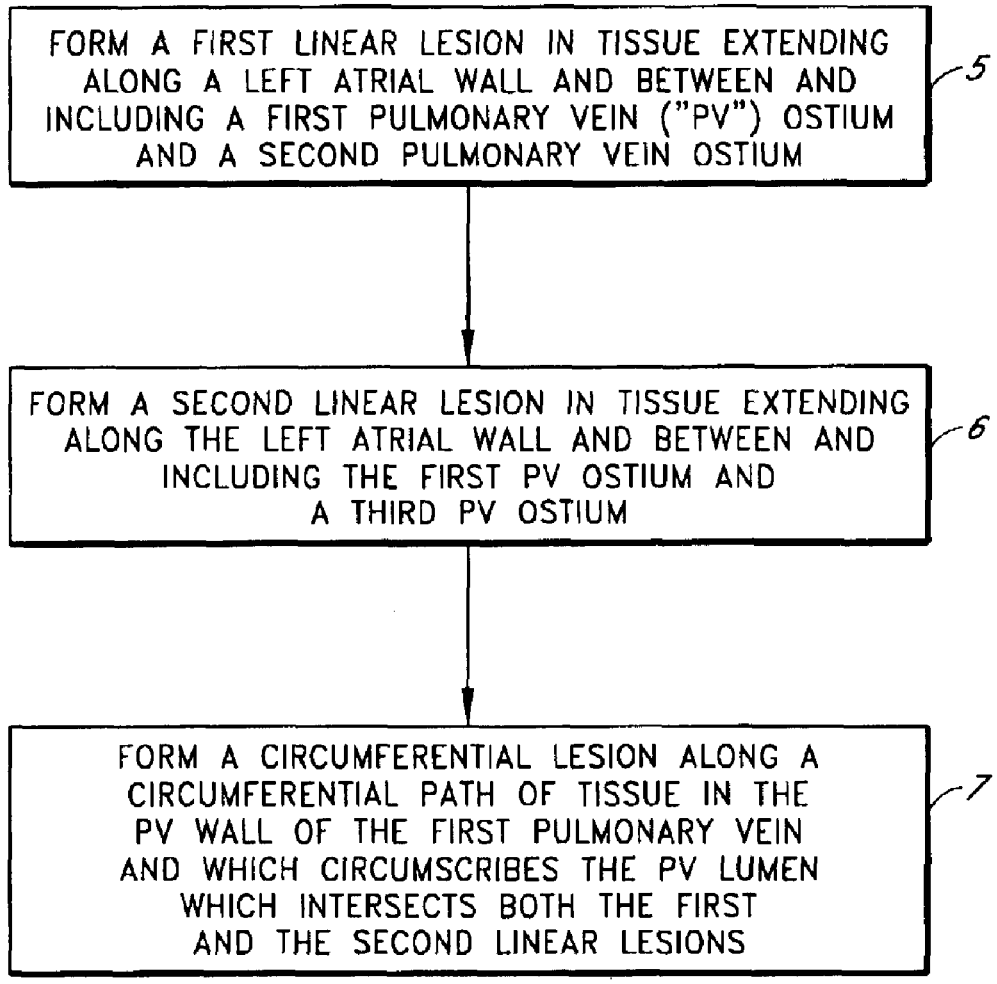
FIG. 9A diagrammatically shows a method for using a circumferential ablation device assembly to form a circumferential conduction block at a location where a pulmonary vein extends from an atrium in combination with a method for forming long linear lesions between pulmonary vein ostia in a less-invasive "maze"-type procedure.

More specifically, FIG. 9A diagrammatically shows a summary of steps for performing a "maze"-type procedure by forming circumferential conduction blocks that intersect with long linear conduction blocks formed between the pulmonary veins. As disclosed in co-pending patent application U.S. Ser. No. 08/853,861 entitled "Tissue Ablation Device and Method of Use", which is herein incorporated in its entirety by reference thereto, a box-like conduction block surrounding an arrhythmogenic atrial wall region bounded by the pulmonary veins may be created by forming long linear lesions 57,58 and 59 between anchors in all pairs of adjacent pulmonary vein ostia, such as is shown in part in steps (5) and (6) of FIG. 9A. However, it is further believed that, in some particular applications, such linear lesions may be made sufficiently narrow with respect to the surface area of the pulmonary vein ostia that they may not intersect, thereby leaving gaps between them which may present proarrhythmic pathways for abnormal conduction into and from the box, such as is shown between linear lesions 57 and 58 in FIG. 9B. Therefore, by forming the circumferential conduction block according to step (7) of FIG. 9A, and as shown by use of circumferential ablation member 450 in FIG. 9C, the linear lesions 57 and 58 are thereby bridged and the gaps are closed.

Figure 9B:
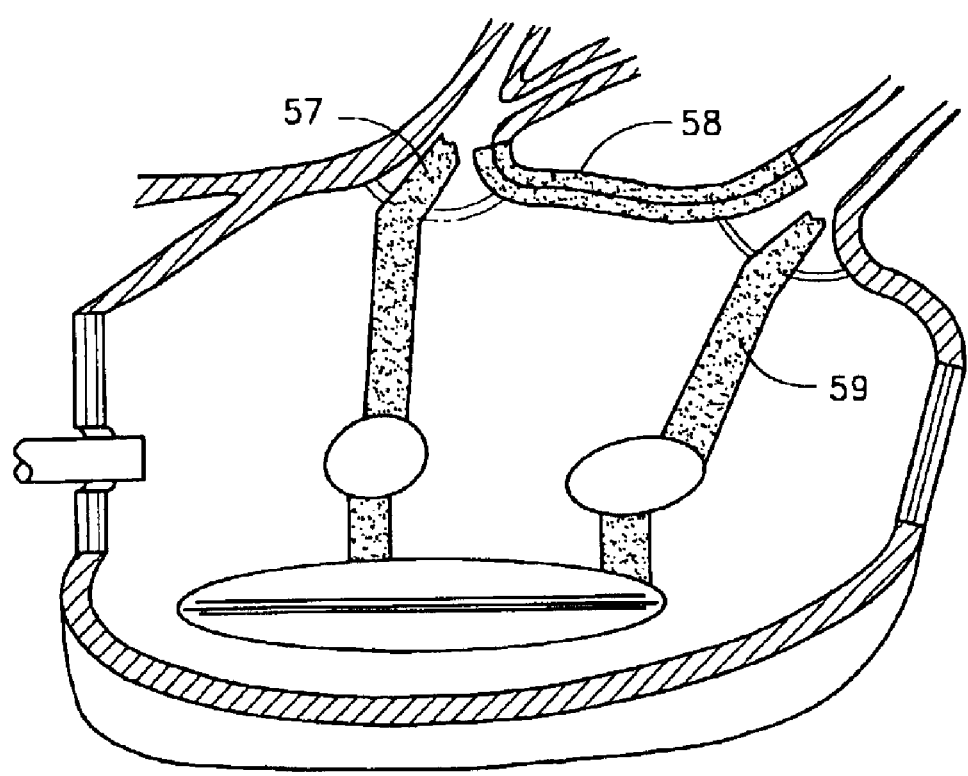
FIG. 9B shows a perspective view of a segmented left atrium after forming several long linear lesions between adjacent pairs of pulmonary vein ostia according to the method of FIG. 9A.
Figure 9C:
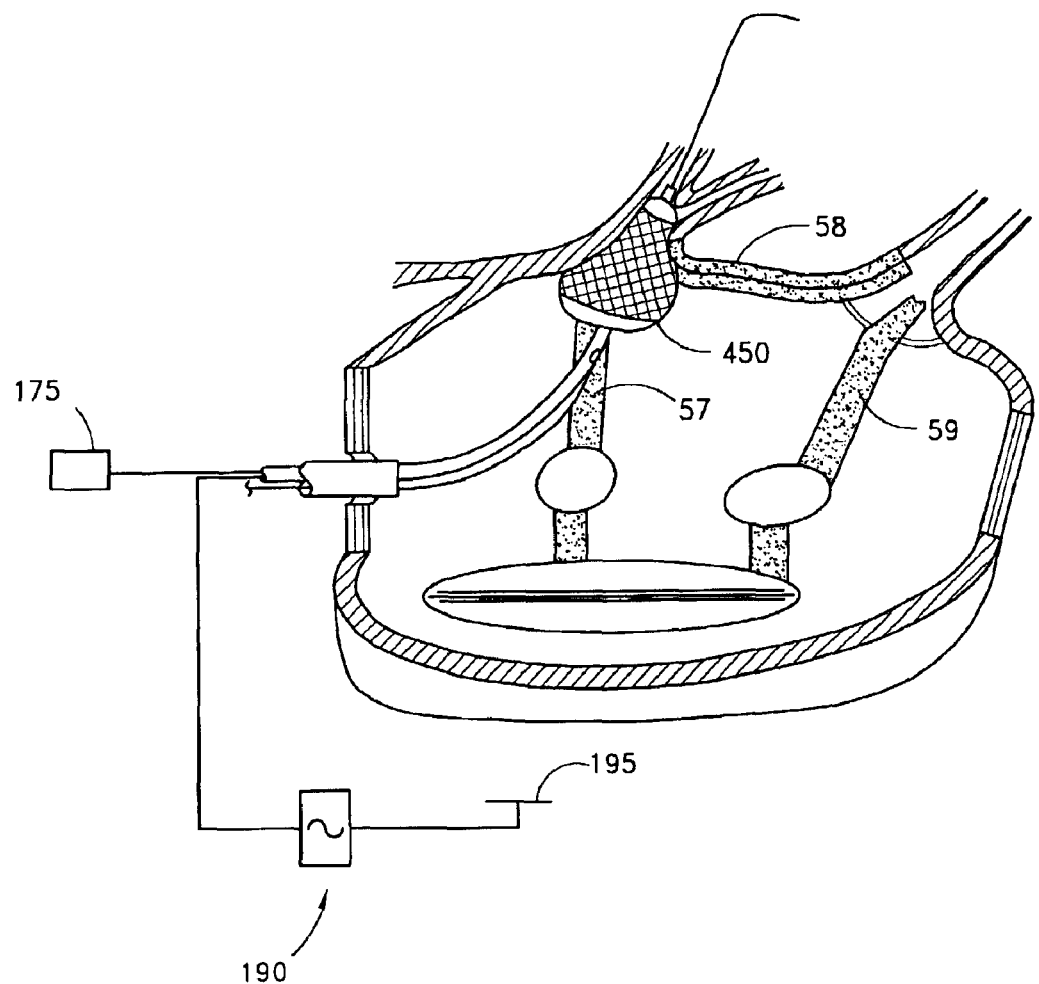
FIG. 9C shows a similar perspective view as that shown in FIG. 9B, although showing a circumferential ablation device assembly during use in forming a circumferential lesion at a location where a pulmonary vein extends from an atrium which intersects with two linear lesions that extend into the pulmonary vein, according to the method of FIG. 9A.
Figure 9D:
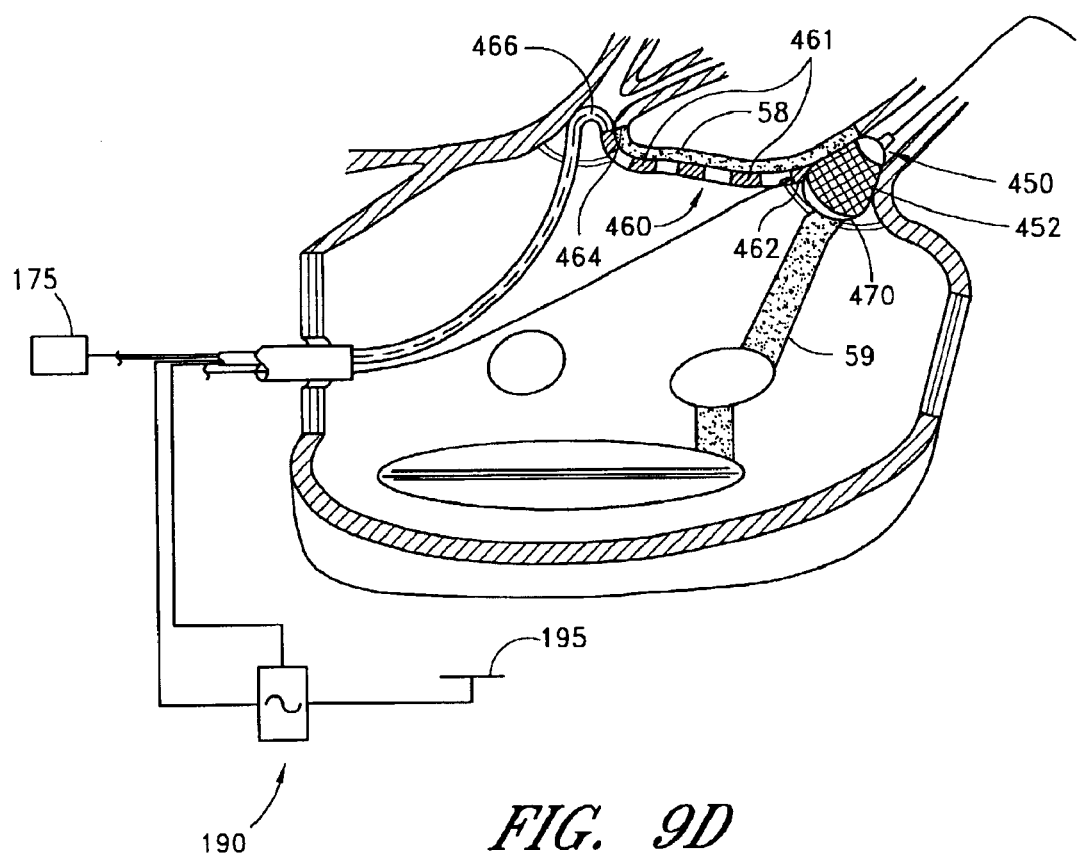
FIG. 9D shows a perspective view of another ablation catheter which combines a linear ablation member extending between two anchors with a circumferential ablation member for use in forming a circumferential lesion which intersects with at least one linear lesion according to the method of FIG. 9A.

In a further variation to the specific embodiments shown in FIGS. 9B–C, FIG. 9D shows another circumferential ablation device assembly, which includes both circumferential and linear ablation elements 452 and 461, respectively. Circumferential ablation member 450 is shown to include an expandable member 470 that is adjusted to a radially expanded position that is asymmetric to the underlying catheter shaft. Linear ablation member 460 extends along the elongate catheter body proximally from the circumferential ablation member 450. When expanded sufficiently to engage the pulmonary vein wall, expandable member 470 provides at least a portion of an anchor for a first end 462 of linear ablation member 460.

Figure 9E:
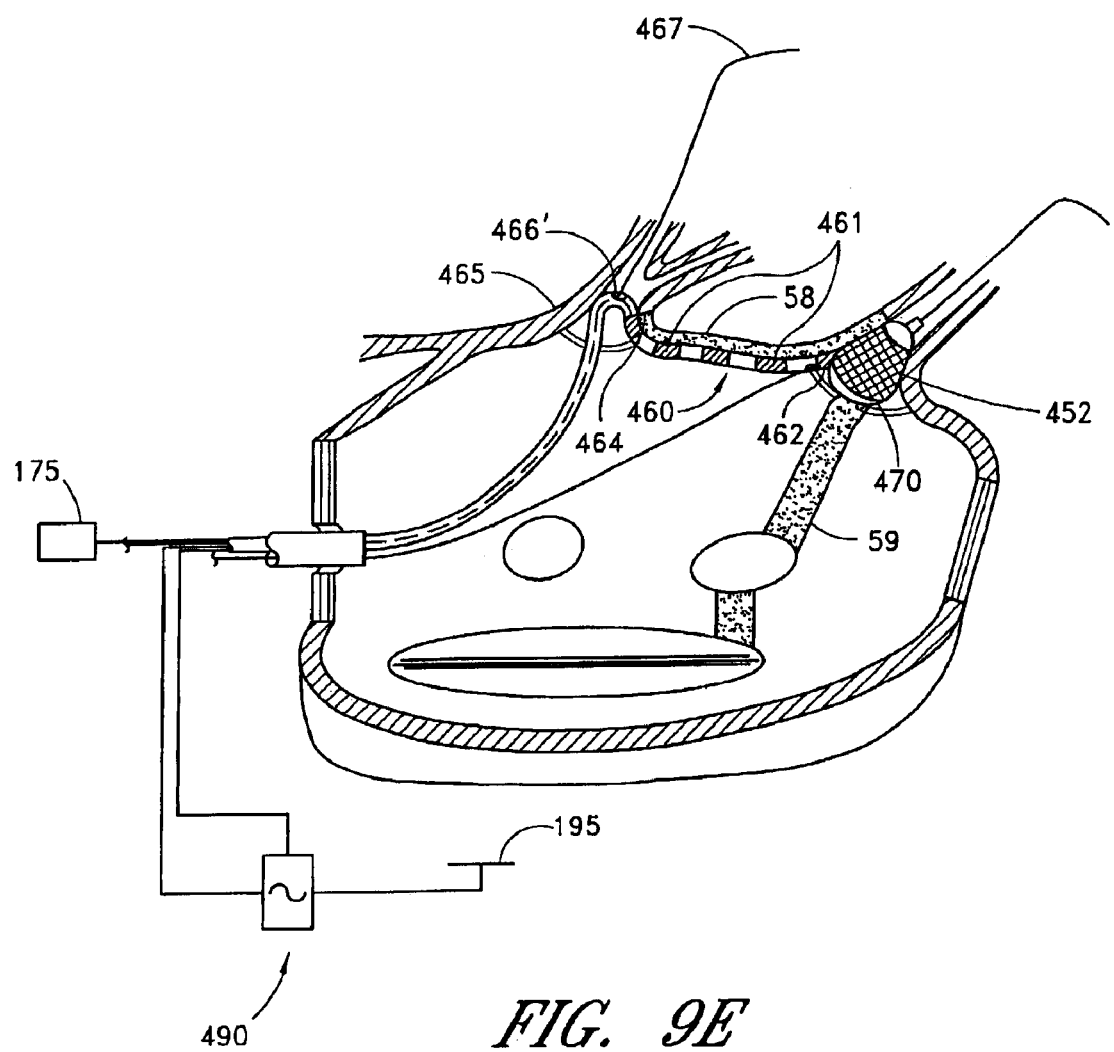
FIG. 9E shows a perspective view of another circumferential ablation catheter for use in forming a circumferential lesion that intersects with at least one linear lesion according to the method of FIG. 9A.

A shaped stylet 466 is shown in shadow in FIG. 9D within the elongate catheter body in the region of the second end 464 of the linear ablation member 460. Shaped stylet 466 is adapted to push the second end 464 into an adjacent pulmonary vein ostium such that the linear ablation member 460 is adapted to substantially contact the left atrial wall between the adjacent vein ostia to form the linear ablation according to the method of FIG. 9A. In addition to the use of shaped stylet 466, it is further contemplated that a different second anchor may be used adjacent to second end 464, such as for example an intermediate guidewire tracking member adapted to track over a guidewire engaged within the pulmonary vein, as shown in FIG. 9E at intermediate guidewire tracking member 466' which is engaged over guidewire 467.

Moreover, the method shown schematically in FIG. 9A and also in various detail by reference to FIGS. 9B–C provides a specific sequence of steps for the purpose of illustration. According to this illustrative sequence, the linear lesions are formed first and then are connected thereafter with the circumferential conduction block. However, a circumferential conduction block may be formed prior to the formation of the linear lesions or conduction blocks, or in any other combination or sub-combination of sequential steps, so long as the resulting combination of lesions allows for the circumferential block to intersect with and connect with the linear lesions. In addition, the circumferential conduction block which connects the linear lesions may also include a circumferential path of tissue which surrounds and electrically isolates the pulmonary vein ostium from the rest of the left posterior atrial wall, such as for example by considering the embodiments just shown and described by reference to FIGS. 9A–E in view of the embodiment previously shown and described in relation to FIG. 8C above.

Figure 9F:
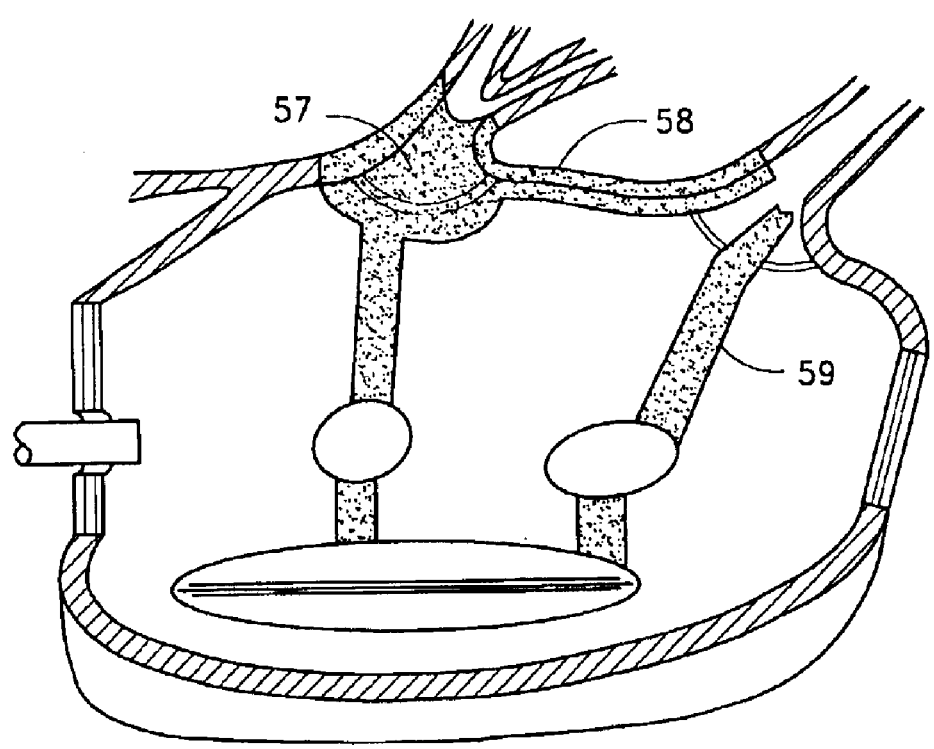
FIG. 9F shows a perspective view of a segmented left posterior atrial wall with a lesion pattern which results from combining the formation of two linear lesions according to FIG. 9B with the formation of a circumferential conduction block according to the methods and devices shown in FIGS. 8A–C.
Figure 9G:
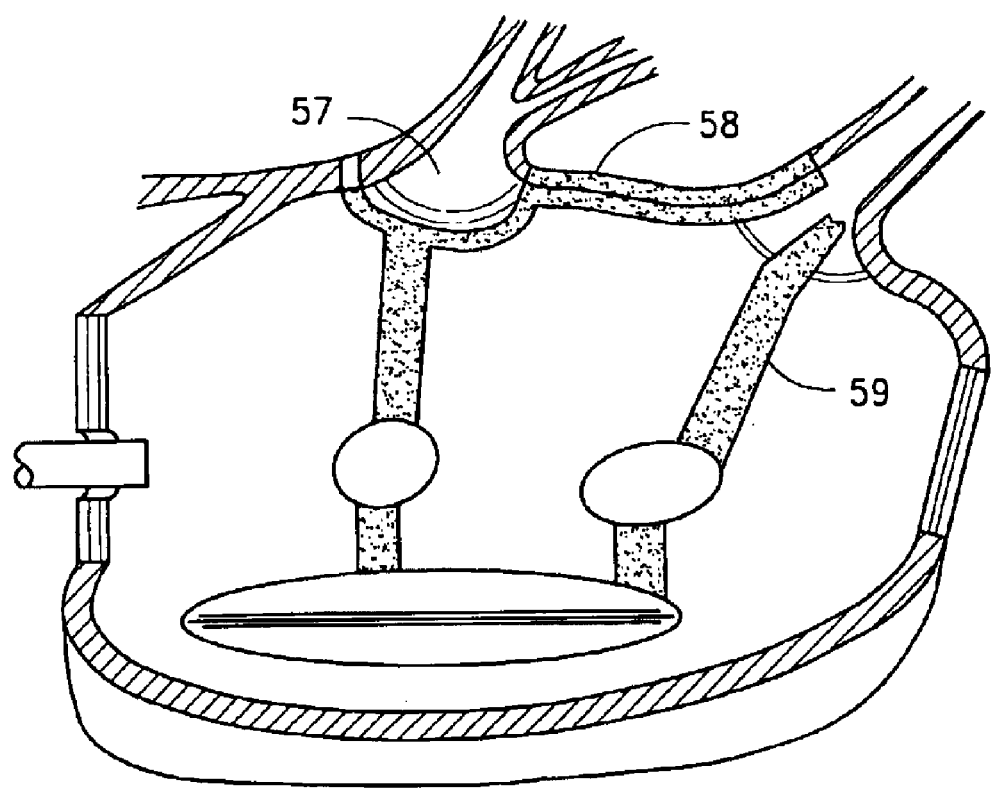
FIG. 9G shows a perspective view of a segmented left posterior atrial wall with a lesion pattern which results from combining the formation of two linear lesions according to FIG. 9B with the formation of a circumferential conduction block according to the methods and devices shown in FIGS. 8D–F.

In addition to the particular embodiments just shown and described by reference to FIGS. 9A–E, other methods are also contemplated for combining circumferential and linear conduction blocks device assemblies and uses in order to perform a less-invasive "maze"-type procedure. For example, FIG. 9F shows one particular lesion pattern which results by combining a circumferential conduction block 57, formed according to the previous embodiments of FIGS. 8A–C, with a pair of linear lesions which are formed according to the method illustrated by FIG. 9B. In a further example shown in FIG. 9G, another lesion pattern is formed by combining the pair of linear lesions of FIG. 9B with a circumferential conduction block formed according to the embodiments which are previously illustrated above by reference to FIGS. 9D–F. While the resulting lesion patterns of FIGS. 9F and 9G differ slightly as regards the particular geometry and position of the circumferential conduction block formed, the two variations are also similar in that the circumferential conduction block includes a circumferential path of atrial wall tissue. When such circumferential conduction blocks are formed between adjacent pulmonary vein ostia, shorter linear lesions are therefore sufficient to bridge the circumferential lesions during the overall "maze"-type procedure.

To this end, the invention further contemplates one further variation for a less-invasive "maze"-type procedure (not shown) wherein multiple circumferential conduction blocks are formed in atrial wall tissue such that each pulmonary vein ostium is surrounded by and is electrically isolated with one circumferential conduction block. A series of four linear lesions may be formed between the various pairs of adjacent ostia and with just sufficient length to intersect with and bridge the corresponding adjacent circumferential blocks. A box-like conduction block is thereby formed by the four circumferential conduction blocks and the four bridging linear lesions. A fifth linear lesion may be also formed between at least a portion of the box-like conduction block and another predetermined location, such as for example the mitral value annulus.

Figure 9H:
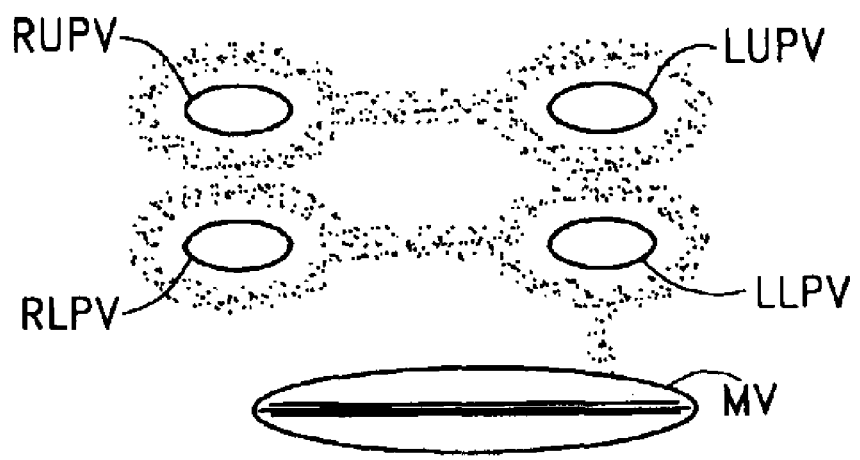
FIG. 9H shows a schematic perspective view of a left posterior atrial wall with one complete lesion pattern in a variation of a less-invasive "maze"-type procedure wherein circumferential conduction blocks are formed along circumferential paths of tissue along a left posterior atrial wall such that each circumferential conduction block surrounds a pulmonary vein ostium, each pair of vertically adjacent circumferential conduction blocks intersects, and each pair of horizontally adjacent circumferential conduction blocks are connected with one of two linear lesions extending between the respective pair of horizontally adjacent pulmonary vein ostia.

FIG. 9H shows yet a further variation for forming circumferential conduction blocks along atrial wall tissue around the pulmonary vein ostia during a less invasive "maze"-type procedure. According to this further variation, the circumferential conduction block patterns formed around each of two adjacent superior and inferior pulmonary vein ostia are shown in FIG. 9H to intersect, thereby alleviating the need for a linear lesion in order to form a conduction block between the ostia. Furthermore, the distances between the inferior and superior ostia, both on the right and left side of the posterior atrial wall, are believed to be significantly shorter than the distances between the two adjacent superior or inferior ostia. Therefore, FIG. 9H only shows the overlapping circumferential conduction blocks as just described to be positioned vertically between the inferior-superior pairs of adjacent ostia, and further shows linear lesions which are used to connect the right and left sided ostia of the superior and inferior pairs. In some instances these linear lesions will not be required to cure, treat or prevent a particular atrial arrhythmia condition. However, other combinations of these patterns are further contemplated, such as for example using only overlapping circumferential conduction blocks between all adjacent pairs of ostia in order to form the entire "maze"-type left atrial pattern.

Figure 10:
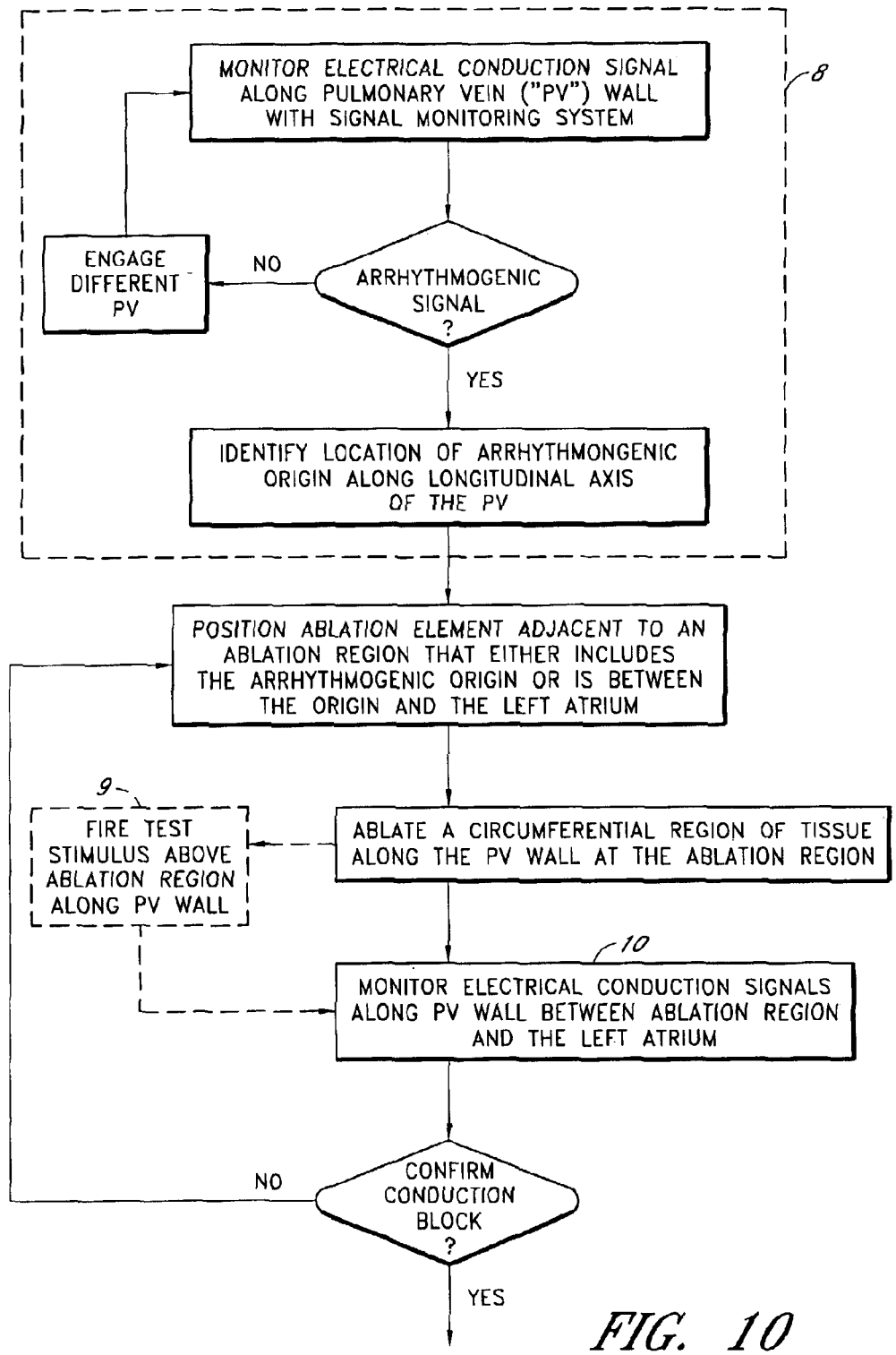
FIG. 10 diagrammatically shows a further method for using a circumferential ablation device assembly to form a circumferential conduction block at a location where a pulmonary vein extends from an atrium wall, wherein signal monitoring and "postablation" test elements are used to locate an arrhythmogenic origin along the pulmonary vein wall and to test the efficacy of a circumferential conduction block in the wall, respectively.

FIG. 10 diagrammatically shows a further method for using the circumferential ablation device assembly of the present invention wherein electrical signals along the pulmonary vein are monitored with a sensing element before and after ablation according to steps (8) and (9), respectively. Signals within the pulmonary vein are monitored prior to forming a conduction block, as indicated in step (8) in FIG. 10, in order to confirm that the pulmonary vein chosen contains an arrhythmogenic origin for atrial arrhythmia. Failure to confirm an arrhythmogenic origin in the pulmonary vein, particularly in the case of a patient diagnosed with focal arrhythmia, may dictate the need to monitor signals in another pulmonary vein in order to direct treatment to the proper location in the heart. In addition, monitoring the pre-ablation signals may be used to indicate the location of the arrhythmogenic origin of the atrial arrhythmia, which information helps determine the best location to form the conduction block. As such, the conduction block may be positioned to include and therefore ablate the actual focal origin of the arrhythmia, or may be positioned between the focus and the atrium in order to block aberrant conduction from the focal origin and into the atrial wall.

In addition or in the alternative to monitoring electrical conduction signals in the pulmonary vein prior to ablation, electrical signals along the pulmonary vein wall may also be monitored by the sensing element subsequent to circumferential ablation, according to step (9) of the method of FIG. 10. This monitoring method aids in testing the efficacy of the ablation in forming a complete conduction block against arrhythmogenic conduction. Arrhythmogenic firing from the identified focus will not be observed during signal monitoring along the pulmonary vein wall when taken below a continuous circumferential and transmural lesion formation, and thus would characterize a successful circumferential conduction block. In contrast, observation of such arrhythmogenic signals between the lesion and the atrial wall characterizes a functionally incomplete or discontinuous circumference (gaps) or depth (transmurality), which would potentially identify the need for a subsequent follow-up procedure, such as a second circumferential lesioning procedure in the ablation region.

A test electrode may also be used in a "post ablation" signal monitoring method according to step (10) of FIG. 10. In one particular embodiment not shown, the test electrode is positioned on the distal end portion of an elongate catheter body and is electrically coupled to a current source for firing a test signal into the tissue surrounding the test electrode when it is placed distally or "upstream" of the circumferential lesion in an attempt to simulate a focal arrhythmia. This test signal generally challenges the robustness of the circumferential lesion in preventing atrial arrhythmia from any such future physiologically generated aberrant activity along the suspect vein.

Further to the signal monitoring and test stimulus methods just described, such methods may be performed with a separate electrode or electrode pair located on the catheter distal end portion adjacent to the region of the circumferential ablation element, or may be performed using one or more electrodes which form the circumferential ablation element itself, as will be further developed below.

The designs for the expandable member and circumferential ablation element for use in a circumferential ablation device assembly as herein described have been described generically with reference to the embodiments shown in the previous Fig.'s. Examples of various specific expandable member and ablation element structures that are adapted for use in such assemblies and methods are further provided as follows.

Notwithstanding their somewhat schematic detail, the circumferential ablation members shown in the previous Fig.'s do illustrate one particular embodiment wherein a circumferential electrode element circumscribes an outer surface of an expandable member. The expandable member of the embodiments shown may take one of several different forms, although the expandable member is generally herein shown as an inflatable balloon that is coupled to an expansion actuator which is a pressurizeable fluid source. The balloon is preferably made of a polymeric material and forms a fluid chamber that communicates with a fluid passageway (not shown in the Fig.'s) that extends proximally along the elongate catheter body and terminates proximally in a proximal fluid port that is adapted to couple to the pressurizeable fluid source.

In one expandable balloon variation, the balloon is constructed of a relatively inelastic polymer such as a polyethylene ("PE"; preferably linear low density or high density or blends thereof), polyolefin copolymer ("POC"), polyethylene terepthalate ("PET"), polyimide, or a nylon material. In this construction, the balloon has a low radial yield or compliance over a working range of pressures and may be folded into a predetermined configuration when deflated in order to facilitate introduction of the balloon into the desired ablation location via known percutaneous catheterization techniques. In this variation, one balloon size may not suitably engage all pulmonary vein walls for performing the circumferential ablation methods of the present invention on all needy patients. Therefore, it is further contemplated that a kit of multiple ablation catheters, with each balloon working length having a unique predetermined expanded diameter, may be provided from which a treating physician may chose a particular device to meet a particular patient's pulmonary vein anatomy.

In an alternative expandable balloon variation, the balloon is constructed of a relatively compliant, elastomeric material, such as, for example (but not limited to), a silicone, latex, polyurethane, or mylar elastomer. In this construction, the balloon takes the form of a tubular member in the deflated, non-expanded state. When the elastic tubular balloon is pressurized with fluid such as in the previous, relatively non-compliant example, the material forming the wall of the tubular member elastically deforms and stretches radially to a predetermined diameter for a given inflation pressure. It is further contemplated that the compliant balloon may be constructed as a composite, such as, for example, a latex or silicone balloon skin which includes fibers, such as metal, Kevlar, or nylon fibers, which are embedded into the skin. Such fibers, when provided in a predetermined pattern such as a mesh or braid, may provide a controlled compliance along a preferred axis, preferably limiting longitudinal compliance of the expandable member while allowing for radial compliance.

It is believed that, among other features, the relatively compliant variation may provide a wide range of working diameters, which may allow for a wide variety of patients, or of vessels within a single patient, to be treated with just one or a few devices. Furthermore, this range of diameters is achievable over a relatively low range of pressures, which is believed to diminish a potentially traumatic vessel response that may otherwise be presented concomitant with inflation at higher pressures, particularly when the inflated balloon is oversized to the vessel. In addition, the low-pressure inflation feature of this variation is suitable for the present invention because the functional requirement of the expandable balloon is merely to engage the ablation element against a circumferential path along the inner lining of the pulmonary vein wall.

Moreover, a circumferential ablation member is adapted to conform to the geometry of the pulmonary vein ostium, at least in part by providing substantial compliance to the expandable member, as was shown and described previously by reference to FIGS. 8A–B. Further to this conformability to pulmonary vein ostia as provided in the specific design of FIGS. 8A–B, the working length L of expandable member is also shown to include a taper which has a distally reducing outer diameter from a proximal end to a distal end. In either a compliant or the non-compliant balloon, such a distally reducing tapered geometry adapts the circumferential ablation element to conform to the funneling geometry of the pulmonary veins in the region of their ostia in order to facilitate the formation of a circumferential conduction block there.

Further to the circumferential electrode element embodiment as shown variously throughout the previous illustrative Fig.'s, the circumferential electrode element is coupled to an ablation actuator 190. Ablation actuator 190 generally includes a radiofrequency ("RF") current source (not shown) that is coupled to both the RF electrode element and also a ground patch 195 that is in skin contact with the patient to complete an RF circuit. In addition, ablation actuator 190 preferably includes a monitoring circuit (not shown) and a control circuit (not shown) which together use either the electrical parameters of the RF circuit or tissue parameters such as temperature in a feedback control loop to drive current through the electrode element during ablation. Also, where a plurality of ablation elements or electrodes in one ablation element are used, a switching means may be used to multiplex the RF current source between the various elements or electrodes.

FIGS. 11A–D show various patterns of electrically conductive, circumferential electrode bands as electrode ablation elements, each circumscribing an outer surface of the working length of an expandable member. FIGS. 11A–B show circumferential ablation member 550 to include a continuous circumferential electrode band 552 that circumscribes an outer surface of an expandable member 570. FIG. 11B more specifically shows expandable member 570 as a balloon which is fluidly coupled to a pressurizeable fluid source 175, and further shows electrode band (circumferential ablation element) 552 electrically coupled via electrically conductive lead 554 to ablation actuator 190. In addition, a plurality of apertures 572 are shown in the balloon skin wall of expandable member 570 adjacent to electrode band 552. The purpose of these apertures 572 is to provide a positive flow of fluid such as saline or ringers lactate fluid into the tissue surrounding the electrode band 552. Such fluid flow is believed to reduce the temperature rise in the tissue surrounding the electrode element during RF ablation.

The shapes shown collectively in FIGS. 11A–D allow for a continuous electrode band to circumscribe an expandable member's working length over a range of expanded diameters, a feature which is believed to be particularly useful with a relatively compliant balloon as the expandable member. In the particular embodiments of FIGS. 11A–D, this feature is provided primarily by a secondary shape given to the electrode band relative to the longitudinal axis of the working length of the expandable member. Electrode band 552 is thus shown in FIGS. 11A–B to take the specific secondary shape of a modified step curve. Other shapes than a modified step curve are also suitable, such as the serpentine or sawtooth secondary shapes shown respectively in FIGS. 11C–D. Other shapes in addition to those shown in FIGS. 11A–D and which meet the defined functional requirements are further contemplated within the scope of the present invention.

In addition, the electrode band provided by the circumferential ablation elements shown in FIGS. 11C–D and also shown schematically in FIGS. 3–6B has a functional band width w relative to the longitudinal axis of the working length which is only required to be sufficiently wide to form a complete conduction block against conduction along the walls of the pulmonary vein in directions parallel to the longitudinal axis. In contrast, the working length L of the respective expandable element is adapted to securely anchor the distal end portion in place such that the ablation element is firmly positioned at a selected region of the pulmonary vein for ablation. Accordingly, the band width w is relatively narrow compared to the working length L of the expandable element, and the electrode band may thus form a relatively narrow equatorial band that has a band width that is less than two-thirds or even one-half of the working length of the expandable element. Additionally, it is to be noted here and elsewhere throughout the specification, that a narrow band may be placed at locations other than the equator of the expandable element, preferably as long as the band is bordered on both sides by a portion of the working length L.

In another aspect of the narrow equatorial band variation for the circumferential ablation element, the circumferential lesion formed may also be relatively narrow when compared to its own circumference, and may be less than two-thirds or even one-half its own circumference on the expandable element when expanded. In one arrangement, which is believed to be suitable for ablating circumferential lesions in the pulmonary veins as conduction blocks, the band width w is less than 1 cm with a circumference on the working length when expanded that is greater than 1.5 cm.

FIGS. 12A–B show a further variation of a circumferential ablation element which is adapted to maintain a continuous circumferential lesion pattern over a range of expanded diameters and which includes electrode elements that form a relatively narrow equatorial band around the working length of an expandable balloon member. In this variation, a plurality of individual electrode/ablation elements 562 are included in the circumferential ablation element and are positioned in spaced arrangement along an equatorial band which circumscribes an outer surface of the expandable member's working length L.

The size and spacing between these individual electrode elements 562, when the balloon is expanded, is adapted to form a substantially continuous circumferential lesion at a location where a pulmonary vein extends from an atrium when in intimal contact adjacent thereto, and is further adapted to form such a lesion over a range of band diameters as the working length is adjusted between a variety of radially expanded positions. Each individual electrode element 562 has two opposite ends 563,564, respectively, along a long axis LA and also has a short axis SA, and is positioned such that the long axis LA is at an acute angle relative to the longitudinal axis La of the elongate catheter body and expandable member 560. At least one of the ends 563,564 along the long axis LA overlaps with an end of another adjacent individual electrode element, such that there is a region of overlap along their circumferential aspect, i.e., there is a region of overlap along the circumferential coordinates. The terms "region of overlap along their circumferential coordinate" are herein intended to mean that the two adjacent ends each are positioned along the working length with a circumferential and also a longitudinal coordinate, wherein they share a common circumferential coordinate. In this arrangement, the circumferential compliance along the working length, which accompanies radial expansion of the expandable member, also moves the individual electrode elements apart along the circumferential axis. However, the spaced, overlapping arrangement described allows the individual ablation elements to maintain a certain degree of their circumferential overlap, or at least remain close enough together, such that a continuous lesion may be formed without gaps between the elements.

The construction for suitable circumferential electrode elements in the RF variation of the present invention, such as the various electrode embodiments described with reference to FIGS. 11A–12B, may comprise a metallic material deposited on the outer surface of the working length using conventional techniques, such as by plasma depositing, sputter coating, chemical vapor deposition, other known techniques which are equivalent for this purpose, or otherwise affixing a metallic shaped member onto the outer surface of the expandable member such as through known adhesive bonding techniques. Other RF electrode arrangements are also considered within the scope of the present invention, so long as they form a circumferential conduction block as previously described. For example, a balloon skin may itself be metallized, such as by mixing conductive metal, including but not limited to gold, platinum, or silver, with a polymer to form a compounded, conductive matrix as the balloon skin.

Still further to the RF electrode embodiments, another circumferential ablation member variation (not shown) may also include an expandable member, such as an inflatable balloon, that includes a porous skin that is adapted to allow fluid, such as hypertonic saline solution, to pass from an internal chamber defined by the skin and outwardly into surrounding tissues. Such a porous skin may be constructed according to several different methods, such as by forming holes in an otherwise contiguous polymeric material, including mechanically drilling or using laser energy, or the porous skin may simply be an inherently porous membrane. In any case, by electrically coupling the fluid within the porous balloon skin to an RF current source (preferably monopolar), the porous region of the expandable member serves as an RF electrode wherein RF current flows outwardly through the pores via the conductive fluid. In addition, it is further contemplated that a porous outer skin may be provided externally of another, separate expandable member, such as a separate expandable balloon, wherein the conductive fluid is contained in a region between the porous outer skin and the expandable member contained therein. Various other "fluid electrode" designs than those specifically herein described may also be suitable according to one of ordinary skill upon review of this disclosure.

In the alternative, or in addition to the RF electrode variations just described, the circumferential ablation element may also include other ablative energy sources or sinks, and particularly may include a thermal conductor that circumscribes the outer circumference of the working length of an expandable member. Examples of suitable thermal conductor arrangements include a metallic element that may, for example, be constructed as previously described for the more detailed RF embodiments above. However, in the thermal conductor embodiment such a metallic element would be generally either resistively heated in a closed loop circuit internal to the catheter, or conductively heated by a heat source coupled to the thermal conductor. In the latter case of conductive heating of the thermal conductor with a heat source, the expandable member may be, for example, a polymeric balloon skin that is inflated with a fluid that is heated either by a resistive coil or by bipolar RF current. In any case, it is believed that a thermal conductor on the outer surface of the expandable member is suitable when it is adapted to heat tissue adjacent thereto to a temperature between 40° and 80° C.

Further to the thermal conduction variation for the circumferential ablation element, the perfusion balloon embodiment as shown in FIGS. 6A–B may be particularly useful in such a design. It is believed that ablation through increased temperatures, as provided by example above may also enhance coagulation of blood in the pulmonary vein adjacent to the expandable member, which blood would otherwise remain stagnant without such a perfusion feature.

Figure 13:
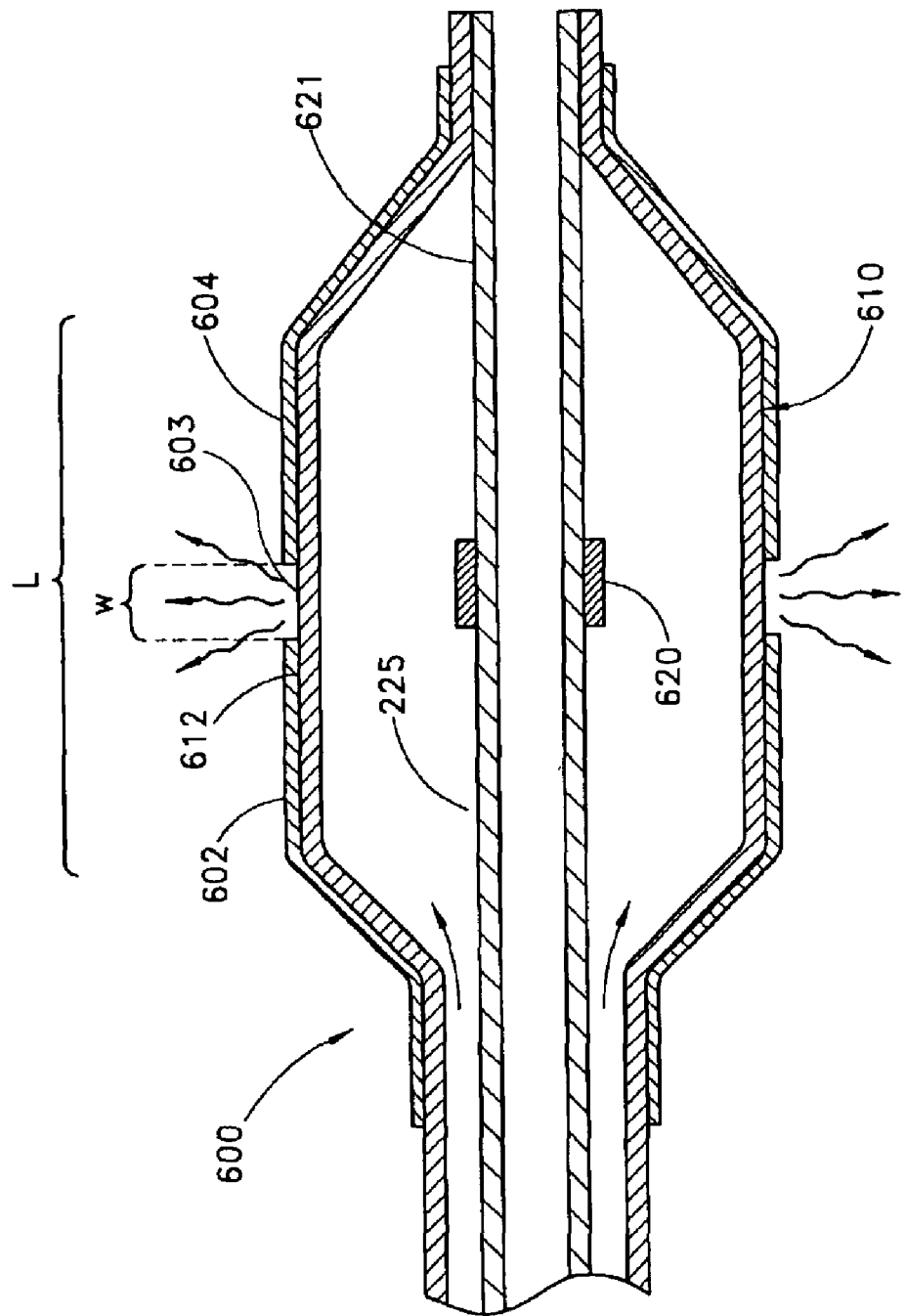
FIG. 13 shows a cross-sectional view of another circumferential ablation member for use in a circumferential ablation device assembly, wherein the circumferential ablation element circumscribes an outer surface of an expandable member substantially along its working length and is insulated at both the proximal and the distal ends of the working length to thereby form an uninsulated equatorial band in a middle region of the working length or otherwise circumferential region of the working length which is bounded both proximally and distally by end portions of the working length, which member is adapted to ablate a circumferential path of tissue in a pulmonary wall adjacent to the equatorial band.

One further circumferential ablation element design that is believed to be highly useful in performing the methods according to the present invention is shown in FIG. 13 to include a circumferential ablation member 600 with two insulators 602,604 that encapsulate the proximal and distal ends, respectively, of the working length L of an expandable member 610. In the particular embodiment shown, the insulators 602,604 are thermal insulators, such as a thermal insulator comprising a Teflon material. Expandable member 610 is an inflatable balloon which has a balloon skin 612 that is thermally conductive to surrounding tissue when inflated with a heated fluid that may contain a radiopaque agent, saline fluid, ringers lactate, combinations thereof, and/or other known biocompatible fluids having acceptable heat transfer properties for these purposes. By providing these spaced insulators, a circumferential ablation element is formed as an equatorial band 603 of uninsulated balloon skin located between the opposite insulators. In this configuration, the circumferential ablation element is able to conduct heat externally of the balloon skin much more efficiently at the uninsulated equatorial band 603 than at the insulated portions, and thereby is adapted to ablate only a circumferential region of tissue in a pulmonary vein wall that is adjacent to the equatorial band. It is further noted that this embodiment is not limited to an "equatorial" placement of the ablation element. Rather, a circumferential band may be formed anywhere along the working length of the expandable member and circumscribing the longitudinal axis of the expandable member as previously described.

FIG. 13 further shows use of a radiopaque marker 620 to identify the location of the equatorial band 603 in order to facilitate placement of that band at a selected ablation region of a pulmonary vein via X-ray visualization. Radiopaque marker 620 is opaque under X-ray, and may be constructed, for example, of a radiopaque metal such as gold, platinum, or tungsten, or may comprise a radiopaque polymer such as a metal loaded polymer. FIG. 13 shows radiopaque marker 620 positioned coaxially over an inner tubular member 621 that is included in a coaxial catheter design as would be apparent to one of ordinary skill. Such a radiopaque marker may also be combined with the other embodiments herein shown and described. When the circumferential ablation member that forms an equatorial band includes a metallic electrode element, such electrode may itself be radiopaque and may not require use of a separate marker as just described.

The thermal insulator embodiment just described by reference to FIG. 13 is illustrative of a broader embodiment, wherein a circumferential ablation member has an ablating surface along the entire working length of an expandable member, but is shielded from releasing ablative energy into surrounding tissues except for along an unshielded or uninsulated equatorial band. As such, the insulator embodiment contemplates other ablation elements, such as the RF embodiments previously described above, which are provided along the entire working length of an expandable member and which are insulated at their ends to selectively ablate tissue only about an uninsulated equatorial band.

In a further example using the insulator embodiment in combination with a circumferential RF electrode embodiment, a metallized balloon that includes a conductive balloon skin may have an electrical insulator, such as a polymeric coating, at each end of the working length and thereby selectively ablate tissue with electricity flowing through the uninsulated equatorial band. In this and other insulator embodiments, it is further contemplated that the insulators described may be only partial and still provide the equatorial band result. For instance, in the conductive RF electrode balloon case, a partial electrical insulator will allow a substantial component of current to flow through the uninsulated portion due to a "shorting" response to the lower resistance in that region.

In still a further example of an insulator combined with a RF ablation electrode, a porous membrane comprises the entire balloon skin of an expandable member. By insulating the proximal and distal end portions of the working length of the expandable member, only the pores in the unexposed equatorial band region are allowed to effuse the electrolyte that carries an ablative RF current.

Further to the expandable member design for use in a circumferential ablation element according to the present invention, other expandable members than a balloon are also considered suitable. For example, in one expandable cage embodiment shown in FIG. 14, cage 650 comprises coordinating wires 651 and is expandable to engage a desired ablation region at a location where a pulmonary vein extends from an atrium.

The radial expansion of cage 650 is accomplished as follows. Sheath 652 is secured around the wires proximally of cage 650. However, core 653, which may be a metallic mandrel such as stainless steel, extends through sheath 652 and distally within cage 650 wherein it terminates in a distal tip 656. Wires 651 are secured to distal tip 656, for example, by soldering, welding, adhesive bonding, heat shrinking a polymeric member over the wires, or any combination of these methods. Core 653 is slideable within sheath 652, and may, for example, be housed within a tubular lumen (not shown) within sheath 652, the wires being housed between a coaxial space between the tubular lumen and sheath 652. By moving the sheath 652 relative to core 653 and distal tip 656 (shown by arrows in FIG. 14), the cage 650 is collapsible along its longitudinal axis in order to force an outward radial bias (also shown with arrows in FIG. 14) to wires 651 in an organized fashion to formed a working length of cage 650 which is expanded (not shown).

Figure 14:
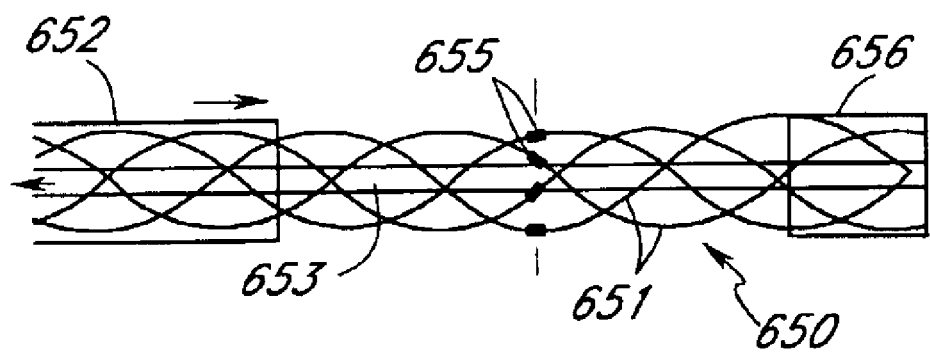
FIG. 14 shows a perspective view of another circumferential ablation member which is adapted for use in a circumferential ablation device assembly, wherein the expandable member is shown to be a cage of coordinating wires which are adapted to be adjusted from a radially collapsed position to a radially expanded position in order to engage electrode elements on the wires about a circumferential pattern of tissue at a location where a pulmonary vein extends from an atrium.

Further to the particular expandable cage embodiment shown in FIG. 14, a plurality of ablation electrodes 655 is shown, each being positioned on one of wires 651 and being similarly located along the longitudinal axis of the cage 650. The radial bias given to wires 651 during expansion, together with the location of the ablation electrodes 655, serves to position the plurality of ablation electrodes/elements 655 along a circumferential, equatorial band along the expanded working length of cage 650. The wires forming a cage according to this embodiment may also have another predetermined shape when in the radially expanded position. For example, a taper similar to that shown for expandable member 370 in FIG. 8A may be formed by expanding cage 650, wherein the ablation element formed by ablation electrodes 655 may be positioned between the proximal end and the distal end of the taper.

Further to the construction of the embodiment shown in FIG. 14, wires 651 are preferably metal, and may comprise stainless steel or a superelastic metal alloy, such as an alloy of nickel and titanium, or a combination of both. Regarding the case of nickel and titanium construction for the wires 655, a separate electrical conductor may be required in order to actuate ablation electrodes 655 to efficiently emit ablative current into surrounding tissues. In the case where wires 651 are constructed of stainless steel, they may also serve as electrical conductors for ablation electrodes 655. Further to the stainless steel design, the wires 651 may be coated with an electrical insulator to isolate the electrical flow into surrounding tissues at the site of the ablation electrodes 655. Moreover, the ablation electrodes 655 in the stainless steel wire variation may be formed simply by removing electrical insulation in an isolated region to allow for current to flow into tissue only from that exposed region.

In a further cage embodiment (not shown) to that shown in FIG. 14, a circumferential strip of electrodes may also be secured to the cage such that the strip circumscribes the cage at a predetermined location along the cage's longitudinal axis. By expanding cage as previously described, the strip of electrodes are adapted to take a circumferential shape according to the shape of the expanded cage. Such an electrode strip is preferably flexible, such that it may be easily reconfigured when the cage is adjusted between the radially collapsed and expanded positions and such that the strip may be easily advanced and withdrawn with the cage within the delivery sheath. Furthermore, the electrode strip may be a continuous circumferential electrode such as a conductive spring coil, or may be a flexible strip that includes several separate electrodes along its circumferential length. In the latter case, the flexible strip may electrically couple all of the electrodes to a conductive lead that interfaces with a drive circuit, or each electrode may be separately coupled to one or more such conductive leads.

Figure 15:
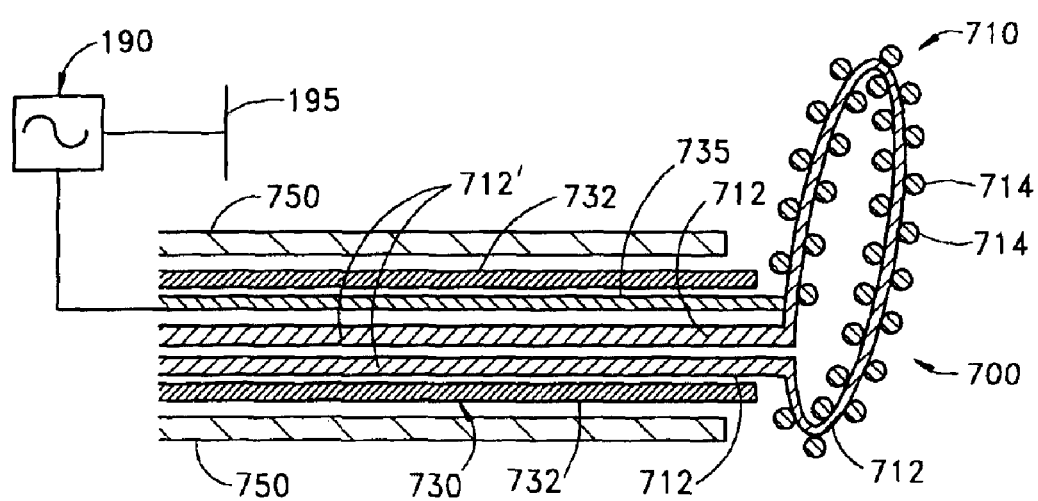
FIG. 15 shows a cross-sectional view of another circumferential ablation element which is adapted for use in a circumferential ablation device assembly of the present invention, wherein a superelastic, looped electrode element is shown at the distal end of a pusher and is adapted to circumferentially engage a circumferential region of tissue at a location where a pulmonary vein extends from an atrium to form a circumferential lesion as a conduction block that circumscribes the pulmonary vein lumen.

Another circumferential ablation element adapted for use in the circumferential conduction block assembly according to the present invention is shown in FIG. 15, wherein circumferential ablation member 700 includes a looped member 710 attached, preferably by heat shrinking, to a distal end of a pusher 730. Looped member 710 and pusher 730 are slideably engaged within delivery sheath 750 such that looped member 710 is in a first collapsed position when positioned and radially confined within delivery sheath 750, and expands to a second expanded position when advanced distally from delivery sheath 750.

Looped member 710 is shown in more detail in FIG. 15 to include a core 712 which is constructed of a superelastic metal alloy such as a nickel-titanium alloy and which has a looped portion with shape memory in the looped configuration. This looped configuration is shown in FIG. 15 to be in a plane that is off-axis, preferably perpendicular, to the longitudinal axis of the pusher 730. This off-axis orientation of the loop is adapted to engage a circumferential path of tissue along a pulmonary vein wall that circumscribes the pulmonary vein lumen when the looped member 710 is delivered from the delivery sheath 750 when the delivery sheath is positioned within the vein lumen parallel to its longitudinal axis. An ablation electrode 714 is also shown in FIG. 15 as a metallic coil that is wrapped around core 712 in its looped portion.

Pusher 730 is further shown in FIG. 15 to include a tubular pusher member 732 that is heat shrunk over two ends 712' of core 712 which extend proximally of looped member 710 through pusher 730 in the particular variation shown. While in this embodiment, core 712 extends through the pusher in order to provide stiffness to the composite design for the pusher. It is further contemplated that the superelastic metal of the core may be replaced or augmented in the pusher region with another different mandrel or pusher core (not shown), such as a stiffer stainless steel mandrel. Also shown within pusher 730 is an electrically conductive lead 735 which is coupled to the ablation electrode 714 and which is also adapted in a proximal region of the pusher (not shown) to couple to an ablation actuator 190 such as an RF current source (shown schematically).

The embodiments shown and described with reference to FIGS. 16–31 below are believed to provide assemblies that are particularly well adapted for ablating a circumferential region of tissue along the posterior left atrial wall that surrounds a pulmonary vein ostium and isolates the surrounded tissue including the pulmonary vein from the rest of the left atrium in order to prevent atrial fibrillation.

Figure 16A:
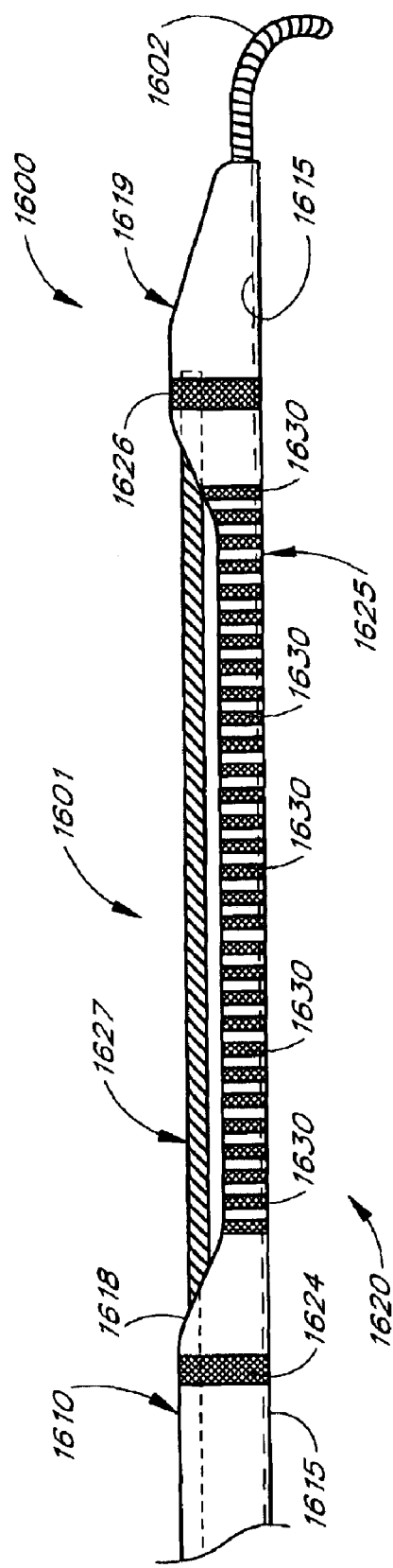
FIG. 16A shows a longitudinal perspective view of a circumferential ablation device assembly according to the invention, and shows a circumferential ablation member with an elongated ablation element along an elongated body which is shown in a first shape having a linear geometry which is adapted to be delivered through a delivery sheath into a left atrium.
Figures 16B, 16C:
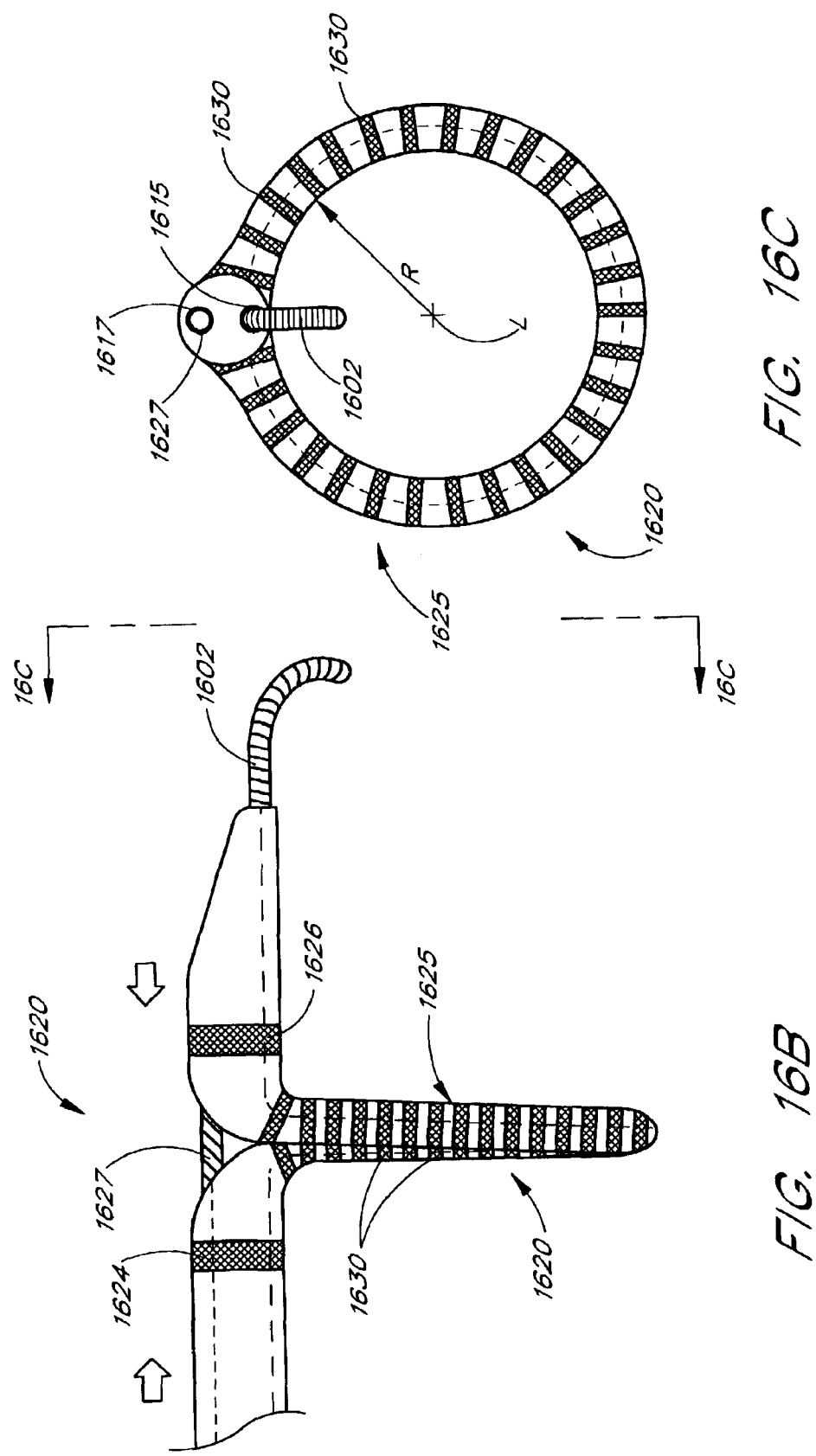
FIG. 16B shows an exploded longitudinal perspective view of the circumferential ablation member shown in FIG. 16A, but shows the elongated body after being adjusted to a shape with a looped geometry that is adapted to engage and ablate a circumferential region of tissue.
FIG. 16C shows a transverse cross-sectional view taken through line 16C—16C shown in FIG. 16B.

According to the circumferential ablation device assembly 1600 shown in FIGS. 16A–C, a plurality of electrodes 1630 are spaced along elongated member 1625, which is disposed on the distal end portion of catheter body 1610. Elongated member 1625 is adjustable between a first shape (shown in FIG. 16A), which substantially extends along the longitudinal axis L of catheter body 1610, to a second shape (FIG. 16B), which has a looped geometry about a circumference substantially along a plane that is orthogonal to the longitudinal axis L. The first shape is adapted for delivery through a delivery sheath and into the left atrium. The second shape is adapted to position the ablation elements about a circumference in order to form the circumferential ablation element for ablating a circumferential region of tissue where a pulmonary vein extends from a left atrium.

More specifically, an actuating assembly incorporating pull wire 1667 is used to adjust the elongated member 1625 between shapes. Pull wire 1627 is secured to tip 1626 distally of elongated member 1625 and extends proximally along the side of elongated member 1625 and further through port 1618 where it is slideably engaged within a passageway (not shown) along catheter body 1610, terminating along the proximal end portion of catheter body 1610, where it may be manipulated. Because the distal end 1626 of elongated member 1625 is also secured to tip 1619, pulling pull wire 1627 relative to catheter body 1610 longitudinally collapses distal end 1626 toward proximal end 1624 along pull wire 1627 and thereby deflects elongated member 1625 radially outwardly from the catheter assembly. By pre-forming a bias onto elongated member, the elongated member 1625 forms a loop along a plane that is orthogonal to the longitudinal axis of the catheter body 1610, as shown in FIGS. 16B–C.

Moreover, the assembly 1600 is further shown to be adapted to track over a guidewire 1602 via a guidewire lumen 1615 that is shown in FIGS. 16A–C to extend along elongated member 1625 and further proximally along catheter body 1610. As such, elongated member 1625 is preferably positioned over a sufficiently flexible portion of the guidewire in order to form the looped shape as just described. Moreover, it is further contemplated that distal and proximal guidewire tracking members or bores (not shown) may be provided on distal tip 1619 and catheter body 1610, respectively, such that the guidewire 1602 may also extend along the outside of elongated member 1625 and pull wire 1627, such that the elongate member's shape when deflected is not affected by guidewire 1602. Further to this dual tracking member embodiment, a stop (not shown) may be provided on guidewire 1602 distally of distal tip 1619 such that pull wire 1627 is no longer necessary to adjust the shapes of elongated body 1610. In this embodiment, by advancing distal tip 1619 against a stop, the proximal and distal ends 1624,1626 of elongated member 1625 are longitudinally collapsed together along guidewire 1602 to provide the desired deflection for elongated member 1625.

Figure 17:
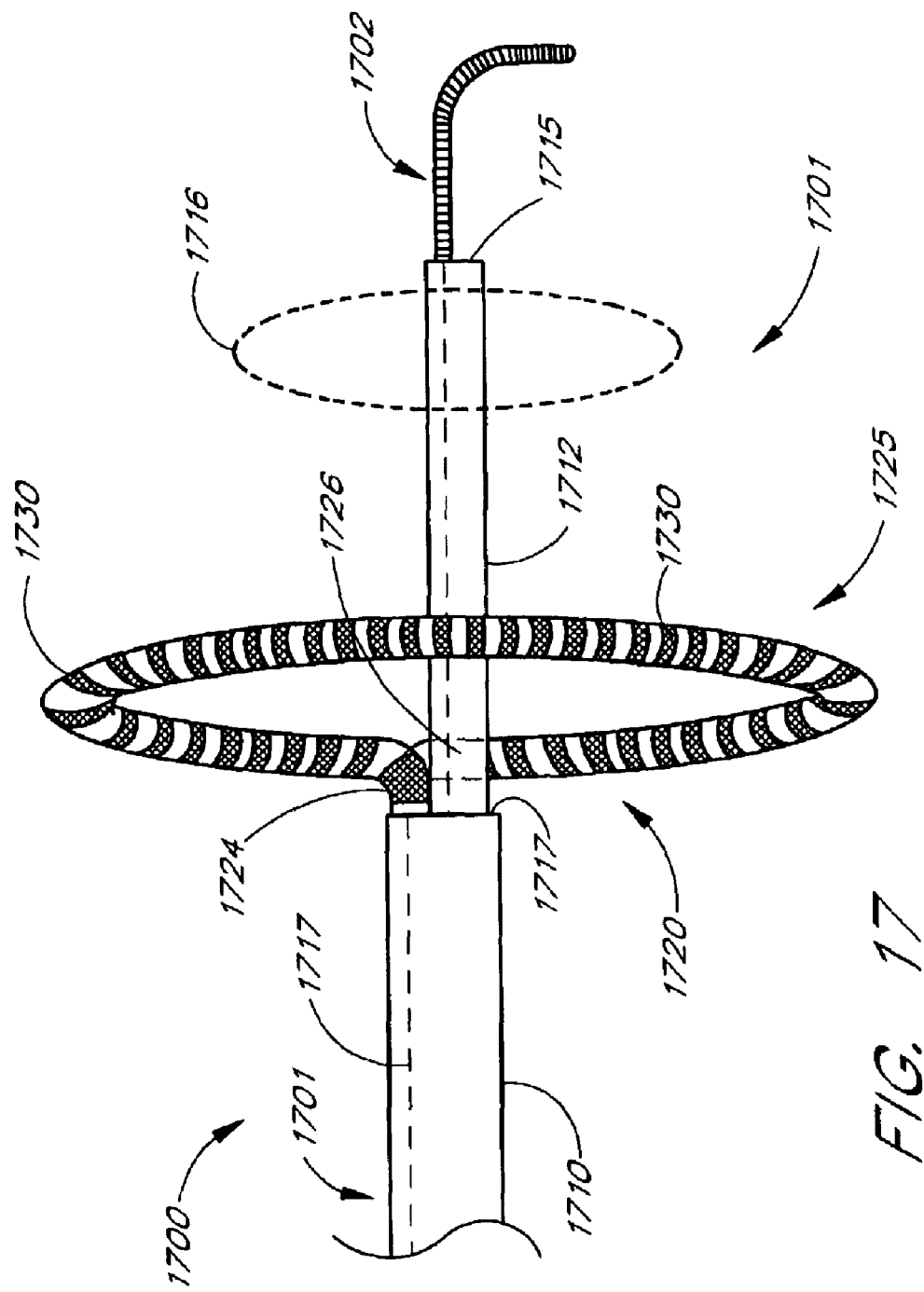
FIG. 17 shows a longitudinal perspective view of another circumferential ablation device assembly having a circumferential ablation member with an ablation element along an elongated member adjusted to a looped shape in order to ablate a circumferential region of tissue according to the invention.

Circumferential ablation device assembly 1700 shown in FIG. 17 also includes a plurality of individual ablation elements 1730 along an elongated member 1725 that is adjusted to a looped shape in order to position individual elements 1730 about a circumference to form the circumferential ablation element 1731 according to the invention. However, according to the FIG. 17 embodiment, elongate member 1725 is provided along a distal end portion of a pushing member (not shown) that is slideably engaged within a passageway 1717 extending proximally along catheter body 1710. In addition, a distal member 1712 extends distally from catheter body 1710 and beyond the circumferential ablation member 1720 in order to track over guidewire 1702 slideably engaged in guidewire passageway 1715 and anchor distally within the pulmonary vein while circumferential ablation member 1720 engages and ablates a circumferential region of tissue where the vein extends from the atrial wall, and in particular along the atrial wall and surrounding the vein ostium. A balloon 1716 is also shown in FIG. 17 in shadow in order to assist in such anchoring by securing distal member 1712 in a desired position distally within the vein. The looped shape for elongate member 1725 is further shown to encircle distal member 1712 and desirably the distal tip 1726 of elongate member 1725 terminates in the looped shape near a proximal portion 1724 of elongate member 1725 in order to facilitate formation of complete and continuous circumferential lesions. It is further contemplated that the distal end portion of elongate member 1725, such as the tip 1726, may be secured to distal member 1712 in order to facilitate adjusting elongate member 1725 to a repeatable looped shape during use. According to one aspect of the FIG. 17 embodiment as just described, catheter 1701 may be secured in position, such as by inflating a balloon 1716 within a pulmonary vein, while circumferential ablation member 1720 is advanced distally and adjusted as desired relative to the catheter in order to form the desired lesion.

Circumferential ablation device assembly 1800 shown in FIG. 18 provides a plurality of individual ablation elements, similar to the wire cage illustrated and described with reference to FIG. 14. The individual ablation elements (not shown) are disposed along splines of a braided cage in order to form a circumferential ablation member 1820 according to the invention. Braided cage 1825 is adjustable between radially collapsed and expanded conditions by longitudinally collapsing distal and proximal ends 1824,1826 such as previously described above. Moreover, braided cage 1825 may be further adapted such that a pronounced "forward-looking" circumferential wall 1826 is formed along one region of the braid. By providing the ablation elements in a circumferential pattern along that region, a circumferential ablation element is formed for advancing against tissue for ablation, such as against a posterior left atrial wall to ablate around a pulmonary vein ostium. One such shape incorporating a forward-looking face of the braided cage is shown for the purpose of illustration in shadow in FIG. 18. In one aspect of this embodiment, the pitch, pattern, or physical quality of the splines in the braided network may be varied in order to selectively control the shape of different regions of the braid as its ends are longitudinally collapsed.

It is further contemplated that braided cages such as the types just described may be also used in combination with an inner or outer wall, such as a flexible polymeric wall, in order to expand an enclosed structure into a desired shape for ablation. Such a composite expandable member provides a suitable substitute to the inflatable balloon ablation embodiments herein shown and described.

Circumferential ablation device assembly 1900 shown in FIG. 19A forms a circumferential ablation element by providing a plurality of individual ablation elements along a plurality of radially adjustable spline members 1925 that are formed between longitudinal grooves that are cut along a tubular wall 1911 extending at least in part along the distal end portion of catheter body 1910. A distal end 1913 of tubular wall 1911 is secured to an inner member 1912 that extends proximally of the spline members and within a passageway extending to the proximal end portion of catheter body 1910. By advancing tubular wall 1911 distally with respect to inner member 1912, distal and proximal ends 1924,1926 of the splines are longitudinally collapsed toward each other, thereby deflecting the middle portions of the splines radially outwardly. As such, the individual ablation elements are adjusted from a first position (shown in FIG. 19A) to a second position (shown in FIG. 19B) wherein they are collectively arranged about a circumference to form a circumferential ablation element. Ablation elements 1930 are shown in FIG. 19B in a second position located at the outer periphery of the radially outwardly deflected splines. However, the ablation elements may be arranged on other regions of the splines to allow for the formation of circumferential lesions of different circumferential regions of tissue. In one alternative, for example, an individual ablation element 1930' may be supported at a location along one of the splines, positioned on the distally facing portion of the spline 1925 in the second position, thereby forming a circumferential ablation element adapted to ablate tissue confronted by the splines as the assembly is advanced distally, such as for example against a posterior left atrial wall to ablate tissue surrounding a pulmonary vein.

Other alternative spline configurations to that just described for FIGS. 19A–B are contemplated which are adapted to position individual ablation elements along a circumferential pattern to form a circumferential ablation element for ablating tissue along or surrounding a pulmonary vein ostium according to the invention.

Figure 20A:
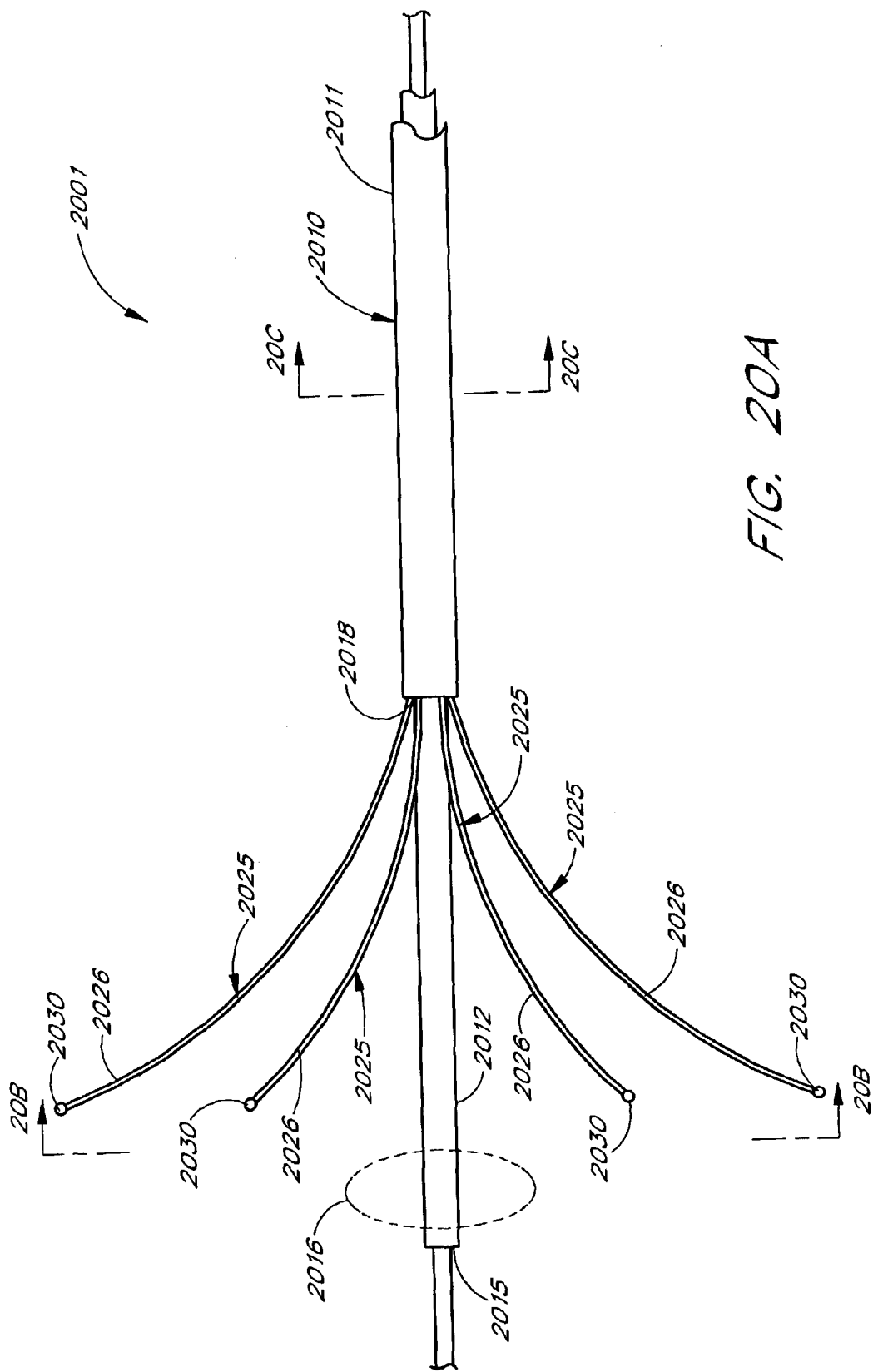
FIG. 20A shows a longitudinal side perspective view of another circumferential ablation device assembly having a plurality of ablation elements on the distal ends of a plurality of longitudinally oriented spline members extending distally from a delivery sheath and also radially with a shape that positions the ablation elements along a circumferential pattern to form a circumferential ablation element according to the invention.

For example, circumferential ablation device assembly 2000 shown in FIGS. 20A–C provides each of a plurality of ablation elements on the distal end portions 2026 of a plurality of longitudinally oriented spline members 2025. During use in a left atrium or pulmonary vein ostium according to the invention, these spline members 2025 extend distally from a delivery passageway 2017 (shown in FIGS. 20B & C) of a catheter body 2010 with a shape that extends radially outwardly from the longitudinal axis of catheter body 2010. Ablation elements 2030 are thereby positioned by spline members 2025 along a circumferential pattern about a radius R (FIG. 20B) in order to form the desired circumferential ablation element for ablating along or around a pulmonary vein ostium according to the invention.

More specifically to the components of assembly 2000 shown in FIGS. 20A–C, a delivery assembly 2000 includes an outer member 2011 that is a tubular member coaxially surrounding an inner member 2012 that is also a tubular member extending distally from a distal port 2018 of outer member 2011. A coaxial space is formed between outer and inner members 2011,2012 and provides a delivery passageway 2017 within which spline members 2025 are positioned in a circumferential array (FIGS. 20B & C). Inner member 2012 includes a guidewire passageway 2015 for slideably engaging and tracking over a guidewire. A balloon 2016, or other expandable member, is shown in shadow in FIG. 20A on the distal end portion of inner member 2012 and may be used in one aspect to help anchor inner member 2012 within a pulmonary vein after inner member 2012 is tracked into the vein over guidewire. As such, FIGS. 20B–C show inner member 2012 to also include a second passageway as an inflation lumen 2014 in order to inflate such a balloon 2016.

The configuration shown in FIGS. 20A–B represents a second position for the ablation elements 2030. However, in a different mode of operation during delivery to the left atrium (not shown), the distal end portions 2026 of spline members 2025 are radially confined in a longitudinal orientation within delivery passageway 2017 (FIG. 20C). Accordingly, ablation elements 2030 are thus located in a first position that is radially collapsed in relation to the second extended position through delivery member 2010. The ablation elements 2030 in the first position may remain distal to distal port 2018, such as for example if ablation elements are too large to be withdrawn through distal port 2018. Or, the respective sizes for ablation elements 2030 or delivery passageway 2017 may be specifically configured to allow for the ablation elements 2030 to be withdrawn into and housed within delivery passageway 2017 in the first position during delivery to the left atrium.

FIG. 20B further shows alternative "+" and "−" symbols associated with each of the ablation elements 2030, one mode of this embodiment wherein ablation elements 2030 provide an assembly of bipolar electrodes. As such, electrical current flows through tissue extending between adjacent pairs of oppositely poled electrodes, thereby ablating that tissue. By ablating tissue between all such poled pairs, a circumferential lesion may be formed according to the invention. Further, such bipolar ablation about the circumferential region of tissue may be accomplished in one aspect by actuating all electrodes at once. Or, various combinations of adjacent electrodes thereof may be gated for actuation only during discrete periods of time during an overall ablation procedure. For example, by actuating all at once, current flowing through any given positively poled electrode of the array would be divided along tissue in each opposite direction to both adjacent negatively poled electrodes. However, by providing varied duty cycles for each bipolar pair, current may be isolated between two adjacent poles while others of the poles are not actuated or are left "open" and out of the circuit. Moreover, it is further contemplated that the ablation elements according to this embodiment may also be monopolar electrodes or other types of ablation elements as would be apparent to one of ordinary skill based upon this disclosure.

Other spline member configurations than that specifically shown in FIGS. 20A–C for assembly 2000 are also contemplated. For example, FIGS. 21A–C variously show similar assemblies to that shown in FIGS. 20A–C, but with some specific aspects varied. More specifically, each of FIGS. 21A–C show a higher number of spline members 2125 and associated ablation elements 2130. This embodiment illustrating that closer spacing may be required in some circumstances over a given circumference. Or, alternatively this illustrates that more ablation elements may be needed in order to maintain the requisite spacing between the individual elements so that a continuous circumferential lesion may be formed along circumferential regions of tissue with greater radii.

The distal end portions 2126 of spline members 2125 shown in FIG. 21A illustrate different arcuate shapes that are curved about an inflected radius relative to the corresponding shapes shown for the corresponding spline members for example in FIGS. 20A or 20C. This illustrates that one shape may be preferred for different specific lesions to be formed. More specifically, the shapes shown in FIGS. 20A and 21C may be preferred for ablation within a pulmonary vein ostium or vein, such that the curved spline members terminate with a bias that points radially outwardly from the long axis of the assembly and outward toward the associated wall to be ablated. In contrast, the shape shown in FIG. 21A has an inflected radius of curvature relative to the FIG. 20A/21C embodiments, such that the distal end portions of spline members 2125 are oriented with a longitudinal bias adapted to force ablation elements 2130 distally relative to the longitudinal axis L of the assembly, such as against a posterior left atrial wall in order to ablate a lesion surrounding a pulmonary vein ostium.

Circumferential ablation device assembly 2200 shown in FIG. 22A illustrates a further aspect of the invention wherein ablation elements instead extend between support structures such as the various strut or spline members herein shown and described. According to this aspect, ablation element 2230 has each of its ends 2232,2234 coupled to a supporting spline member 2225 which is adapted to adjust the ablation element 2230 from first to second positions for delivery into the atrium and circumferential ablation, respectively, in a similar manner as previously described above. While this design is believed to be suitable for either bipolar or monopolar ablation according to a specific electrode application for the ablation element, it is believed to be particularly well suited for circumferential ablation using the electrode ablation elements in the monopolar fashion. Moreover, it is further believed that providing these ablation elements in a substantially linear, non-preshaped structure, they would tend to string linearly between their ends between the spline members, yielding a pattern for example such as is shown in FIG. 22B. Such pattern with substantially flat, linear lesion portions however may be limited in that spline members adjusted radially outward to radius R results in a circumferential ablation that is limited to surround only circumferential regions, such as a pulmonary vein ostium, along a shorter radius R'. Therefore, in some instances, pre-shaped ablation elements may be desired for adjusting the pattern of the circumferential ablation element as defined along the ablative members extending between spline members, such as is shown in FIGS. 24A–B below.

Figure 23A:
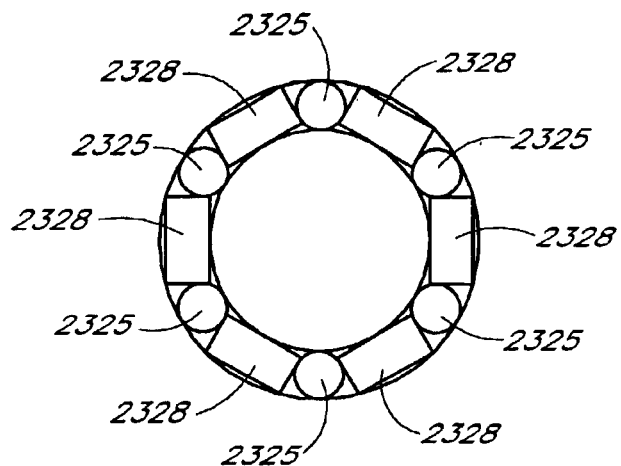
FIGS. 23A–D show various transverse cross-sectional views of various particular embodiments for engaging the spline members within a delivery sheath such as for use according to the assemblies shown in FIGS. 20A, 21A, and 22A.
Figure 23B:
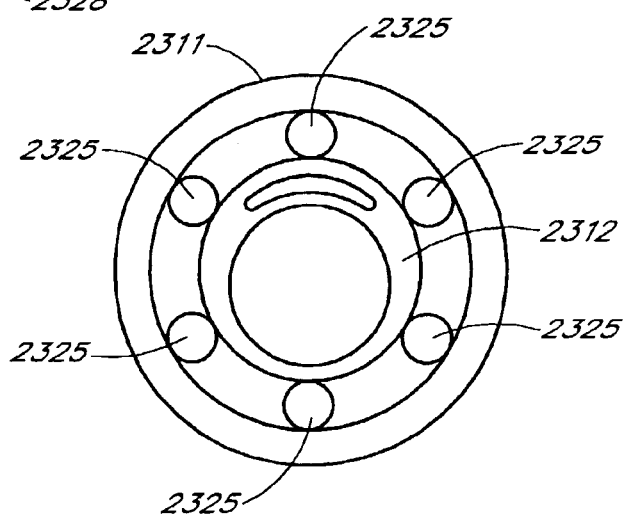
Figure 23C:
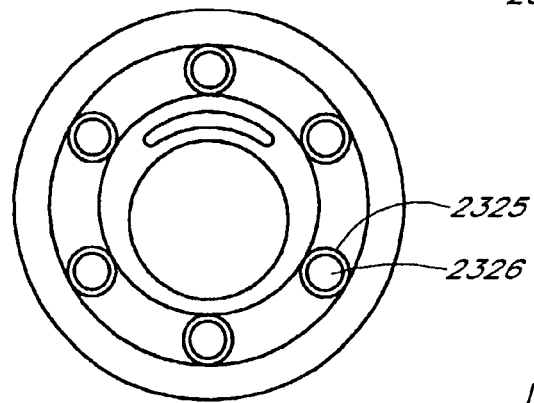

Lines 23—23 shown in FIG. 22A are provided to illustrate that the various transverse cross-sectional views shown in FIGS. 23A–C show catheter body or shaft structures that may be suitable for use according to the FIG. 22A embodiment, though these cross-sectioned shaft structures may also be suitable for the other spline member embodiments otherwise herein described for supporting and positioning ablation elements in a circumferential pattern for ablation.

More specifically, the cross-section shown in FIG. 23A shows spline members 2325 which are spaced around a circumference by spacers 2328 that are provided in order to keep the spacing between spline members 2325 controlled. Preferably, this assembly is bonded into a unitary construction along the proximal aspect of the corresponding catheter, such as by soldering the splines and spacers all together, which may be done for example within a removable capture fixture to aid in molding the resulting soldered assembly to the annular construction shown. The soldered proximal aspect and unsoldered distal aspect of this spline/spacer assembly are positioned within a coaxial space between outer and inner tubing of the elongate catheter body of the overall catheter assembly, such as between outer tubing 2311 and inner tubing 2312 shown in FIGS. 23B and 23C. The outer tubing 2211 may have a diameter of about 0.120 inches. Further, the coaxial space may have a radial length of approximately 0.015 inches. FIG. 23B shows a cross sectional view taken of such an assembly as that shown in FIG. 23A, although taken along the catheter distally beyond where the spacers terminate, and further shows that the coaxial space within which the assembly may be formed may surround an inner catheter shaft 2312 having multiple lumens, such as for example lumens for engaging a guidewire, inflating a distal balloon, actuating the corresponding ablation elements, etc. The inner catheter shaft 2312 may have a diameter of about 0.042 inches.

FIG. 23C also shows a further embodiment wherein hypotube members are used to form spline members 2325' and provide an internal lumen 2326 that extend along spline members 2325'. These lumens 2326 may be used for example to deliver coupling members such as wires to the ablation element(s) supported by the spline members 2325', or fluid such as for electrode cooling or fluidly coupled ablation such as chemical ablation or fluid-assisted electrical ablation, or may carry other elements of the overall assembly such as thermocouple leads. In one highly beneficial aspect of this embodiment, such hypotubes may be constructed of a metal, such as stainless steel or nickel titanium alloy, though the scope of the invention should not be held limited as such.

Figure 23D:
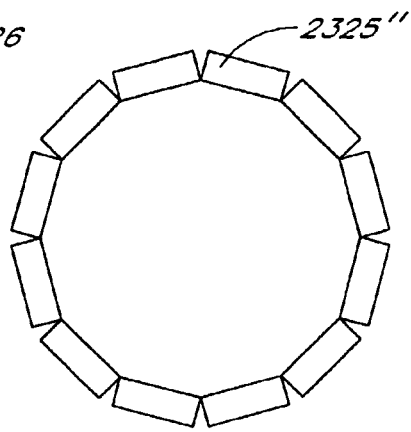

A cross-section of a further assembly is shown in FIG. 23D in order to show a further embodiment wherein a plurality of flattened members may be used as spline members 2325" according to the respective "spline" embodiments herein described, and may provide a highly compact assembly of such members with relatively low radial profile as is shown dimensionally in FIG. 23D. Flattened spline members 2325" are also believed to have preferential bending moment in the radial plane, with high structural integrity out of that plane for providing a high degree of support during ablation.

The spline members 2325 employed in the embodiments illustrated in FIGS. 23A–D may have diameters in the range of about 0.010 to about 0.020 inches, more preferably ranging from about 0.013 to about 0.015 inches. Where the spline members are hypotubes, as shown in FIG. 23C, or formed from rolled flattened sheets, as shown in FIG. 23D, the wall thickness of the spline members may vary from about 0.001 to about 0.005 inches. In the embodiment shown in FIG. 23A, the spacers 2328 may have separate the spline members by approximately 0.010 to about 0.040 inches, depending on the number of spline members used.

FIG. 24A shows another "splined" circumferential ablation member 2420 which has a circumferential ablation element 2428 comprised of a plurality of ablation elements 2430 provided along respective shaped elongate members 2432 extending between spline members 2425. A shaped elongate member 2432 is adapted support the ablation elements in a generally circular circumferential pattern with an inner radius that is limited by the position of the supporting spline member, as shown in FIG. 24A, and is delivered to and from the atrium in a radially collapsed condition with the circumferential ablation member 2420 folded into a desired "convoluted" shape and the ablation elements 2420 in first positions which are adapted for delivery in and out of a delivery sheath (not shown), as is shown in FIG. 24B. The shaped elongate member 2432 may be a single unitary hoop as shown, or it may be formed from segments that are attached to the ends of each spline member 2425. As shown in FIG. 24C, the shaped elongate member 2432 is actually integrated portions of a continuous substantially circumferential, preshaped member that is merely engaged between portions by the individual spline members. Further to FIG. 24C, such spline member 2425 is shown to have an eyelet 2426 that forms a loop through which elongate member 2432 is threaded. The position of spline member 2425 may be limited along elongate member 2432 such as by adhering the two structures together, such as with adhesive or soldering, though this is believed to be potentially limiting in the maneuverability of these components relative to each other during operation between multiple positions and configurations of the assembly. Alternatively, the spline members may be linked to the elongate member by any flexible articulation known in the art, such as for example interlocking eyelets, rings, sutures, etc. To provide flexibility in deployment from the collapsed position to the radially expanded position, the eyelet 2426 shown in FIG. 24C, is left somewhat freely engaged around and is rotatable about elongate member 2432, and is limited against substantially moving its lateral position along elongate member 2432 by individual ablation elements 2430 which are discrete elements provided between spline members along elongate member 2432.

The overall combination of spline members 2425, ablation elements 2430, elongate member 2432, and cooperating engagement between elongate member 2432 and spline members 2425, through eyelets 2426, cooperate to form circumferential ablation member 2420. Moreover, circumferential ablation member 2420 is specifically shown in FIG. 24A with the spline members 2425 adjusted radially deflected condition so as to position ablation elements 2430 along a circumferential pattern to form circumferential ablation element 2428. However, FIG. 24B illustrates ablation member 2420 with ablation elements 2430 in another position which is adapted for delivery into and from the left atrium, such as through delivery sheath 2410. This position for ablation elements 2430 results from adjusting spline members 2425 to a relatively radially collapsed condition, such as after withdrawing spline members 2425 within the radially confining delivery passageway 2417 of sheath 2410. The specific embodiment shown in FIG. 24B shows elongate members and ablation elements in a relatively folded configuration relative to the circumferential patterned position in FIG. 24A, wherein these folded ablation structures extend longitudinally away from the eyelets 2426 and terminate distally at peaks 2437 as the assembly is withdrawn or advanced in and out of sheath 2410.

It is to be appreciated that various ablation elements herein generally described above may be suitable substitutes for use with the assembly just described by reference to FIGS. 24A–B, wherein coiled electrode ablation elements are specifically shown in FIG. 24C. In particular with respect to that embodiment, various electrical conductors or wires (not shown) are also to be included in the overall catheter assembly which electrically couple to and extend from each electrode and extend proximally from ablation member 2420 and along delivery sheath 2410 and/or catheter body 2411 to a proximal electrical coupler for coupling to an electrical current source, preferably an RF current source (not shown). The ablation elements 2430 may be helical or spiral electrodes or any other electrode configurations known in the art.

For further illustration, FIG. 24D shows another type of ablation element 2428' incorporating a porous membrane 2460 over electrode elements 2430 which are further provided over arcuate shaped support member 2432 extending between spline members (not shown). Electrode elements 2430 are electrically coupled to tissue via electrically conductive fluid flowing through voids or pores in porous membrane 2460 and into tissue in contact therewith. Therefore, in addition to the electrical coupling assembly as previously described above, this embodiment further requires a fluid coupling to ablation element 2428', which may be accomplished in one regard for example through the associated spline members, to the extent that they may be tubular such as hypotubes as elsewhere herein described, or via other communicating members or tubing extending between the positioned circumferential ablation element and the associated delivery catheter assembly. Furthermore, such a fluid coupling aspect of this embodiment further includes a proximal coupler that is adapted to couple to a pressurizeable source of such an electrolytic fluid (not shown).

As would be apparent to one of ordinary skill from this disclosure, similar ablation element/actuator subassemblies, such as including individual electrodes and associated electrical conductors/couplers, or including fluid electrodes and associated electrical and fluid couplers, are also considered applicable to others of the various embodiments illustrated, though they may not be specifically shown or described with reference thereto. The use of thermocouples to monitor ablation temperature in the embodiments of the ablation devices are considered applicable.

Figure 24F:
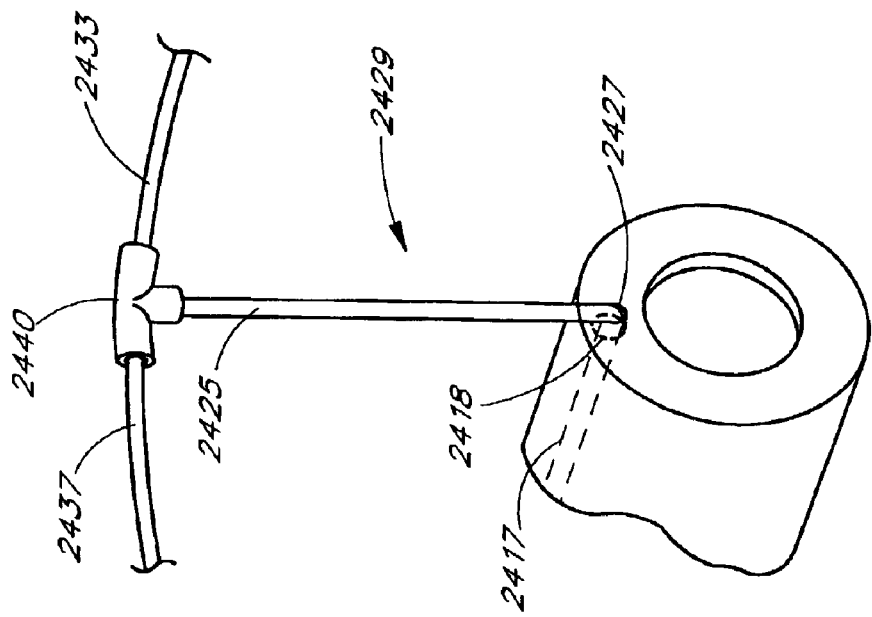
FIG. 24F shows a perspective view of T-coupling between a spline member and an arcuate shaped ablation element.
Figure 24E:
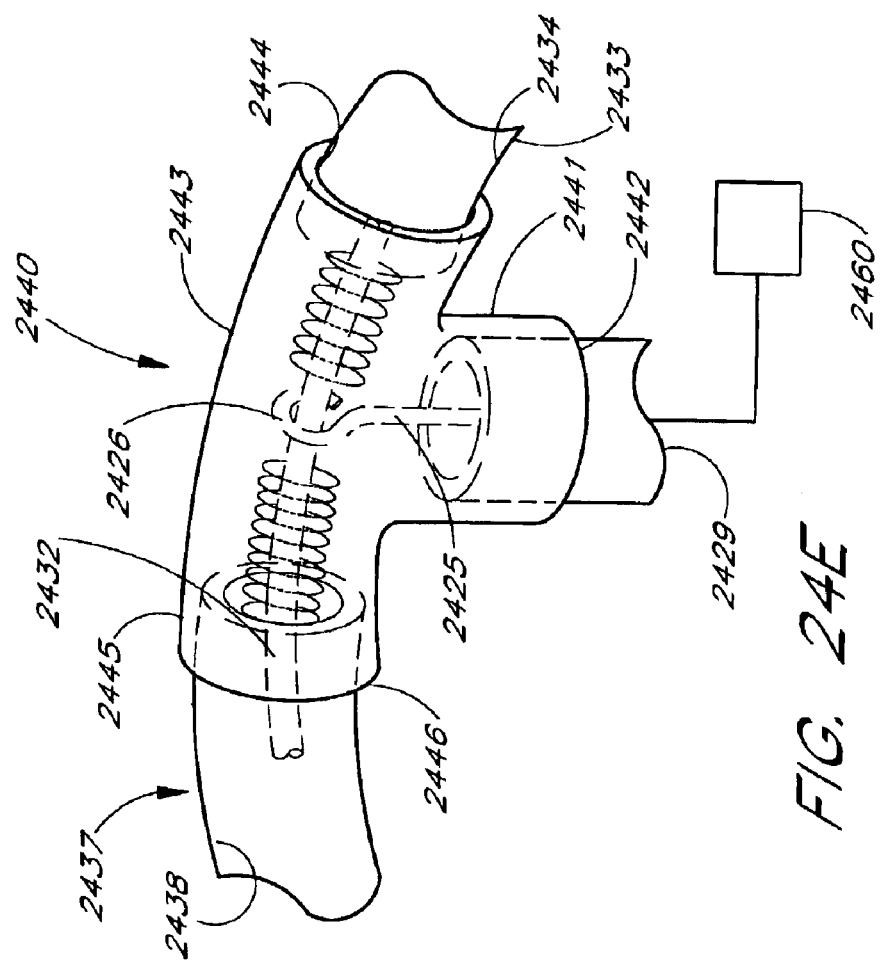
FIG. 24E shows an expanded perspective view of a fluid coupling between a spline member and the porous membrane over an arcuate shaped ablation element.

FIGS. 24E–F show still a further illustrative embodiment for coupling a circumferential ablation element 2435 to associated spline members and actuating members in order to form a circumferential ablation member such as that shown in FIGS. 24A–B. More specifically, spline member 2425 is coupled to shaped elongate member 2432 via eyelet 2426 in much the same threaded manner as previously described for FIG. 24C. However, in the embodiment shown in FIG. 24E, a "T"-joint coupler 2440 is further provided over the spline member/elongate member coupling in order to fluidly couple a pressurized fluid source 2460 to interior spaces 2434,2438 defined by porous membranes 2433,2437, respectively, which surrounding elongate member 2432 on either side of eyelet 2426. More specifically, coupler 2440 has a first leg 2441 forming a first bore 2442 that receives in a fluid tight seal fluid tubing 2429 which coaxially surrounds spline member 2425. First leg 2441 terminates in fluid communication with second and third legs 2443,2445. These second and third legs 2443,2445 form bores 2444,2446 which receive, in a fluid tight seals, terminal ends of porous members 2433,2437, also respectively. Accordingly, fluid tubing 2429 is provided in fluid communication with the interior spaces 2434,2438 of porous membranes 2433, 2437, respectively, via coupler 2440.

As shown in further detail in FIG. 24F, fluid tubing 2429 and spline member 2425 couple with catheter body 2410 through port 2418 and extend proximally through body 2410 through passageway 2417 and terminate proximally in respective couplers (not shown) for actuating the position for spline member 2425 and pressurizing fluid tubing 2429 with fluid. It is to be appreciated that such fluid may be for example a chemical ablation fluid such as alcohol. Or, such fluid may be an electrically conductive fluid in the instance that electrode elements (not shown) are further provided for driving current into interior spaces 2434,2438 of porous membranes 2433,2437, respectively, as would be apparent to one of ordinary skill from this disclosure.

Other moveable engagement means are contemplated as suitable substitutes for the specific "eyelet" embodiment shown in FIG. 24C. One such alternative means is shown in various modes in FIGS. 25A–B, wherein spline members 2525 terminate proximally in balls 2536 which couple to receivers 2526 in a "ball-in-socket" type of coupling that allows for a predetermined range of relative movement between these components to allow for the transition between radially collapsed and expanded or extended conditions for spline members 2525 and the corresponding first and second positions for ablation element 2530 (compare FIGS. 25A and B, respectively).

Additional variations for the spline members are further contemplated as suitable substitutes for those previously described above, such as by specific reference to spline members 2425 shown in FIG. 24A.

One such illustrative embodiment is shown in FIGS. 26A–B, wherein spline members 2625 are provided with predetermined arcuate and convoluted shapes. More specifically, FIG. 26C shows in detail spline member 2625 which is constructed from a shaped member 2621 having two legs 2622,2624 extending in a side-by-side relationship between proximal end portion 2627 and distal end portion 2628 of spline member 2625. Shaped member 2621 forms an acute bend or loop between legs 2622,2624 at distal end portion 2628. Circumferential ablation element 2635 is threaded through a plurality of such loops formed by multiple such spline members 2625 about a circumferential pattern, as shown in a first configuration in FIG. 26A. The ablation element may comprise a plurality of individual ablation electrodes 2630 as illustrated, or alternatively, the ablation element may comprise a continuous ablation coil or helix, as illustrated with reference to FIG. 24A. This assembly is further collapsible through a delivery catheter 2610, as shown in FIG. 26B, in which configuration the circumferential ablation element 2635 may form convoluted folds 2635' extending proximally from distal ends 2628 to proximal ends 2627 of spline members 2625, as shown in greater detail in FIG. 26C. Or, such folds may extend away from spline members 2625, such as in a similar manner to that shown in FIG. 24B. The desired folded configuration may be controlled, such as for example by forming a preshaped bias or memory to the circumferential ablation element that is elastically deflected into the circumferential pattern by the corresponding spline members, or in another example by providing tethers to pull on portions of the ablation element such as in order to yield the folded geometry of FIG. 26C. Furthermore, in some instances the mechanical action of retracting spline members within the corresponding delivery sheath or catheter may cause the folds to "groom" into the configuration shown in FIG. 24B, since the splines are effectively pulling the ablation element into the sheath.

The specific geometry shown and just described for spline members 2625 by reference to FIGS. 26A–C is also believed to be beneficial for adapting the desired circumferential ablation element to ablate regions of tissue against the posterior left atrial wall and surrounding a pulmonary vein. More specifically, the side-by-side leg configurations bordered in the middle by a bended loop is believed to provide a robust support structure along the plane along which the circumferential ablation element is patterned. Notwithstanding this feature, however, such shaped spline structures may be further provided with angled orientations out of the plane of the resulting circumferential ablation element's shape without departing from the scope of the invention. Additionally, the opposing concavity and convexity of the reciprocally shaped legs provides wider base of their separation along the proximal and distal end portions 2627,2628 than along a mid region 2626, such that there is robust support along the proximal and distal end portions, but an overall flexibility provided by the mid region 2626.

A further circumferential ablation member 2720 according to the invention is shown variously in FIGS. 27A–28D and provides a similar assembly of shaped spline members 2725 as that shown in FIGS. 26A–C within a housing 2740 which is adjustable to provide a distal wall 2760 (shown in FIGS. 27C & D) having a circumferential surface 2745 that forms at least in part a circumferential ablation element for ablating tissue surrounding a pulmonary vein ostium according to the invention. More specifically, spline members 2725 are provided between distal wall 2760 and a proximal wall 2750 which are shown in FIGS. 27C & D to be relatively taut opposing faces when spline members 2725 are in a radially extended condition relative to longitudinal axis L of delivery member 2710. By reference to this extended and taut condition shown in FIG. 27A, proximal and distal walls 2750,2760 are sealed together along both an inner circumferential region 2741 and an outer circumferential region 2743 relative to the extended condition for spline members 3125 and corresponding taut condition for housing 2740 shown in FIG. 27A.

Figure 27A:
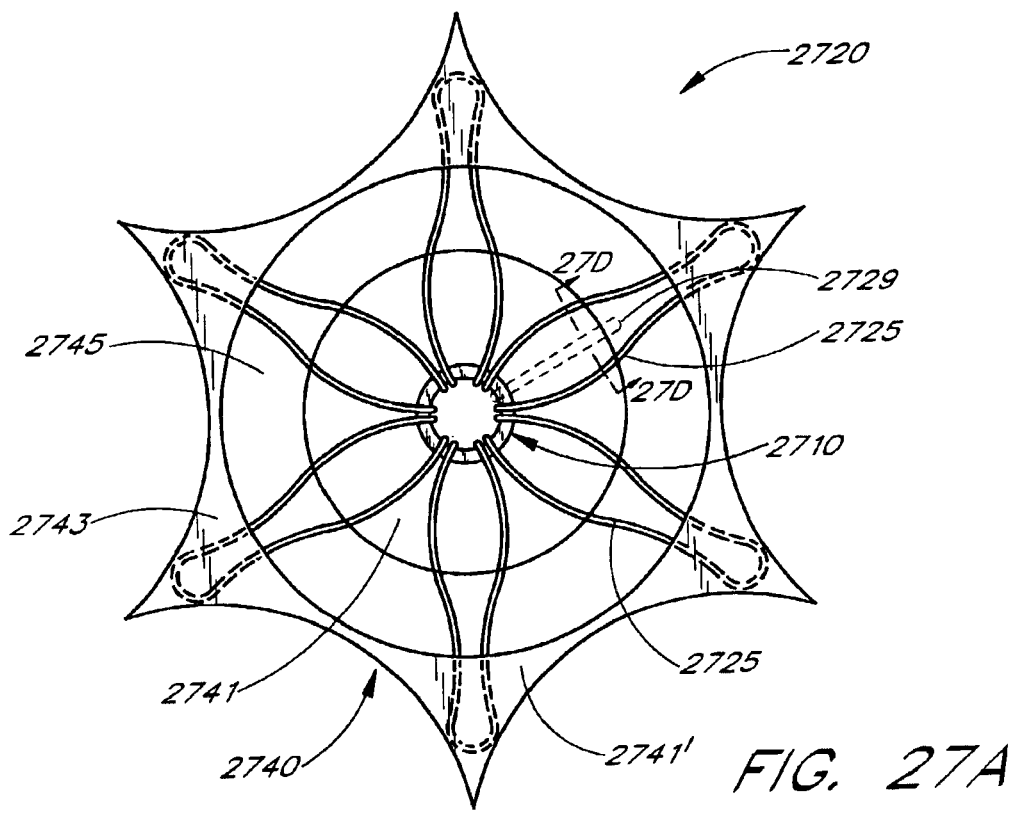
FIG. 27A shows an end view of another circumferential ablation device assembly having a plurality of shaped splines such as those shown in FIGS. 27A–C, although showing the circumferential ablation element formed along a circumferential region along a distally disposed surface of a forward wall that is supported in the position shown by the spline members.
Figure 28A:
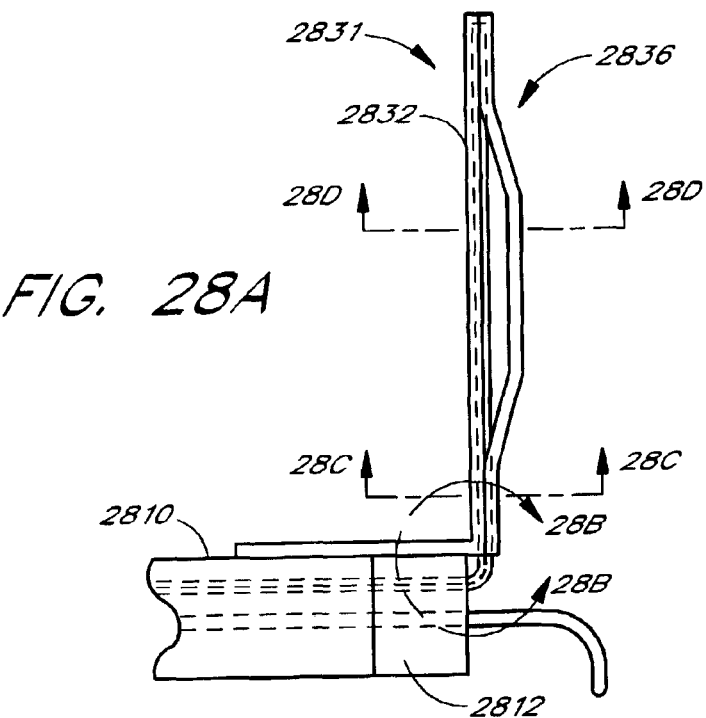
FIG. 28A shows a partially longitudinally cross-sectioned view of another circumferential ablation member which is similar to that shown in FIGS. 27A–E, except showing a tip region of the catheter body extending further distally than that shown in FIG. 27D, and showing radially spaced inner and an outer seal between the forward and rearward walls that form a sealed void space along the circumferential region of the forward wall along which the circumferential ablation element is formed.

The proximal 2750 and distal 2760 walls are not sealed to one another in the intermediate circumferential region 2745 between the sealed inner and outer portions 2741, 2743, respectively, along this radius, yielding a void space between the walls in that circumferential region, but for the presence of the spline members 2725 which extend between all three of the respectively sealed and unsealed regions as shown in FIG. 27A. Distal wall 2760 is porous along the unsealed circumferential region 2745. In a variation of this embodiment, shown in FIGS. 28A and 28D, the void space is created in the unsealed circumferential region 2845 by a concave region of the distal wall 2860. As shown in greater detail in FIG. 27C, a fluid tubing 2729 is positioned between proximal and distal walls 2750,2760 and terminates along unsealed circumferential region 2745 such that this void space communicates externally of housing 2740 only through fluid tubing 2729 and the pores along the porous portion of distal wall 2760 along that circumference. The same fluid coupling relationship is also illustrated in FIGS. 28A & B. Fluid tubing 2729 and spline members 2725 couple proximally to various lumens or passageways (not shown) provided by delivery member 2710, as shown in part in FIG. 27C, and are further coupled to corresponding actuators as elsewhere herein described.

Figure 27B:
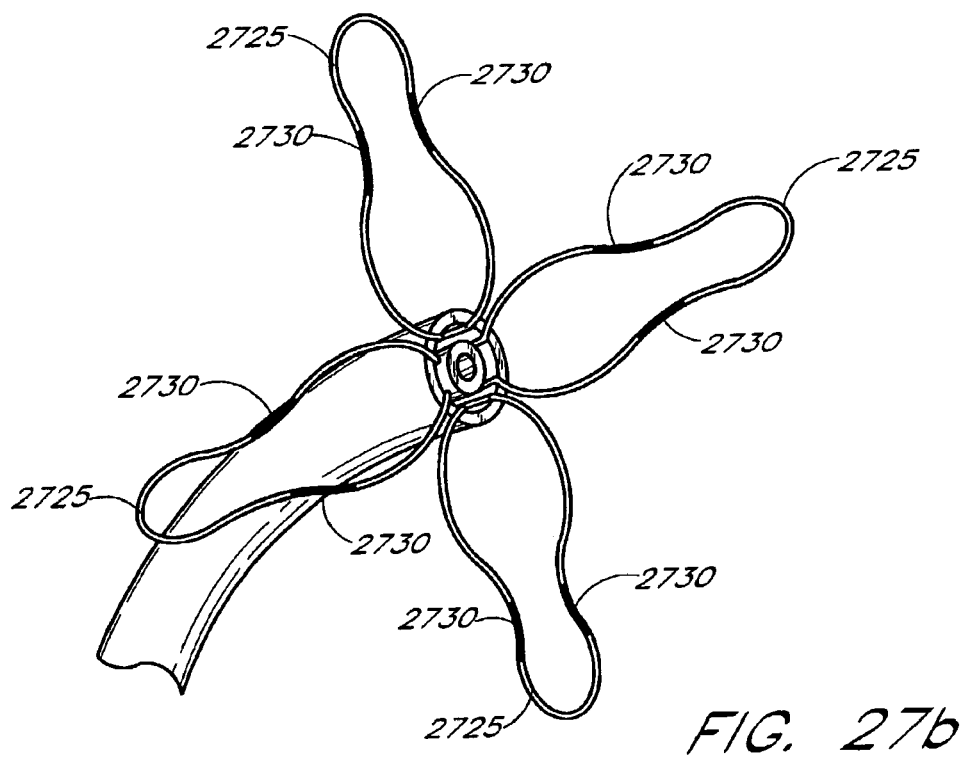
FIG. 27B shows a perspective overview of another circumferential ablation device assembly which is similar to that shown in FIG. 27A, except that the wall is shown to have a different shape around the outer periphery where it extends radially beyond the supporting spline members, and further showing a proximal region of a rear wall of the ablation member where it is sealed onto an outer surface of a catheter shaft and also showing a forward wall sealed along the rear wall along an area which is surrounded by the circumferential region providing the circumferential ablation element.
Figure 27C:
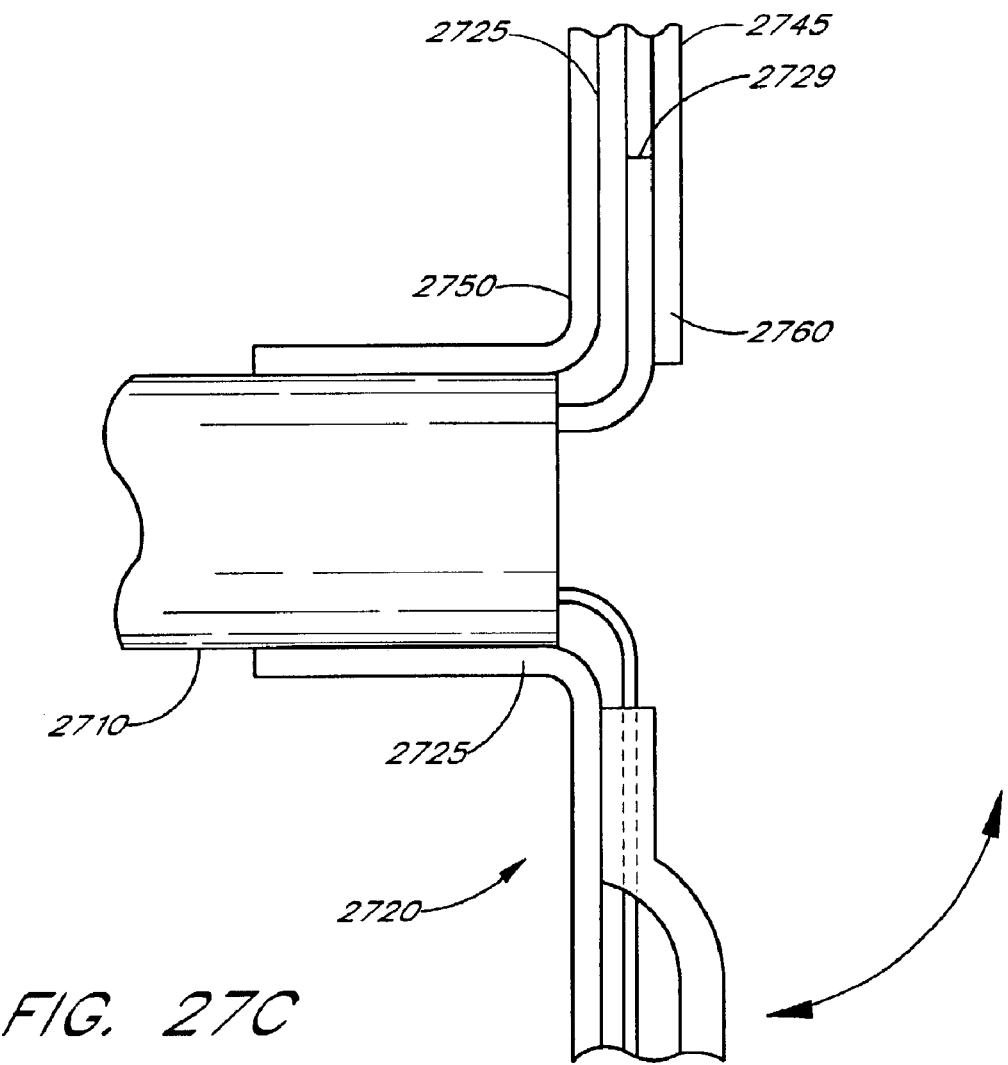
FIG. 27C shows an exploded longitudinally cross-sectioned view of a circumferential ablation device assembly which is similar to that shown in FIGS. 27A–B, and shows where the circumferential ablation member is coupled to the distal end portion of the associated elongated catheter body for delivering the ablation member into the left atrium.
Figure 27D:
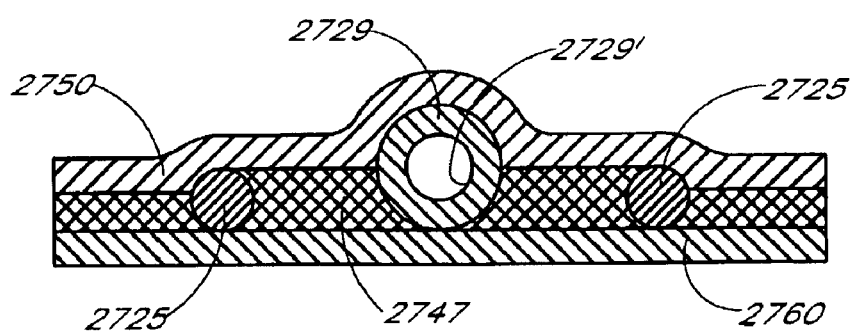
FIG. 27D shows an exploded cross-sectioned view taken along line 27D—27D of FIG. 27C and shows the layered structure at the base of the circumferential ablation member adjacent to the coupling to the elongated catheter body.

Further to the sealed regions 2741,2743 for housing 2740, an adhesive or other sufficient filler material may be used in order to ensure a fluid tight seal around the fluid tubing 2729 and spline members 2725 and between the housing's respectively sealed walls, as shown along intermediate layer 2747 between proximal and distal walls 2750,2760 in FIG. 27D.

When circumferential ablation member 2720 is withdrawn into a delivery sheath (not shown), spline members 2725 are adjusted to a radially collapsed condition which adjusts the housing 2740 to a folded position that is adapted for delivery to and from the atrium for ablation (not shown). Once in the left atrium, spline members 2725 are advanced distally from the delivery sheath in the radially extended condition as shown in FIGS. 27A–B. Accordingly, circumferential region 2745 is positioned to form a circumferential ablation element when an ablative fluid couples to tissue through the porous portion of distal wall 2760 along that region. As previously described for other embodiments, this fluid coupling may include for example a chemically ablative fluid, or may incorporate an electrically conductive fluid energized with current from electrodes, such as shown schematically at electrodes 2730 which are positioned along spline members along the porous and ablative circumferential region 2745. It is further contemplated that the elongated member forming the spline members 2725 themselves may be electrically conductive, such as a conductive metal construction, and provide such electrode function over an above the support and positioning functions otherwise herein described.

Figure 28B:
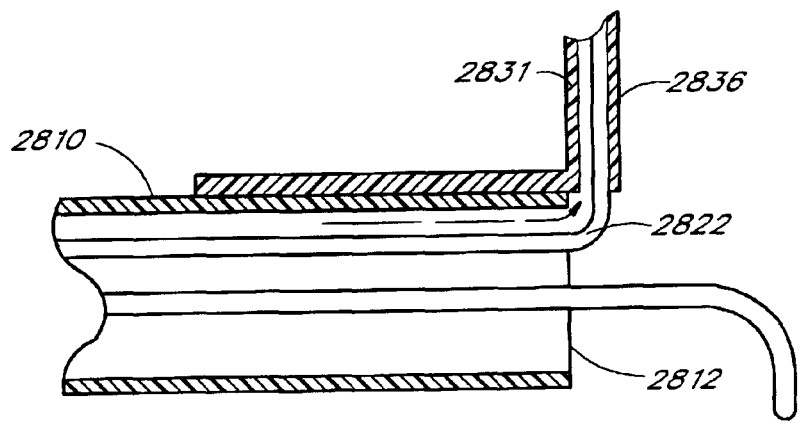
FIG. 28B shows an exploded longitudinally cross-sectioned view of the circumferential ablation member shown in FIG. 28A where it couples to the elongated catheter body.
Figure 28C:
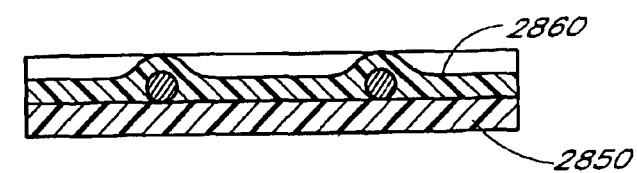
FIG. 28C shows a cross-sectioned view taken along lines 28C—28C of FIG. 28A, and shows an area where two adjacent portions of a spline member are imbedded between the inner seal between the forward and rearward walls.

A further circumferential ablation member 2820 forming an ablative circumferential region along a distal wall of a radially adjustable housing is shown in FIGS. 28A–C. This embodiment however allows for the radial adjustment of a housing 2840 by manipulation of cooperating portions of catheter body 2810 and without the need for withdrawal or advancement of a separate, confining delivery sheath as with the FIG. 26 and FIG. 27 embodiments.

Figure 28D:
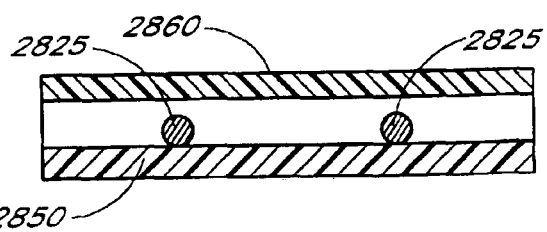
FIG. 28D shows a cross-sectioned view taken along lines 28D—28D of FIG. 28A, and shows an area where two adjacent spline members extend along the void space along the circumferential region where the circumferential ablation element is formed.

With reference to FIGS. 28A & B, a molded insert or tip housing is shown. The housing, which may be constructed out of metal or molded plastic for example, may be used for coupling the circumferential ablation member components to the corresponding catheter, as shown at tip housing 2812 in FIG. 28B. With reference to FIGS. 28C and 28D, the spline members 2825 are shown in cross section extending in an inner circumferential region between the sealed proximal 2850 and distal 2860 walls, and in an outer circumferential region within the void space between these walls.

With reference to FIGS. 29A–30D, other variations of the circumferential ablation device assembly are shown, which include a circumferential ablation member located along a distal end portion of catheter body and includes a housing that forms a porous distal wall that covers the distal end portions of a plurality of spline members. In one embodiment, the distal tip of the elongate or catheter body may include an anchor (e.g., inflatable balloon), and/or a distal port of for a guidewire. Each of spline members includes: a proximal end portion that is secured to outer member of catheter body; a distal end portion that is secured to an inner member extending from within outer member and distally from circumferential ablation member; and a hinge point between corresponding proximal and distal end portions.

As shown in FIG. 29A, by moving outer member 2911 distally with respect to inner member 2912, the respective proximal and distal end portions 2922,2926 of spline members 2925 are adapted to longitudinally collapse with respect to longitudinal axis L of body such that hinge point 2924 deflects radially outwardly from longitudinal axis L. This radial deflection of the spline members 2925 causes a distal wall 2960 covering distal end portions 2926 to be angled with a distal orientation. Distal wall 2960 has a circumferential ablative surface 2961 that is adapted to ablate a circumferential region of tissue in contact therewith. FIGS. 29A & B show that housing 2940 includes proximal and distal walls 2950,2960 which are either separate members secured together or are separately treated portions of one otherwise contiguous, integrally formed member. Proximal wall 2950 covers proximal end portions 2922 of spline members 2925 and is secured in a fluid tight seal over outer member 2911 proximally of circumferential ablation member 2920. Distal wall 2960 covers distal end portions 2926 of spline members 2925 and is secured in a fluid tight seal over inner member 2912 distally of circumferential ablation member 2920. As in previous embodiments, the inner member 2912 is adapted to track over guidewire 2902. The distal end portions 2926 of spline members 2925 are shown in FIG. 29B as incorporating ablation electrodes 2930. A pressurizeable fluid source 2903 is fluidly coupled to an interior space formed by housing 2940 via the co-axial space formed between outer and inner members 2911,2912, as shown schematically in FIG. 29A.

Spline members 2925 may be made by cutting longitudinal grooves into outer member 2911, but should not be limited as such. For example, spline members 2925 may alternatively be separate components secured to outer and inner members 2911,2912, such as for example separate shaped members such as spline members 2625 shown and described by reference to FIGS. 26A and C. Further to that variation, hinge point 2924 may be formed along the more flexible, converging, narrowed separation between separate struts, such as at 2626 shown in FIG. 26C.

In another specific embodiment, the electrode elements 2930 is incorporated along spline members 2925. In this embodiment, distal wall 2960 is porous along circumferential ablative surface 2961, and housing 2940 further includes a backing or proximal wall (not shown) that covers proximal end portions 2922 of spline members 2925.

With reference to FIG. 30A, inner member 3012 includes a fluid passageway terminating in ports 3017 located within housing 3040, and a gasket seal 3013 is provided between outer and inner members 3011,3012 proximally of fluid ports 3017 and ablation member 3020. Accordingly, with the ablation member 3020 in the radially expanded condition and ablative surface 3061 positioned for ablation as shown in FIGS. 30A–C, electrolyte fluid filling housing 3040 can only escape through the porous region along ablative surface 3061, thereby electrically coupling ablation elements 3030 with tissue contacting that surface 3061 such as a circumferential region of tissue surrounding a pulmonary vein ostium.

With reference to FIGS. 30B & C, proximal and distal perspective views are illustrated. The proximal wall 3050 of housing 3040 can be seen in FIG. 30B to substantially cover the proximal surfaces of the spline members (shown in phantom).

Further to the various embodiments just described incorporating housings that are controllably positioned by use of deflectable spline members, the porous wall aspects of such embodiments may be constructed according to several known structures and methods. Porous fluoropolymers such as porous polytetrafluoroethylene (PTFE), and in particular the expanded variety (e-PTFE), may be suitable. In such case, however, the corresponding porous wall would be relatively non-elastomeric, and therefore must be adjusted between folded and taut conditions between the delivery and ablation positions described by reference to the particular embodiments. However, such porous material may also be constructed from an elastomer, such as for example a porous silicone material, which beneficially may have an elastomeric memory to a tubular state in the corresponding delivery position and which stretches to the ablation positions as herein described. Such porous elastomer embodiment is believed to be highly beneficial for use in the embodiments described by reference to FIGS. 33A–34F, wherein the corresponding housing including a porous region may be substantially tubular along the respective catheter assembly. Further to this aspect, it is further contemplated that such housings such as housing 3040 shown in FIGS. 30A–D may be constructed of a contiguous elastomeric tube which has been made porous along only the ablative circumferential surface of the distal wall 3060 in the resulting assembly.

FIGS. 31A–34B show various specific embodiments of a circumferential ablation device assembly that utilizes an ultrasonic energy source to ablate tissue. The present circumferential ablation device has particular utility in connection with forming a circumferential lesion within or about a pulmonary vein ostium or within the vein itself in order to form a circumferential conductive block. This application of the present ablation device, however, is merely exemplary, and it is understood that those skilled in the art can readily adapt the present ablation device for applications in other body spaces.

As common to each of the following embodiments, a source of acoustic energy is provided a delivery device that also includes an anchoring mechanism. In one mode, the anchoring device comprises an expandable member that also positions the acoustic energy source within the body; however, other anchoring and positioning devices may also be used, such as, for example, a basket mechanism. In a more specific form, the acoustic energy source is located within the expandable member and the expandable member is adapted to engage a circumferential path of tissue either about or along a pulmonary vein in the region of its ostium along a left atrial wall. The acoustic energy source in turn is acoustically coupled to the wall of the expandable member and thus to the circumferential region of tissue engaged by the expandable member wall by emitting a circumferential and longitudinally collimated ultrasound signal when actuated by an acoustic energy driver. The use of acoustic energy, and particularly ultrasonic energy, offers the advantage of simultaneously applying a dose of energy sufficient to ablate a relatively large surface area within or near the heart to a desired heating depth without exposing the heart to a large amount of current. For example, a collimated ultrasonic transducer can form a lesion, which has about a 1.5 mm width, about a 2.5 mm diameter lumen, such as a pulmonary vein and of a sufficient depth to form an effective conductive block. It is believed that an effective conductive block can be formed by producing a lesion within the tissue that is transmural or substantially transmural. Depending upon the patient as well as the location within the pulmonary vein ostium, the lesion may have a depth of about 1 to 10 mm. It has been observed that the collimated ultrasonic transducer can be powered to provide a lesion having these parameters so as to form an effective conductive block between the pulmonary vein and the posterior wall of the left atrium.

With specific reference now to the embodiment illustrated in FIGS. 31A through 31D, a circumferential ablation device assembly 800 includes an elongate catheter body 802 with proximal and distal end portions 810,812, an expandable balloon 820 located along the distal end portion 812 of elongate catheter body 802, and a circumferential ultrasound transducer 830 which forms a circumferential ablation member that is acoustically coupled to the expandable balloon 820. In more detail, FIGS. 31A–C variously show elongate catheter body 802 to include guidewire lumen 804, inflation lumen 806, and electrical lead lumen 808. The ablation device, however, can be of a self-steering type rather than an over-the-wire type device.

Each lumen extends between a proximal port (not shown) and a respective distal port, which distal ports are shown as distal guidewire port 805 for guidewire lumen 804, distal inflation port 807 for inflation lumen 806, and distal lead port 809 for electrical lead lumen 808. Although the guidewire, inflation and electrical lead lumens are generally arranged in a side-by-side relationship, the elongate catheter body 802 can be constructed with one or more of these lumens arranged in a coaxial relationship, or in any of a wide variety of configurations that will be readily apparent to one of ordinary skill in the art.

In addition, the elongate catheter body 802 is also shown in FIGS. 31A and 31C to include an inner member 803 that extends distally beyond distal inflation and lead ports 807, 809, through an interior chamber formed by the expandable balloon 820, and distally beyond expandable balloon 820 where the elongate catheter body terminates in a distal tip. The inner member 803 forms the distal region for the guidewire lumen 804 beyond the inflation and lead ports, and also provides a support member for the cylindrical ultrasound transducer 830 and for the distal neck of the expansion balloon, as described in more detail below.

One more detailed construction for the components of the elongate catheter body 802 that is believed to be suitable for use in transeptal left atrial ablation procedures is as follows. The elongate catheter body 802 itself may have an outer diameter provided within the range of from about 5 French to about 10 French, and more preferable from about 7 French to about 9 French. The guidewire lumen preferably is adapted to slideably receive guidewires ranging from about 0.010 inch to about 0.038 inch in diameter, and preferably is adapted for use with guidewires ranging from about 0.018 inch to about 0.035 inch in diameter. Where a 0.035 inch guidewire is to be used, the guidewire lumen preferably has an inner diameter of 0.040 inch to about 0.042 inch. In addition, the inflation lumen preferably has an inner diameter of about 0.020 inch in order to allow for rapid deflation times, although may vary based upon the viscosity of inflation medium used, length of the lumen, and other dynamic factors relating to fluid flow and pressure.

In addition to providing the requisite lumens and support members for the ultrasound transducer assembly, the elongate catheter body 802 of the present embodiment must also be adapted to be introduced into the left atrium such that the distal end portion with balloon and transducer may be placed within the pulmonary vein ostium in a percutaneous translumenal procedure, and even more preferably in a transeptal procedure as otherwise herein provided. Therefore, the distal end portion 812 is preferably flexible and adapted to track over and along a guidewire seated within the targeted pulmonary vein. In one further more detailed construction that is believed to be suitable, the proximal end portion is adapted to be at least 30% stiffer than the distal end portion. According to this relationship, the proximal end portion may be suitably adapted to provide push transmission to the distal end portion while the distal end portion is suitably adapted to track through bending anatomy during in vivo delivery of the distal end portion of the device into the desired ablation region.

Notwithstanding the specific device constructions just described, other delivery mechanisms for delivering the ultrasound ablation member to the desired ablation region are also contemplated. For example, while the FIG. 31A variation is shown as an "over-the-wire" catheter construction, other guidewire tracking designs may be suitable substitutes, such as, for example, catheter devices which are known as "rapid exchange" or "monorail" variations wherein the guidewire is only housed coaxially within a lumen of the catheter in the distal regions of the catheter. In another example, a deflectable tip design may also be a suitable substitute and which is adapted to independently select a desired pulmonary vein and direct the transducer assembly into the desired location for ablation. Further to this latter variation, the guidewire lumen and guidewire of the FIG. 31A variation may be replaced with a "pullwire" lumen and associated fixed pullwire which is adapted to deflect the catheter tip by applying tension along varied stiffness transitions along the catheter's length. Still further to this pullwire variation, acceptable pullwires may have a diameter within the range from about 0.008 inch to about 0.020 inch, and may further include a taper, such as, for example, a tapered outer diameter from about 0.020 inch to about 0.008 inch.

More specifically regarding expandable balloon 820 as shown in varied detail between FIGS. 31A and 31C, a central region 822 is generally coaxially disposed over the inner member 803 and is bordered at its end neck regions by proximal and distal adaptions 824,826. The proximal adaption 824 is sealed over elongate catheter body 802 proximally of the distal inflation and the electrical lead ports 807,809, and the distal adaption 826 is sealed over inner member 803. According to this arrangement, a fluid tight interior chamber is formed within expandable balloon 820. This interior chamber is fluidly coupled to a pressurizeable fluid source (not shown) via inflation lumen 806. In addition to the inflation lumen 806, electrical lead lumen 808 also communicates with the interior chamber of expandable balloon 820 so that the ultrasound transducer 830, which is positioned within that chamber and over the inner member 803, may be electrically coupled to an ultrasound drive source or actuator, as will be provided in more detail below.

The expandable balloon 820 may be constructed from a variety of known materials, although the balloon 820 preferably is adapted to conform to the contour of a pulmonary vein ostium. For this purpose, the balloon material can be of the highly compliant variety, such that the material elongates upon application of pressure and takes on the shape of the body lumen or space when fully inflated. Suitable balloon materials include elastomers, such as, for example, but without limitation, Silicone, latex, or low durometer polyurethane (for example, a durometer of about 80A).

In addition or in the alternative to constructing the balloon of highly compliant material, the balloon 820 can be formed to have a predefined fully inflated shape (i.e., be preshaped) to generally match the anatomic shape of the body lumen in which the balloon is inflated. For instance, as described below in greater detail, the balloon can have a distally tapering shape to generally match the shape of a pulmonary vein ostium, and/or can include a bulbous proximal end to generally match a transition region of the atrium posterior wall adjacent to the pulmonary vein ostium. In this manner, the desired seating within the irregular geometry of a pulmonary vein or vein ostium can be achieved with both compliant and non-compliant balloon variations.

Notwithstanding the alternatives that may be acceptable as just described, the balloon 820 is preferably constructed to exhibit at least 300% expansion at 3 atmospheres of pressure, and more preferably to exhibit at least 400% expansion at that pressure. The term "expansion" is herein intended to mean the balloon outer diameter after pressurization divided by the balloon inner diameter before pressurization, wherein the balloon inner diameter before pressurization is taken after the balloon is substantially filled with fluid in a taut configuration. In other words, "expansion" is herein intended to relate to change in diameter that is attributable to the material compliance in a stress strain relationship. In one more detailed construction which is believed to be suitable for use in most conduction block procedures in the region of the pulmonary veins, the balloon is adapted to expand under a normal range of pressure such that its outer diameter may be adjusted from a radially collapsed position of about 5 mm to a radially expanded position of about 2.5 cm (or approximately 500% expansion ratio).

The ablation member illustrated in FIGS. 31A–D, takes the form of annular ultrasonic transducer 830. In the illustrated embodiment, the annular ultrasonic transducer 830 has a unitary cylindrical shape with a hollow interior (i.e., is tubular shaped); however, the transducer applicator 830 can have a generally annular shape and be formed of a plurality of segments. For instance, the transducer applicator 830 can be formed by a plurality of tube sectors that together form an annular shape. The tube sectors can also be of sufficient arc lengths so as when joined together, the sector assembly forms a "clover-leaf" shape. This shape is believed to provide overlap in heated regions between adjacent elements. The generally annular shape can also be formed by a plurality of planar transducer segments that are arranged in a polygon shape (e.g., hexagon). In addition, although in the illustrated embodiment the ultrasonic transducer comprises a single transducer element, the transducer applicator can be formed of a multi-element array, as described in greater detail below.

As is shown in detail in FIG. 31D, cylindrical ultrasound transducer 830 includes a tubular wall 831 with three concentric tubular layers. The central layer 832 is a tubular shaped member of a piezoceramic or piezoelectric crystalline material. The transducer preferably is made of type PZT-4, PZT-5 or PZT-8, quartz or Lithium-Niobate type piezoceramic material to ensure high power output capabilities. These types of transducer materials are commercially available from Stavely Sensors, Inc. of East Hartford, Conn., or from Valpey-Fischer Corp. of Hopkinton, Mass.

The outer and inner tubular members 833,834 enclose central layer 832 within their coaxial space and are constructed of an electrically conductive material. In the illustrated embodiment, these transducer electrodes 833,834 comprise a metallic coating, and more preferably a coating of nickel, copper, silver, gold, platinum, or alloys of these metals.

One more detailed construction for a cylindrical ultrasound transducer for use in the present application is as follows. The length of the transducer 830 or transducer assembly (e.g., multi-element array of transducer elements) desirably is selected for a given clinical application. In connection with forming circumferential conduction blocks in cardiac or pulmonary vein wall tissue, the transducer length can fall within the range of approximately 2 mm up to greater than 10 mm, and preferably equals about 5 to 10 mm. A transducer accordingly sized is believed to form a lesion of a width sufficient to ensure the integrity of the formed conductive block without undue tissue ablation. For other applications, however, the length can be significantly longer.

Likewise, the transducer outer diameter desirably is selected to account for delivery through a particular access path (e.g., percutaneously and transseptally), for proper placement and location within a particular body space, and for achieving a desired ablation effect. In the given application within or proximate of the pulmonary vein ostium, the transducer 830 preferably has an outer diameter within the range of about 1.8 mm to greater than 2.5 mm. It has been observed that a transducer with an outer diameter of about 2 mm generates acoustic power levels approaching 20 Watts per centimeter radiator or greater within myocardial or vascular tissue, which is believed to be sufficient for ablation of tissue engaged by the outer balloon for up to about 2 cm outer diameter of the balloon. For applications in other body spaces, the transducer applicator 830 may have an outer diameter within the range of about 1 mm to greater than 3–4 mm (e.g., as large as 1 to 2 cm for applications in some body spaces).

The central layer 832 of the transducer 830 has a thickness selected to produce a desired operating frequency. The operating frequency will vary of course depending upon clinical needs, such as the tolerable outer diameter of the ablation and the depth of heating, as well as upon the size of the transducer as limited by the delivery path and the size of the target site. As described in greater detail below, the transducer 830 in the illustrated application preferably operates within the range of about 5 MHz to about 20 MHz, and more preferably within the range of about 7 MHz to about 10 MHz. Thus, for example, the transducer can have a thickness of approximately 0.3 mm for an operating frequency of about 7 MHz (i.e., a thickness generally equal to ½ the wavelength associated with the desired operating frequency).

The transducer 830 is vibrated across the wall thickness and to radiate collimated acoustic energy in the radial direction. For this purpose, as best seen in FIGS. 31A and 31D, the distal ends of electrical leads 836,837 are electrically coupled to outer and inner tubular members or electrodes 833,834, respectively, of the transducer 830, such as, for example, by soldering the leads to the metallic coatings or by resistance welding. In the illustrated embodiment, the electrical leads are 4–8 mil (0.004 to 0.008 inch diameter) silver wire or the like.

The proximal ends of these leads are adapted to couple to an ultrasonic driver or actuator 840, which is schematically illustrated in FIG. 31D. FIGS. 31A–D further show leads 836,837 as separate wires within electrical lead lumen 808, in which configuration the leads must be well insulated when in close contact. Other configurations for leads 836, 837 are therefore contemplated. For example, a coaxial cable may provide one cable for both leads that is well insulated as to inductance interference. Or, the leads may be communicated toward the distal end portion 812 of the elongate catheter body through different lumens that are separated by the catheter body.

The transducer also can be sectored by scoring or notching the outer transducer electrode 833 and part of the central layer 832 along lines parallel to the longitudinal axis L of the transducer 830, as illustrated in FIG. 31E. A separate electrical lead connects to each sector in order to couple the sector to a dedicated power control that individually excites the corresponding transducer sector. By controlling the driving power and operating frequency to each individual sector, the ultrasonic driver 840 can enhance the uniformity of the ultrasonic beam around the transducer 830, as well as can vary the degree of heating (i.e., lesion control) in the angular dimension.

The ultrasound transducer just described is combined with the overall device assembly according to the present embodiment as follows. In assembly, the transducer 830 desirably is "air-backed" to produce more energy and to enhance energy distribution uniformity, as known in the art. In other words, the inner member 803 does not contact an appreciable amount of the inner surface of transducer inner tubular member 834. This is because the piezoelectric crystal which forms central layer 832 of ultrasound transducer 830 is adapted to radially contract and expand (or radially "vibrate") when an alternating current is applied from a current source and across the outer and inner tubular electrodes 833,834 of the crystal via the electrical leads 836,837. This controlled vibration emits the ultrasonic energy that is adapted to ablate tissue and form a circumferential conduction block according to the present embodiment. Therefore, it is believed that appreciable levels of contact along the surface of the crystal may provide a dampening effect that would diminish the vibration of the crystal and thus limit the efficiency of ultrasound transmission.

For this purpose, the transducer 830 seats coaxial about the inner member 803 and is supported about the inner member 803 in a manner providing a gap between the inner member 803 and the transducer inner tubular member 834. That is, the inner tubular member 834 forms an interior bore 835 that loosely receives the inner member 803. Any of a variety of structures can be used to support the transducer 830 about the inner member 803. For instance, spacers or splines can be used to coaxially position the transducer 830 about the inner member 803 while leaving a generally annular space between these components. In the alternative, other conventional and known approaches to support the transducer can also be used. For instance, O-rings that circumscribe the inner member 803 and lie between the inner member 803 and the transducer 830 can support the transducer 830 in a manner similar to that illustrated in U.S. Pat. No. 5,606,974 to Castellano issued Mar. 4, 1997, and entitled "Catheter Having Ultrasonic Device." More detailed examples of the alternative transducer support structures just described are disclosed in U.S. Pat. No. 5,620,479 to Diederich, issued Apr. 15, 1997, and entitled "Method and Apparatus for Thermal Therapy of Tumors." The disclosures of these references are herein incorporated in their entirety by reference thereto.

In the illustrated embodiment, at least one stand-off region 838 is provided along inner member 803 in order to ensure that the transducer 830 has a radial separation from the inner member 803 to form a gap filled with air and/or other fluid. In one preferred mode shown in FIG. 31C, stand-off region 838 is a tubular member with a plurality of circumferentially spaced outer splines 839 that hold the majority of the transducer inner surface away from the surface of the stand-off between the splines, thereby minimizing dampening affects from the coupling of the transducer to the catheter. The tubular member that forms a stand-off such as stand-off region 838 in the FIG. 31C embodiment may also provide its inner bore as the guidewire lumen in the region of the ultrasound transducer, in the alternative to providing a separate stand-off coaxially over another tubular member which forms the inner member, such as according to the FIG. 31C embodiment.

In a further mode, the elongate catheter body 802 can also include additional lumens which lie either side by side to or coaxial with the guidewire lumen 804 and which terminate at ports located within the space between the inner member 803 and the transducer 830. A cooling medium can circulate through space defined by the stand-off 838 between the inner member 803 and the transducer 830 via these additional lumens. By way of example, carbon dioxide gas, circulated at a rate of 5 liters per minute, can be used as a suitable cooling medium to maintain the transducer at a lower operating temperature. It is believed that such thermal cooling would allow more acoustic power to transmit to the targeted tissue without degradation of the transducer material.

The transducer 830 desirably is electrically and mechanically isolated from the interior of the balloon 820. Again, any of a variety of coatings, sheaths, sealants, tubing and the like may be suitable for this purpose, such as those described in U.S. Pat. No. 5,620,479 to Diederich and U.S. Pat. No. 5,606,974 to Castellano. In the illustrated embodiment, as best illustrated in FIG. 31C, a conventional, flexible, acoustically compatible, and medical grade epoxy 842 is applied over the transducer 830. The epoxy 842 may be, for example, Epotek 301, Epotek 310, which is available commercially from Epoxy Technology, or Tracon FDA-8. In addition, a conventional sealant, such as, for example, General Electric Silicon II gasket glue and sealant, desirably is applied at the proximal and distal ends of the transducer 830 around the exposed portions of the inner member 803, wires 836,837 and stand-off region 838 to seal the space between the transducer 830 and the inner member 803 at these locations.

An ultra thin-walled polyester heat shrink tubing 844 or the like then seals the epoxy coated transducer. Alternatively, the epoxy covered transducer 830, inner member 803 along stand-off region 838 can be instead inserted into a tight thin wall rubber or plastic tubing made from a material such as Teflon®, polyethylene, polyurethane, silastic or the like. The tubing desirably has a thickness of 0.0005 to 0.003 inches.

When assembling the ablation device assembly, additional epoxy is injected into the tubing after the tubing is placed over the epoxy coated transducer 830. As the tube shrinks, excess epoxy flows out and a thin layer of epoxy remains between the transducer and the heat shrink tubing 844. These layers 842,844 protect the transducer surface, help acoustically match the transducer 830 to the load, makes the ablation device more robust, and ensures air-tight integrity of the air backing.

Although not illustrated in FIG. 31A in order to simplify the drawing, the tubing 844 extends beyond the ends of transducer 830 and surrounds a portion of the inner member 803 on either side of the transducer 830. A filler (not shown) can also be used to support the ends of the tubing 844. Suitable fillers include flexible materials such as, for example, but without limitation, epoxy, Teflon® tape and the like.

The ultrasonic actuator 840 generates alternating current to power the transducer 830. The ultrasonic actuator 840 drives the transducer 830 at frequencies within the range of about 5 MHz to about 20 MHz, and preferably for the illustrated application within the range of about 7 MHz to about 10 MHz. In addition, the ultrasonic driver can modulate the driving frequencies and/or vary power in order to smooth or unify the produced collimated ultrasonic beam. For instance, the function generator of the ultrasonic actuator 840 can drive the transducer at frequencies within the range of 6.8 MHz and 7.2 MHz by continuously or discretely sweeping between these frequencies.

The ultrasound transducer 830 of the present embodiment sonically couples with the outer skin of the balloon 820 in a manner that forms a circumferential conduction block at a location where a pulmonary vein extends from an atrium as follows. Initially, the ultrasound transducer is believed to emit its energy in a circumferential pattern that is highly collimated along the transducer's length relative to its longitudinal axis L (see FIG. 16D). The circumferential band therefore maintains its width and circumferential pattern over an appreciable range of diameters away from the source at the transducer. Also, the balloon is preferably inflated with fluid that is relatively ultrasonically transparent, such as, for example, degassed water. Therefore, by actuating the transducer 830 while the balloon 820 is inflated, the circumferential band of energy is allowed to translate through the inflation fluid and ultimately sonically couple with a circumferential band of balloon skin that circumscribes the balloon 820. Moreover, the circumferential band of balloon skin material may also be further engaged along a circumferential path of tissue which circumscribes the balloon, such as, for example, if the balloon is inflated within and engages a pulmonary vein wall, ostium, or region of atrial wall. Accordingly, where the balloon is constructed of a relatively ultrasonically transparent material, the circumferential band of ultrasound energy is allowed to pass through the balloon skin and into the engaged circumferential path of tissue such that the circumferential path of tissue is ablated.

Further to the transducer-balloon relationship just described, the energy is coupled to the tissue largely via the inflation fluid and balloon skin. It is believed that, for in vivo uses of the present invention, the efficiency of energy coupling to the tissue, and therefore ablation efficiency, may significantly diminish in circumstances where there is poor contact and conforming interface between the balloon skin and the tissue. Accordingly, it is contemplated that several different balloon types may be provided for ablating different tissue structures so that a particular shape may be chosen for a particular region of tissue to be ablated.

Figure 33A:
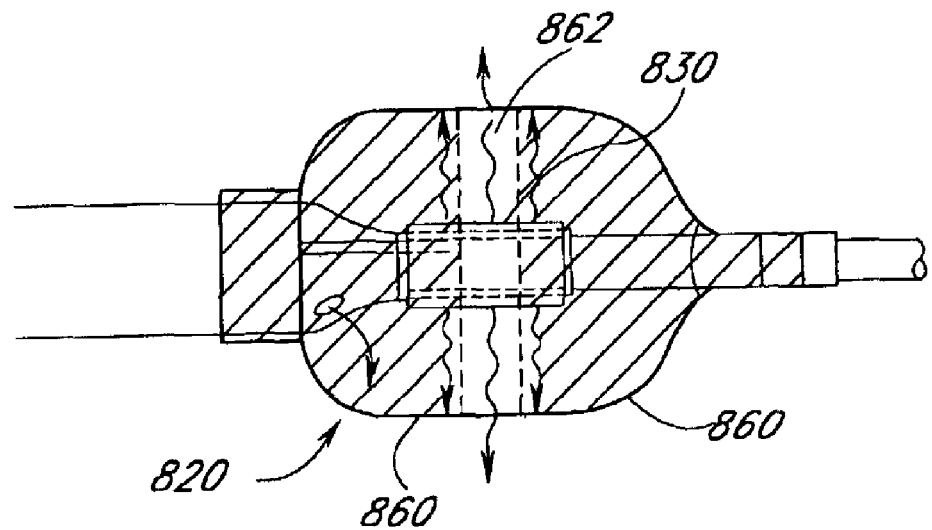
FIG. 33A shows a cross-sectional view of the distal end portion of another circumferential ablation catheter, wherein an outer shield or filter is provided along the balloon's outer surface in order to form a predetermined shape for the circumferential ablation element created by sonic transmissions from the inner ultrasound transducer.

In one particular balloon-transducer combination shown in FIG. 31A and also in FIG. 33A, the ultrasound transducer preferably has a length such that the ultrasonically coupled band of the balloon skin, having a similar length d according to the collimated ultrasound signal, is shorter than the working length D of the balloon. According to this aspect of the relationship, the transducer is adapted as a circumferential ablation member that is coupled to the balloon to form an ablation element along a circumferential band of the balloon, therefore forming a circumferential ablation element band that circumscribes the balloon. Preferably, the transducer has a length that is less than two-thirds the working length of the balloon, and more preferably is less than one-half the working length of the balloon. By sizing the ultrasonic transducer length d smaller than the working length D of the balloon 820—and hence shorter than a longitudinal length of the engagement area between the balloon 820 and the wall of the body space (e.g., pulmonary vein ostium)—and by generally centering the transducer 830 within the balloon's working length D, the transducer 830 operates in a field isolated from the blood pool. A generally equatorial position of the transducer 830 relative to the ends of the balloon's working length also assists in the isolation of the transducer 830 from the blood pool. It is believed that the transducer placement according to this arrangement may be preventative of thrombus formation that might otherwise occur at a lesion sight, particularly in the left atrium.

The ultrasound transducer described in various levels of detail above has been observed to provide a suitable degree of radiopacity for locating the energy source at a desired location for ablating the conductive block. However, it is further contemplated that the elongate catheter body 802 may include an additional radiopaque marker or markers (not shown) to identify the location of the ultrasonic transducer 830 in order to facilitate placement of the transducer at a selected ablation region of a pulmonary vein via X-ray visualization. The radiopaque marker is opaque under X-ray, and can be constructed, for example, of a radiopaque metal such as gold, platinum, or tungsten, or can comprise a radiopaque polymer such as a metal loaded polymer. The radiopaque marker is positioned coaxially over an inner tubular member 803, in a manner similar to that described in connection with the embodiment of FIG. 13.

The present circumferential ablation device is introduced into a pulmonary vein of the left atrium in a manner similar to that described above. Once properly positioned within the pulmonary vein or vein ostium, the pressurized fluid source inflates the balloon 820 to engage the lumenal surface of the pulmonary vein ostium. Once properly positioned, the ultrasonic driver 840 is energized to drive the transducer 830. It is believed that by driving the ultrasonic transducer 830 at 20 acoustical watts at an operating frequency of 7 MHz, that a sufficiently sized lesion can be formed circumferentially about the pulmonary vein ostium in a relatively short period of time (e.g., 1 to 2 minutes or less). It is also contemplated that the control level of energy can be delivered, then tested for lesion formation with a test stimulus in the pulmonary vein, either from an electrode provided at the tip area of the ultrasonic catheter or on a separate device such as a guidewire through the ultrasonic catheter. Therefore, the procedure may involve ablation at a first energy level in time, then check for the effective conductive block provided by the resulting lesion, and then subsequent ablations and testing until a complete conductive block is formed. In the alternative, the circumferential ablation device may also include feedback control, for example, if thermocouples are provided at the circumferential element formed along the balloon outer surface. Monitoring temperature at this location provides indicia for the progression of the lesion. This feedback feature may be used in addition to or in the alternative to the multi-step procedure described above.

Figure 32A:
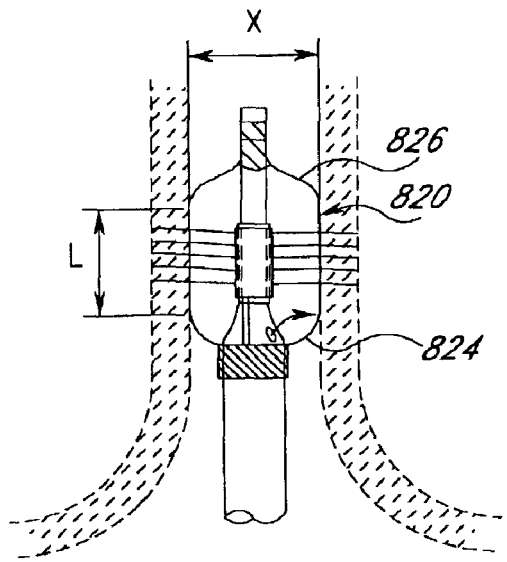
FIG. 32A shows a perspective view of a similar circumferential ablation catheter to the catheter shown in FIG. 31A, and shows the distal end portion of the circumferential ablation catheter during one mode of use in forming a circumferential conduction block at a location where a pulmonary vein extends from an atrium in the region of its ostium along a left atrial wall (shown in cross-section in shadow).
Figure 32B:
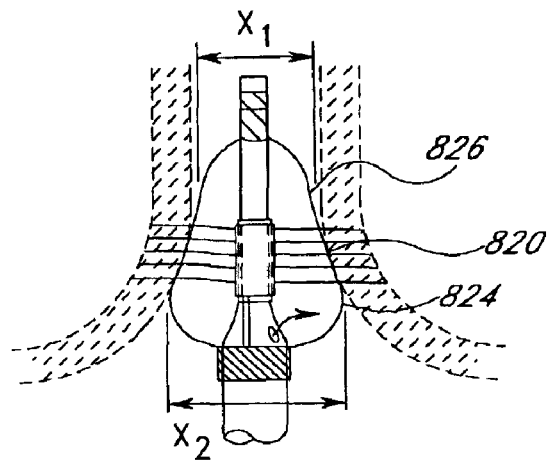
FIG. 32B shows a similar perspective and cross-section shadow view of a circumferential ablation catheter and pulmonary vein ostium as that shown in FIG. 32A, although shows another circumferential ablation catheter wherein the balloon has a tapered outer diameter.
Figure 32C:
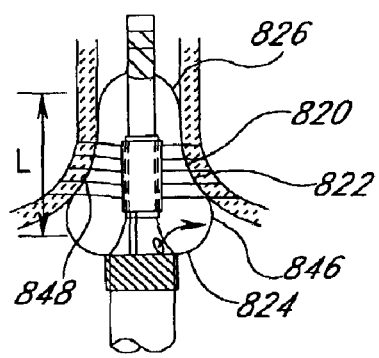
FIG. 32C shows a similar view to that shown in FIGS. 32A–B, although showing another circumferential ablation catheter wherein the balloon has a "pear"-shaped outer diameter with a contoured surface along a taper which is adapted to seat in the ostium of a pulmonary vein.
Figure 32D:
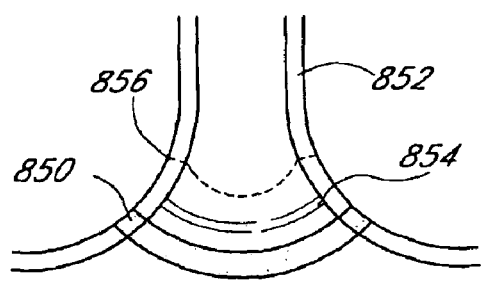
FIG. 32D shows a cross-sectional view of one circumferential conduction block which may be formed by use of a circumferential ablation catheter such as that shown in FIG. 32C.

FIGS. 32A–C show various alternative embodiments of the present invention for the purpose of illustrating the relationship between the ultrasound transducer and balloon of the present invention just described above. More specifically, FIG. 32A shows the balloon 820 having "straight" configuration with a working length D and a relatively constant diameter X between proximal and distal tapers 824,826. As is shown in FIG. 32A, this variation is believed to be particularly well adapted for use in forming a circumferential conduction block along a circumferential path of tissue which circumscribes and transects a pulmonary vein wall. However, unless the balloon is constructed of a material having a high degree of compliance and conformability, this shape may provide for gaps in contact between the desired circumferential band of tissue and the circumferential band of the balloon skin along the working length of the balloon 820.

The balloon 820 in FIG. 32A is also concentrically positioned relative to the longitudinal axis of the elongate catheter body 802. It is understood, however, that the balloon can be asymmetrically positioned on the elongate catheter body, and that the ablation device can include more than one balloon.

FIG. 32B shows another assembly according to the invention, although this assembly includes a balloon 820 that has a tapered outer diameter from a proximal outer diameter $X_1$ to a smaller distal outer diameter $X_2$. (Like reference numerals have been used in each of these embodiments in order to identify generally common elements between the embodiments.) According to this mode, this tapered shape is believed to conform well to other tapering regions of space, and may also be particularly beneficial for use in engaging and ablating circumferential paths of tissue along a pulmonary vein ostium.

FIG. 32C further shows a similar shape for the balloon as that just illustrated by reference to FIG. 32B, except that the FIG. 32C embodiment further includes a balloon 820 and includes a bulbous proximal end 846. In the illustrated embodiment, the proximate bulbous end 846 of the central region 822 gives the balloon 820 a "pear"-shape. More specifically, a contoured surface 848 is positioned along the tapered working length L and between proximal shoulder 824 and the smaller distal shoulder 826 of balloon 820. As is suggested by view of FIG. 32C, this pear shaped embodiment is believed to be beneficial for forming the circumferential conduction block along a circumferential path of atrial wall tissue that surrounds and perhaps includes the pulmonary vein ostium. For example, the device shown in FIG. 32C is believed to be suited to form a similar lesion to that shown at circumferential lesion 850 in FIG. 32D. Circumferential lesion 850 electrically isolates the respective pulmonary vein 852 from a substantial portion of the left atrial wall. The device shown in FIG. 32C is also believed to be suited to form an elongate lesion which extends along a substantial portion of the pulmonary vein ostium 854, e.g., between the proximal edge of the illustrated lesion 850 and the dashed line 856 which schematically marks a distal edge of such an exemplary elongate lesion 850.

As mentioned above, the transducer 830 can be formed of an array of multiple transducer elements that are arranged in series and coaxial. The transducer can also be formed to have a plurality of longitudinal sectors. These modes of the transducer have particular utility in connection with the tapering balloon designs illustrated in FIGS. 32B and 32C. In these cases, because of the differing distances along the length of the transducer between the transducer and the targeted tissue, it is believed that a non-uniform heating depth could occur if the transducer were driven at a constant power. In order to uniformly heat the targeted tissue along the length of the transducer assembly, more power may therefore be required at the proximal end than at the distal end because power falls off as 1/radius from a source (i.e., from the transducer) in water. Moreover, if the transducer 830 is operating in an attenuating fluid, then the desired power level may need to account for the attenuation caused by the fluid. The region of smaller balloon diameter near the distal end thus requires less transducer power output than the region of larger balloon diameter near the proximal end. Further to this premise, in a more specific embodiment transducer elements or sectors, which are individually powered, can be provided and produce a tapering ultrasound power deposition. That is, the proximal transducer element or sector can be driven at a higher power level than the distal transducer element or sector so as to enhance the uniformity of heating when the transducer lies skewed relative to the target site.

The circumferential ablation device 800 can also include additional mechanisms to control the depth of heating. For instance, the elongate catheter body 802 can include an additional lumen that is arranged on the body so as to circulate the inflation fluid through a closed system. A heat exchanger can remove heat from the inflation fluid and the flow rate through the closed system can be controlled to regulate the temperature of the inflation fluid. The cooled inflation fluid within the balloon 820 can thus act as a heat sink to conduct away some of the heat from the targeted tissue and maintain the tissue below a desired temperature (e.g., 90° C.), and thereby increase the depth of heating. That is, by maintaining the temperature of the tissue at the balloon/tissue interface below a desired temperature, more power can be deposited in the tissue for greater penetration. Conversely, the fluid can be allowed to warm. This use of this feature and the temperature of the inflation fluid can be varied from procedure to procedure, as well as during a particular procedure, in order to tailor the degree of ablation to a given application or patient.

The depth of heating can also be controlled by selecting the inflation material to have certain absorption characteristics. For example, by selecting an inflation material with higher absorption than water, less energy will reach the balloon wall, thereby limiting thermal penetration into the tissue. It is believed that the following fluids may be suitable for this application: vegetable oil, silicone oil and the like.

Uniform heating can also be enhanced by rotating the transducer within the balloon. For this purpose, the transducer 830 may be mounted on a torquable member that is movably engaged within a lumen that is formed by the elongate catheter body 802.

Another aspect of the balloon-transducer relationship of the present embodiment is illustrated by reference to FIGS. 33A–B. In general, as to the variations embodied by those Fig.'s, the circumferential ultrasound energy signal is modified at the balloon coupling level such that a third order of control is provided for the tissue lesion pattern (the first order of control is the transducer properties affecting signal emission, such as length, width, shape of the transducer crystal; the second order of control for tissue lesion pattern is the balloon shape, per above by reference to FIGS. 32A–C).

This third order of control for the tissue lesion pattern can be understood more particularly with reference to FIG. 33A, which shows balloon 820 to include a shield or filter 860. The filter 860 has a predetermined pattern along the balloon surface adapted to shield tissue from the ultrasound signal, for example, by either absorbing or reflecting the ultrasound signal. In the particular variation shown in FIG. 33A, the filter 860 is patterned so that the energy band which is passed through the balloon wall is substantially more narrow than the band that emits from the transducer 830 internally of the balloon 820. The filter 860 can be constructed, for example, by coating the balloon 820 with an ultrasonically reflective material, such as with a metal, or with an ultrasonically absorbent material, such as with a polyurethane elastomer. Or, the filter can be formed by varying the balloon's wall thickness such that a circumferential band 862, which is narrow in the longitudinal direction as compared to the length of the balloon, is also thinner (in a radial direction) than the surrounding regions, thereby preferentially allowing signals to pass through the band 862. The thicker walls of the balloon 820 on either side of the band 862 inhibit propagation of the ultrasonic energy through the balloon skin at these locations.

For various reasons, the "narrow pass filter" embodiment of FIG. 34A may be particularly well suited for use in forming circumferential conduction blocks in left atrial wall and pulmonary vein tissues according to the present invention. It is believed that the efficiency of ultrasound transmission from a piezoelectric transducer is limited by the length of the transducer, which limitations are further believed to be a function of the wavelength of the emitted signal. Thus, for some applications a transducer 830 may be required to be longer than the length that is desired for the lesion to be formed. Many procedures intending to form conduction blocks in the left atrium or pulmonary veins, such as, for example, less-invasive "maze"-type procedures, require only enough lesion width to create a functional electrical block and to electrically isolate a tissue region. In addition, limiting the amount of damage formed along an atrial wall, even in a controlled ablation procedure, pervades as a general concern. However, a transducer that is necessary to form that block, or which may be desirable for other reasons, may require a length that is much longer and may create lesions that are much wider than is functionally required for the block. A "narrow pass" filter along the balloon provides one solution to such competing interests.

Figure 33B:
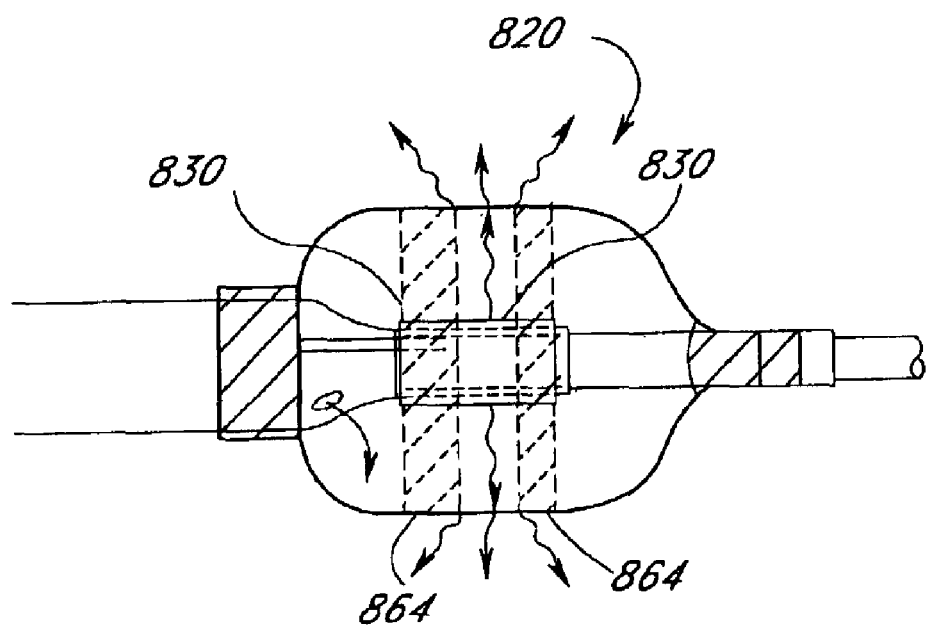
FIG. 33B shows a similar view as that shown in FIG. 33A, although showing the distal end portion of another circumferential ablation catheter which includes a heat sink as an equatorial band within the circumferential path of energy emission from an inner ultrasound transducer.

FIG. 33B shows another variation of the balloon-transducer relationship in an ultrasound ablation assembly according to the present invention. Unlike the variation shown in FIG. 34A, FIG. 33B shows placement of an ultrasonically absorbent band 864 along balloon 820 and directly in the central region of the emitted energy signal from transducer 830. According to this variation, the ultrasonically absorbent band 864 is adapted to heat to a significant temperature rise when sonically coupled to the transducer via the ultrasound signal. It is believed that some ablation methods may benefit from combining ultrasound/thermal conduction modes of ablation in a targeted circumferential band of tissue. In another aspect of this variation, ultrasonically absorbent band 864 may operate as an energy sink as an aid to control the extent of ablation to a less traumatic and invasive level than would be reached by allowing the raw ultrasound energy to couple directly to the tissue. In other words, by heating the absorbent band 864 the signal is diminished to a level that might have a more controlled depth of tissue ablation. Further to this aspect, absorbent band 864 may therefore also have a width that is more commensurate with the length of the transducer, as is shown in an alternative mode in shadow at absorbent band 864.

In each of the embodiments illustrated in FIGS. 31A through 33B, the ultrasonic transducer had an annular shape so as to emit ultrasonic energy around the entire circumference of the balloon. The present circumferential ablation device, however, can emit a collimated beam of ultrasonic energy in a specific angular exposure. For instance, as seen in FIG. 34A, the transducer can be configured to have only a single active sector (e.g., 180 degree exposure). The transducer can also have a planar shape. By rotating the elongate catheter body 802, the transducer 830 can be swept through 360 degrees in order to form a circumferential ablation. For this purpose, the transducer 830 may be mounted on a torquable member 803, in the manner described above.

FIG. 34B illustrates another type of ultrasonic transducer that can be mounted to a torquable member 803 within the balloon 820. The transducer 830 is formed by curvilinear section and is mounted on the inner member 803 with its concave surface facing in a radially outward direction. The inner member 803 desirably is formed with recess that substantially matches a portion of the concave surface of the transducer 830. The inner member 803 also includes longitudinal ridges on the edges of the recess that support the transducer above the inner member such that an air gap is formed between the transducer and the inner member. In this manner, the transducer is "air-backed." This spaced is sealed and closed in the manner described above in connection with the embodiment of FIGS. 31A–E.

The inverted transducer section produces a highly directional beam pattern. By sweeping the transducer through 360 degrees of rotation, as described above, a circumferential lesion can be formed while using less power than would be required with a planar or tubular transducer.

The embodiments shown in FIGS. 35A–41 represent variations of the circumferential ablation device assemblies incorporating ultrasonic ablation elements as previously shown and described by reference to FIGS. 31A–34B. These additional embodiments particularly adapt such ultrasound ablation members for use in ablating along a funneling, tapered pulmonary vein ostium or along a posterior left atrial wall tissue and surrounding the pulmonary vein's ostium.

Figure 35A:
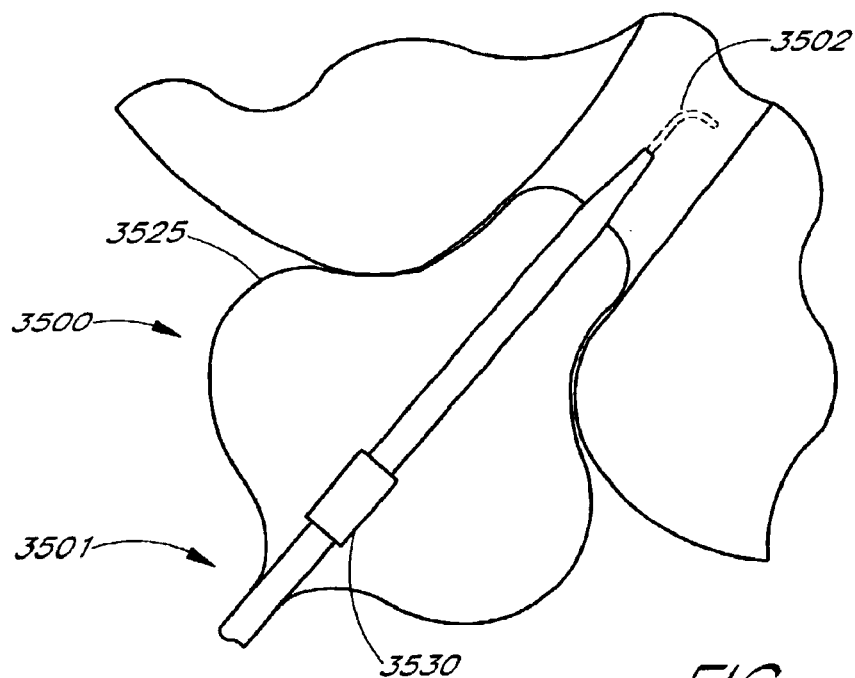
FIG. 35A shows a schematic perspective view of another circumferential ablation member during use in forming a circumferential lesion according to the present invention.

FIG. 35A schematically illustrates formation of a lesion through a forward or distal facing wall of a distally tapered balloon 3525 to form a lesion surrounding a pulmonary vein ostium, such as previously described above for circumferential ablation along a posterior left atrial wall surrounding a vessel ostium, or otherwise along the ostium. As shown in FIG. 35A, the ultrasonic circumferential ablation device assembly 3501 may be adapted to track over a guidewire 3502 and into a pulmonary vein. The lesion 3560 surrounding a pulmonary vein ostium 3555 to which this embodiment is adapted to form is representative of those lesions which the other embodiments in FIGS. 16A–30 are also adapted to form. More specifically to this ultrasound variation, transducer 3530 is adapted to send a signal along a circumferential pattern that emits "forward" through the tapered wall of balloon 3525 and into the tissue engaged thereby.

Figure 35B:
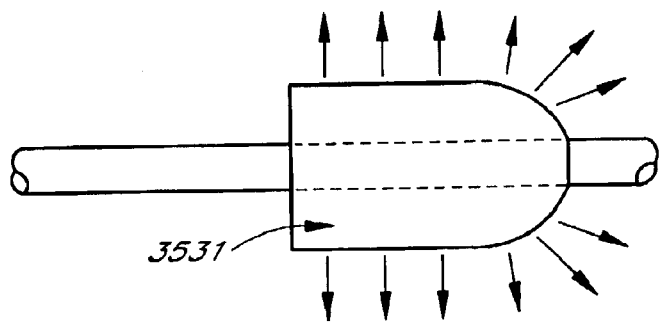
FIG. 35B shows one ultrasound transducer that has a shape which is adapted for use in a circumferential ablation member such as that shown in FIG. 35A in order to ablate a circumferential region of tissue.
Figure 35E:
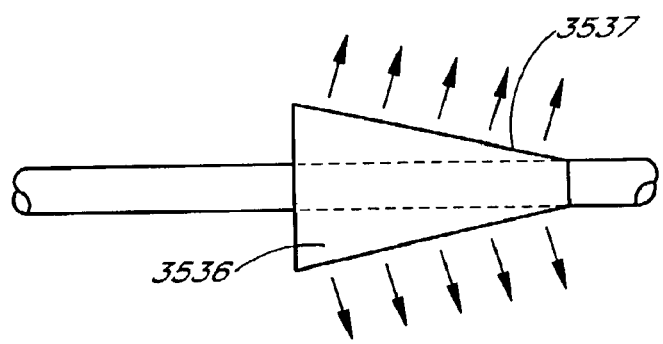
FIG. 35E shows another ablation element that is adapted to ablate a circumferential region of tissue when used in a circumferential ablation member such as that shown in FIG. 35A.
Figure 35C:
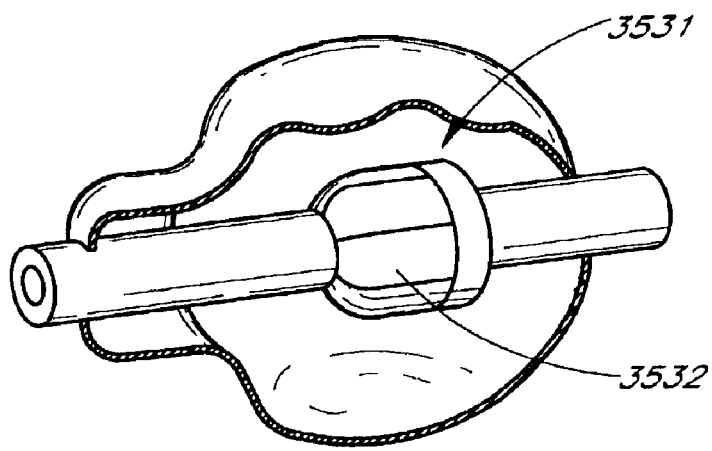
FIG. 35C shows a schematic perspective view of a circumferential ablation member incorporating the ablation element shown in FIG. 35B within an expandable member.
Figure 35D:
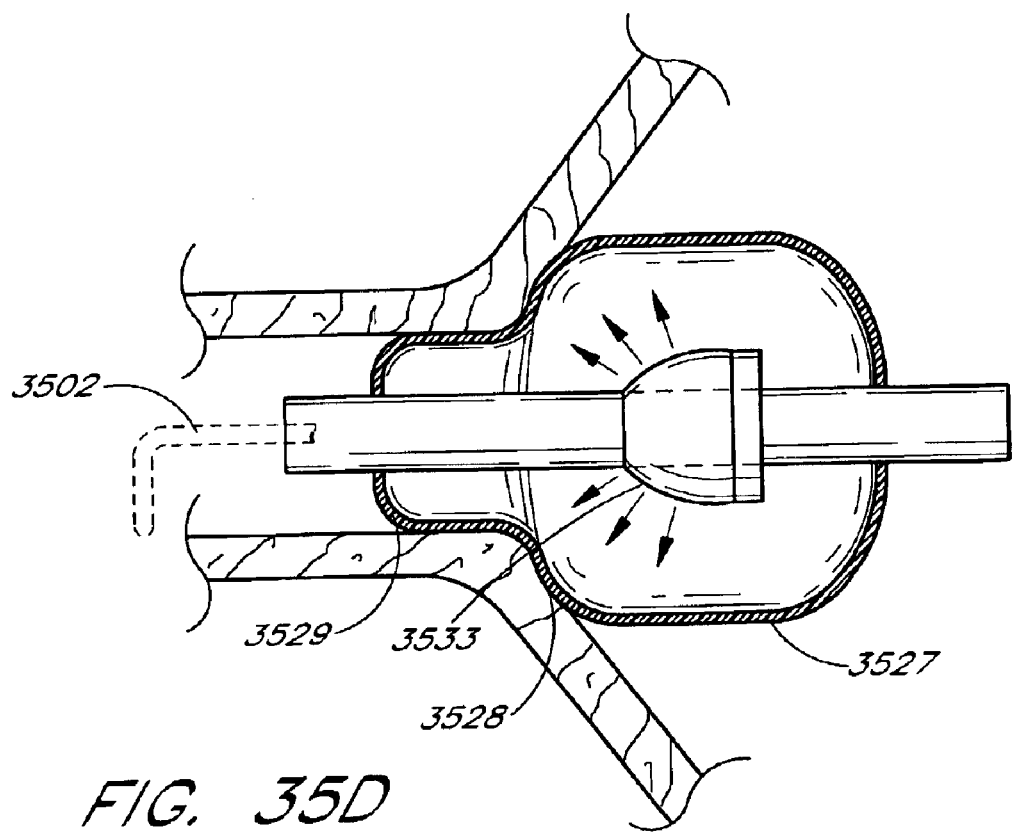
FIG. 35D shows a longitudinal side view of the circumferential ablation member shown in FIG. 35C during use in ablating a circumferential region of tissue in a similar manner as is shown in FIG. 35A.

FIGS. 35B–D show a specific mode wherein transducer assembly 3531 has an arcuate, circumferential distal face 3533 that emits a distally or forward oriented circumferential pattern. A pair-shaped or distally-tapered expandable member 3527 surrounds the transducer and engages the pulmonary vein ostium. The distal end 3529 is adapted to engage the pulmonary vein. The forwardly focused ultrasonic energy passes through the distally tapered wall 3528 of expandable member 3527. In addition, shown schematically such transducer assembly 3531 may comprise a plurality of flat panels such as at 3532 that are individually driven. It is contemplated that such arcuate transducer crystal surfaces may require complex poling in the forward or angled direction desired for emission, as would be apparent to one of ordinary skill based upon this disclosure.

Figure 35F:
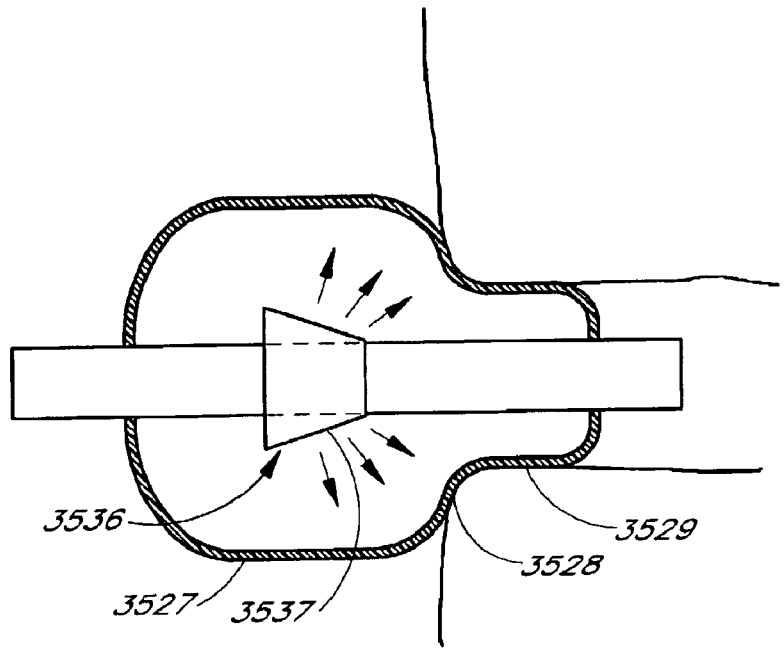
FIG. 35F shows a longitudinal side view of a circumferential ablation member incorporating the ablation element shown in FIG. 35E during use in ablating a circumferential region of tissue.
Figure 35G:
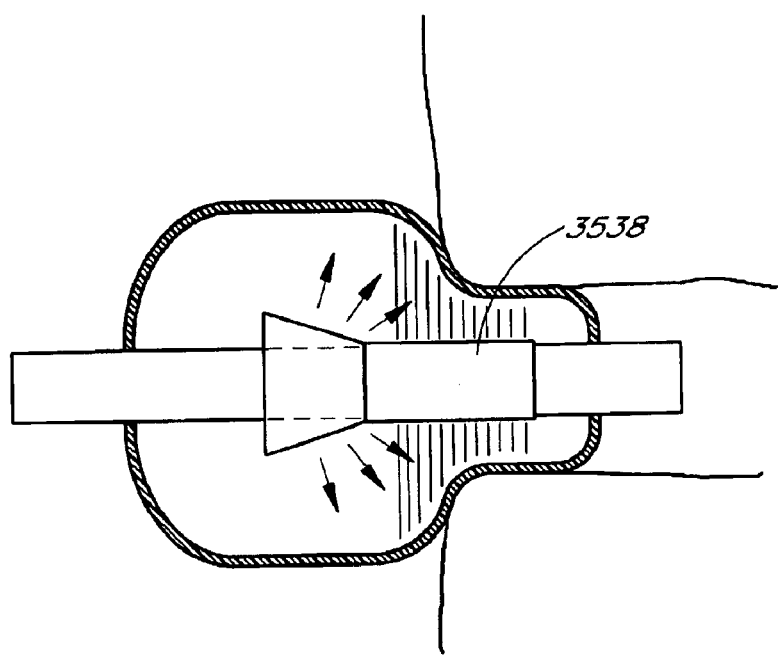
FIG. 35G shows a longitudinal side view of another circumferential ablation member which is similar to that shown in FIG. 35F, except that the shaped ultrasound transducer further includes both a distally oriented conical face a generally cylindrical portion, and shows the circumferential ablation member during use in ablating a circumferential region of tissue according to the invention.

FIGS. 35E–G show a further variation, wherein the transducer crystal 3536 is conically shaped with a distally facing surface 3537 for emitting the desired energy through distally tapered wall 3528 of balloon 3527. This shape similarly requires poling in the orthogonal plane to the surface for desired ablation. In a further variation, FIG. 35H also shows a radially oriented portion of the transducer at circumferential emitter 3538, which may be described according to prior disclosed designs shown above.

A series of circumferentially spaced ultrasonic panels may also be used in the circumferential ablation member of the present invention, as shown variously in FIGS. 36A–39B.

FIGS. 36A–C show circumferentially spaced arcuate panels 3630 which surround inner member 3611 in radially extended positions such that distal surfaces 3632 are pointing toward the region to ablate along a distal aspect of the assembly such as along inner member 3611. FIGS. 37A–C show a further variation wherein such ultrasound panels 3730 have a substantially flat shape. In a radially extended position, the flat panel 3730 presents a distal surface 3732 that is angled toward the region of tissue to be ablated.

Figure 37D:
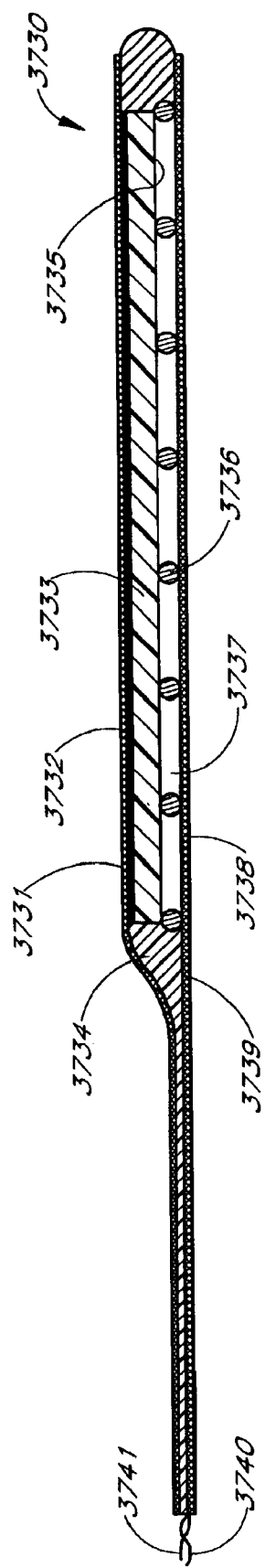
FIG. 37D shows an exploded longitudinal cross-sectioned view of one ultrasound panel for use in an ablation element such as those shown in FIGS. 37A–C.
Figure 39A:
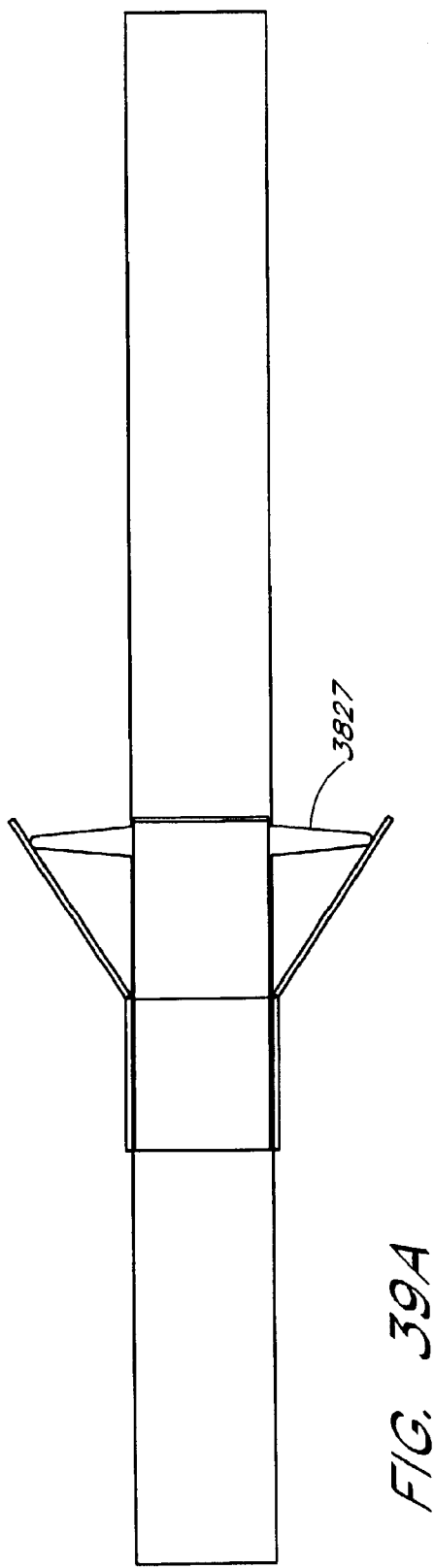
FIG. 39 shows a schematic longitudinal side view of a circumferential ablation member for use in ablating a circumferential region of tissue such as according to FIG. 35A, wherein a tapered distal surface of the inflatable balloon is adapted to deflect the angle of ultrasound energy toward the circumferential region of tissue.
Figure 39B:
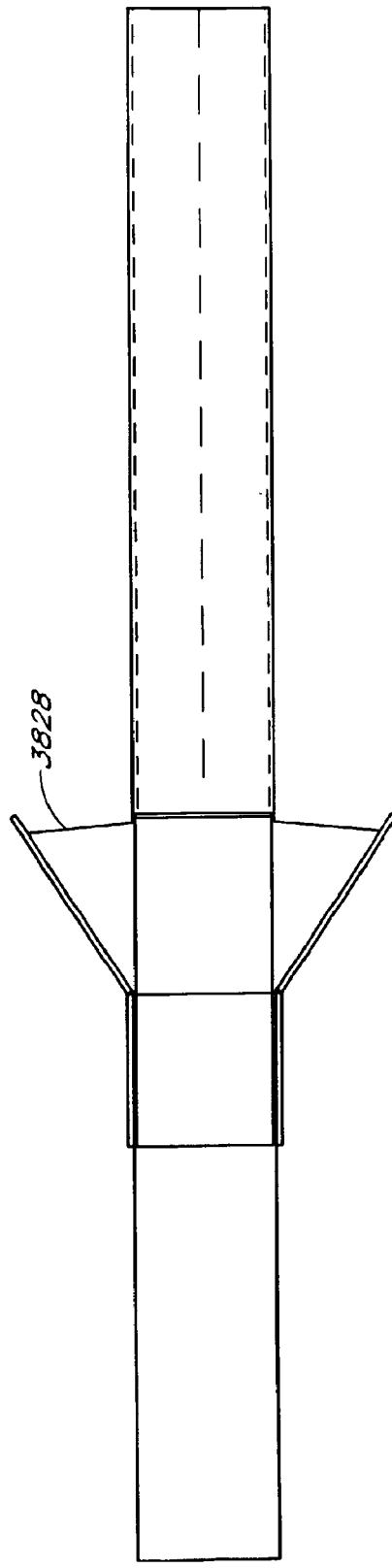

One more detailed construction for such ultrasound transducer panels is shown in FIG. 37D. The ultrasound transducer 3730 is formed from a crystal 3733 having an outer surface 3732 and an inner surface 3735, as detailed with respect to the cylindrical ultrasound transducer assemblies described in connection with FIGS. 31A–E. An adhesive layer may be applied between the transducer surfaces. Further, an outer jacket 3731 may be applied over the to the distal-facing surface of the transducer panel including the outer surface 3732 of the transducer crystal. Separate electrical leads 3740 and 3741 connect to electrodes on the outer 3732 and inner 3735 surfaces of the transducer. The ultrasound transducer just described is combined with the overall device assembly according to the present embodiment as follows. In assembly, the transducer 3730 is desirably "airbacked" to produce more energy and to enhance energy distribution uniformity, as known in the art. In other words, the inner surface of the transducer 3735 does not contact an appreciable amount of the proximal surface 3738 of the panel. The air-backing is maintained by any variety of set-off structures 3736 known in the art, such as elastomeric spacers, stand-off's, etc. In addition, or in the alternative, a mounting material 3734, including for example an epoxy a polymeric molded material, may be used to support the transducer crystal within the panel.

The transducer panels are adjustable from a radially collapsed position to a radially extended position by use of an expansion member, as shown in various modes by balloon 3825, braided cage 3826, adjustable splines 3827, and adjustable stand-off 3828, in FIGS. 38A, 38B, 39A, and 39B, respectively. Actuation of these expansion members can be accomplished as described elsewhere in this specification in connection with other embodiments of the present invention.

FIG. 40 shows a further embodiment of an ultrasound ablation device for making circumferential lesions in the posterior wall of the left atrium around pulmonary vein(s). A circumferential ablation pattern perpendicular to the catheter shaft and ultrasound transducer 4030 is generated by deflecting the ultrasound energy using a surface 4004 along a tapered balloon 4025. Thus, the ultrasound energy is directed toward a distal direction for ablative coupling into tissue contacting that surface.

FIG. 41 shows another variation, wherein the radial circumferential ultrasound generated by the ultrasound transducer 4130 is deflected by a rearward taper 4106 of the balloon 4125 and toward and through the distal taper 4108. These last two embodiments may be accomplished for example by varying the material of the balloon, or by coating the balloon or otherwise providing a material in the described location for ultrasonic signal re-direction. Furthermore, such variations may be used with other energy sources, such as for example laser energy, which may be similarly redirected toward a distal balloon taper where it interfaces with posterior left atrial wall tissue.

It is to be further understood that the various modes of the ultrasound-balloon embodiments just illustrated by reference to FIGS. 31A–34B may be used according to several different particular methods such as those methods otherwise set forth throughout this disclosure. For example, any of the ultrasound transducer embodiments may be used to form a conduction block in order to prevent or treat focal arrhythmia arising from a specific pulmonary vein, or may alternatively or additionally be used for joining adjacent linear lesions in a less-invasive "maze"-type procedure.

As discussed above, the embodiments described herein are believed to be particularly useful in catheter assemblies that are specifically adapted for ablating tissue along a region where a pulmonary vein extends from a left atrium in the treatment of atrial fibrillation. Therefore, the assemblies and methods of the present invention are also contemplated for use in combination with, or where appropriate in the alternative to, the various particular features and embodiments shown and described in the following co-pending U.S. Patent Applications that also address circumferential ablation at a location where a pulmonary vein extends from an atrium:. U.S. Ser. No. 08/889,798 for "CIRCUMFERENTIAL ABLATION DEVICE ASSEMBLY" to Michael D. Lesh et al., filed Jul. 8, 1997; U.S. Ser. No. 08/889,835 for "DEVICE AND METHOD FOR FORMING A CIRCUMFERENTIAL CONDUCTION BLOCK IN A PULMONARY VEIN" to Michael D. Lesh, filed Jul. 8, 1997; U.S. Ser. No. 09/199,736 for "CIRCUMFERENTIAL ABLATION DEVICE ASSEMBLY" to Chris J. Diederich et al., filed Feb. 3, 1998; and U.S. Ser. No. 09/260,316 for "DEVICE AND METHOD FOR FORMING A CIRCUMFERENTIAL CONDUCTION BLOCK IN A PULMONARY VEIN" to Michael D. Lesh. The disclosures of these references are herein incorporated in their entirety by reference thereto.

It is further contemplated that the embodiments shown and described herein may be combined, assembled together, or where appropriate substituted for, the various features and embodiments which are disclosed in the following co-pending provisional and non-provisional U.S. Patent Applications: the co-pending non-provisional U.S. Patent Application for "FEEDBACK APPARATUS AND METHOD FOR ABLATION AT PULMONARY VEIN OSTIUM", filed on the same day as this Application, and claiming priority to Provisional U.S. patent application Ser. No. 60/122,571, filed on Mar. 2, 1999; co-pending Provisional U.S. patent application Ser. No. 60/133,610 for "BALLOON ANCHOR WIRE", filed May 11, 1999; the co-pending non-provisional U.S. Patent Application for "TISSUE ABLATION DEVICE ASSEMBLY AND METHOD FOR ELECTRICALLY ISOLATING A PULMONARY VEIN OSTIUM FROM A POSTERIOR LEFT ATRIAL WALL", filed on the same day as this Application, and which claims priority to Provisional U.S. patent application Ser. No. 60/133,677, filed May 11, 1999; the co-pending non-provisional U.S. Patent Application for "APPARATUS AND METHOD INCORPORATING AN ULTRASOUND TRANSDUCER ONTO A DELIVERY MEMBER", filed on the same day as this Application, and which claims priority to Provisional U.S. patent application Ser. No. 60/133,680, filed May 11, 1999; and co-pending Provisional U.S. Patent Application Ser. No. 60/133,807 for "CATHETER POSITIONING SYSTEM". The disclosures of these references are herein incorporated in their entirety by reference thereto.

In addition, a circumferential ablation device assembly according to the present invention may be used in combination with other linear ablation assemblies and methods, and various related components or steps of such assemblies or methods, respectively, in order to form a circumferential conduction block adjunctively to the formation of long linear lesions, such as in a less-invasive "maze"-type procedure. Examples of such assemblies and methods related to linear lesion formation and which are contemplated in combination with the presently disclosed embodiments are shown and described in the following additional co-pending U.S. patent applications and patents: U.S. Pat. No. 5,971,983, issued on Oct. 26, 1999, entitled "TISSUE ABLATION DEVICE AND METHOD OF USE" filed by Michael Lesh, M.D. on May 9, 1997; U.S. Ser. No. 09/260,316 for "TISSUE ABLATION SYSTEM AND METHOD FOR FORMING LONG LINEAR LESION" to Langberg et al., filed May 1, 1999; and U.S. Ser. No. 09/073,907 for "TISSUE ABLATION DEVICE WITH FLUID IRRIGATED ELECTRODE", to Alan Schaer et al., filed May 6, 1998. The disclosures of these references are herein incorporated in their entirety by reference thereto.

While a number of variations of the invention have been shown and described in detail, other modifications and methods of use contemplated within the scope of this invention will be readily apparent to those of skill in the art based upon this disclosure. It is contemplated that various combinations or subcombinations of the specific embodiments may be made and still fall within the scope of the invention. For example, the embodiments variously shown to be "guidewire" tracking variations for delivery into a left atrium and around or within a pulmonary vein may be modified to instead incorporate a deflectable/steerable tip instead of guidewire tracking and are also contemplated. Moreover, all assemblies described are believed useful when modified to treat other tissues in the body, in particular other regions of the heart, such as the coronary sinus and surrounding areas. Further, the disclosed assemblies may be useful in treating other conditions, wherein aberrant electrical conduction may be implicated, such as for example, heart flutter. Indeed, other conditions wherein catheter-based, directed tissue ablation may be indicated, such as for example, in the ablation of fallopian tube cysts. Accordingly, it should be understood that various applications, modifications and substitutions may be made of equivalents without departing from the spirit of the invention or the scope of the following claims.

The following claims are provided to illustrate examples of some beneficial aspects of the subject matter disclosed herein which are within the scope of the present invention.

What is claimed is:

1. A tissue ablation system for treating atrial arrhythmia by ablating a circumferential region of tissue at a location where a pulmonary vein extends from an atrium, comprising:

a delivery member having a proximal end portion and a distal end portion with a longitudinal axis and a radial axis;

a housing with a distal wall, that is located at least in part along the distal end portion, and that is mechanically adjustable between a first condition and a second condition, wherein the first condition the distal wall is substantially radially collapsed such that the housing is adapted to be delivered through a delivery sheath into the atrium, and wherein the second condition the distal wall is radially extended at least in part from the longitudinal axis with a distal orientation and a distal facing surface located along a circumferential region that surrounds the longitudinal axis;

a mechanical positioning assembly coupled to the housing to mechanically adjust the housing between the first and second conditions; and an ablation element cooperating with the housing and which is adapted to ablatively couple to a circumferential area normal to the distal facing surface along the circumferential region when the housing is in the second position, wherein the ablation element and distal facing surface are configured such that the circumferential area coincides with the circumferential region of tissue when the housing is adjusted to the second condition at the location, and wherein in the second condition the distal wall along the circumferential region comprises a porous membrane that encloses at least in part a fluid chamber within the housing;

the distal facing surface is located along the porous membrane; and the porous membrane is adapted to ablatively couple a volume of ablative fluid within the fluid chamber to the circumferential area.

2. The system of claim 1, wherein the porous membrane is adapted to allow the volume of ablative fluid to flow from within the fluid chamber and into the circumferential area.

3. The system of claim 1, wherein the ablation element comprises a volume of ablative fluid medium within the fluid chamber and that ablatively couples with the circumferential area across the porous membrane.

4. The system of claim 1, wherein the porous membrane comprises a porous tetrafluoropolymer.

5. The system of claim 1, wherein the ablation element comprises an ablative energy source located within the fluid chamber.

6. A tissue ablation system for treating atrial arrhythmia by ablating a circumferential region of tissue at a location where a pulmonary vein extends from an atrium, comprising:

a delivery member having a proximal end portion and a distal end portion with a longitudinal axis and a radial axis;

a housing with a distal wall, that is located at least in part along the distal end portion, and that is mechanically adjustable between a first condition and a second condition, wherein the first condition the distal wall is substantially radially collapsed such that the housing is adapted to be delivered through a delivery sheath into the atrium, and wherein the second condition the distal wall is radially extended at least in part from the longitudinal axis with a distal orientation and a distal facing surface located along a circumferential region that surrounds the longitudinal axis;

a mechanical positioning assembly coupled to the housing, to mechanically adjust the housing between the first and second conditions, and to the delivery member; and an ablation element cooperating with the housing and which is adapted to ablatively couple to a circumferential area normal to the distal facing surface along the circumferential region when the housing is in the second position, wherein the ablation element and distal facing surface are configured such that the circumferential area coincides with the circumferential region of tissue when the housing is adjusted to the second condition at the location.

7. The system of claim 6, wherein the housing further comprises a proximal wall that in the second condition has a proximally facing surface, and the proximal wall is connected to the distal wall.

8. The system of claim 7, wherein the distal and proximal walls are formed from an integral member.

9. The system of claim 7, wherein the distal wall in the second position further comprises an outer circumferential region that circumscribes the circumferential region that includes the distal facing surface, and also an inner circumferential region that is circumscribed by the circumferential region that includes the distal facing surface; and the distal and proximal walls are connected along at least one of the outer and inner circumferential regions.

10. The system of claim 7, wherein the distal wall in the second position further comprises an inner circumferential region that is circumscribed by the circumferential region that includes the distal facing surface; and the mechanical positioning assembly comprises at least one support member extending between the distal and proximal walls at least across the inner circumferential region and the circumferential region that includes the distal facing surface.

11. The system of claim 6, wherein the mechanical positioning assembly comprises an array of splines that are circumferentially spaced around the longitudinal axis, each spline having a distal end portion coupled to the distally oriented wall and a proximal end portion coupled to the distal end portion, and wherein each of the array of splines is adjustable between a first position which is substantially radially collapsed and extending along the longitudinal axis and a second position wherein the distal end portion of the spline extends radially outwardly from the longitudinal axis, such that the first and second positions for the splines characterize at least in part the first and second conditions for the housing.

12. The system of claim 11, wherein the ablation element comprises an energy source that is located along a spline at a position corresponding to the circumferential region.

13. The system of claim 6, wherein the ablation element comprises an ablation means.

14. The system of claim 6, wherein the ablation element comprises a microwave ablation element.

15. The system of claim 6, wherein the ablation element comprises a cryogenic ablation element.

16. The system of claim 6, wherein the ablation element comprises a thermal ablation element.

17. The system of claim 6, wherein the ablation element comprises a light emitting ablation element.

18. The system of claim 6, wherein the ablation element comprises a light emitting ablation element.

19. The system of claim 6, wherein the ablation element comprises an ultrasonic ablation element.

* * * * *